(12) United States Patent
Velicelebi et al.

(10) Patent No.: US 10,821,109 B1
(45) Date of Patent: *Nov. 3, 2020

(54) PYRAZINE-CONTAINING COMPOUND

(71) Applicant: CalciMedica, Inc., La Jolla, CA (US)

(72) Inventors: Gonul Velicelebi, San Diego, CA (US); Kenneth Stauderman, San Diego, CA (US); Michael Dunn, La Jolla, CA (US); Jack Roos, San Diego, CA (US)

(73) Assignee: CALCIMEDICA, INC., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/988,508

(22) Filed: Aug. 7, 2020

Related U.S. Application Data

(63) Continuation of application No. 15/553,531, filed as application No. PCT/US2016/019924 on Feb. 26, 2016.

(60) Provisional application No. 62/126,386, filed on Feb. 27, 2015.

(51) Int. Cl.
| | | |
|---|---|---|
| *A61K 31/497* | (2006.01) |
| *C07D 401/04* | (2006.01) |
| *A61K 31/415* | (2006.01) |
| *A61K 31/427* | (2006.01) |
| *A61K 31/485* | (2006.01) |
| *C07D 405/04* | (2006.01) |
| *C07D 417/14* | (2006.01) |
| *A61K 31/444* | (2006.01) |
| *A61K 31/4155* | (2006.01) |
| *A61K 31/506* | (2006.01) |
| *A61K 31/421* | (2006.01) |
| *C07D 417/10* | (2006.01) |
| *A61K 31/4439* | (2006.01) |
| *C07D 491/04* | (2006.01) |
| *C07D 413/14* | (2006.01) |
| *A61P 1/18* | (2006.01) |
| *A61K 45/06* | (2006.01) |

(52) U.S. Cl.
CPC .......... *A61K 31/497* (2013.01); *A61K 31/415* (2013.01); *A61K 31/4155* (2013.01); *A61K 31/421* (2013.01); *A61K 31/427* (2013.01); *A61K 31/444* (2013.01); *A61K 31/4439* (2013.01); *A61K 31/485* (2013.01); *A61K 31/506* (2013.01); *A61K 45/06* (2013.01); *A61P 1/18* (2018.01); *C07D 401/04* (2013.01); *C07D 405/04* (2013.01); *C07D 413/14* (2013.01); *C07D 417/10* (2013.01); *C07D 417/14* (2013.01); *C07D 491/04* (2013.01); *Y02A 50/30* (2018.01)

(58) Field of Classification Search
CPC ................ A61K 31/497; A61K 31/415; A61K 31/4155; A61K 31/421; A61K 31/427; A61K 31/4439; A61K 31/444; A61K 31/485; A61K 31/506; A61K 45/06; C07D 401/04; C07D 405/04; C07D 413/14; C07D 417/10; C07D 417/14

USPC .......................................................... 514/289
See application file for complete search history.

(56) References Cited

U.S. PATENT DOCUMENTS

| | | | |
|---|---|---|---|
| 6,348,480 | B1 | 2/2002 | Kubota et al. |
| 6,506,747 | B1 | 1/2003 | Betageri et al. |
| 6,958,339 | B2 | 10/2005 | Kubota et al. |
| 7,709,518 | B2 | 5/2010 | Chen et al. |
| 7,816,535 | B2 | 10/2010 | Bohnert et al. |
| 8,030,336 | B2 | 10/2011 | Burns et al. |
| 8,546,403 | B2 | 10/2013 | Whitten et al. |
| 8,980,629 | B2 | 3/2015 | Whitten et al. |
| 9,120,751 | B2 | 9/2015 | Whitten et al. |
| 9,399,638 | B2 | 7/2016 | Irlapati et al. |
| 10,106,529 | B2 | 10/2018 | Whitten et al. |
| 10,478,435 | B2 | 11/2019 | Stauderman et al. |
| 10,703,722 | B2 | 7/2020 | Whitten et al. |
| 2001/0044445 | A1 | 11/2001 | Bamaung et al. |
| 2002/0034728 | A1 | 3/2002 | Normant et al. |
| 2006/0030567 | A1 | 2/2006 | Ehrenfreund et al. |
| 2006/0100215 | A1 | 5/2006 | Bakthavatchalam et al. |
| 2006/0199845 | A1 | 9/2006 | Sun et al. |
| 2006/0235028 | A1 | 10/2006 | Li et al. |

(Continued)

FOREIGN PATENT DOCUMENTS

| | | |
|---|---|---|
| JP | 2001080412 A | 3/2001 |
| JP | 2001522834 A | 11/2001 |

(Continued)

OTHER PUBLICATIONS

Arthritis. http://en.wikipedia.org/wiki/Arthritis (1 pg.) (2014).

(Continued)

*Primary Examiner* — Yevgeny Valenrod
(74) *Attorney, Agent, or Firm* — Wilson Sonsini Goodrich & Rosati

(57) ABSTRACT

Compositions and methods related to the amelioration of pancreatitis through the pharmaceutical manipulation of calcium signaling are disclosed. Such compositions and methods may be used to ameliorate symptoms of acute or chronic pancreatitis or to reduce the chance or severity of pancreatitis in an individual at risk of the condition. In other embodiments, disclosed herein are compositions and methods related to the amelioration of viral diseases through the pharmaceutical manipulation of calcium signaling. In further embodiments, disclosed herein are compositions and methods related to the amelioration of Th17-induced diseases through the pharmaceutical manipulation of calcium signaling.

2 Claims, 21 Drawing Sheets

(56) References Cited

U.S. PATENT DOCUMENTS

| | | |
|---|---|---|
| 2007/0031814 A1 | 2/2007 | Roos et al. |
| 2007/0105867 A1 | 5/2007 | Chidambaram et al. |
| 2007/0249050 A1 | 10/2007 | Chen et al. |
| 2007/0249609 A1 | 10/2007 | Chen et al. |
| 2007/0254363 A1 | 11/2007 | Chen et al. |
| 2007/0254912 A1 | 11/2007 | Chen et al. |
| 2007/0254925 A1 | 11/2007 | Vo et al. |
| 2007/0254926 A1 | 11/2007 | Jiang et al. |
| 2008/0064874 A1 | 3/2008 | Dunkel et al. |
| 2008/0293092 A1 | 11/2008 | Stauderman et al. |
| 2009/0311720 A1 | 12/2009 | Roos et al. |
| 2010/0016598 A1 | 1/2010 | Valacchi et al. |
| 2010/0041762 A1 | 2/2010 | Bohnert et al. |
| 2010/0130510 A1 | 5/2010 | Chen et al. |
| 2010/0130522 A1 | 5/2010 | Jiang et al. |
| 2010/0152241 A1 | 6/2010 | Whitten |
| 2010/0273744 A1 | 10/2010 | Gore et al. |
| 2010/0286103 A1 | 11/2010 | Chen |
| 2010/0292252 A1 | 11/2010 | Chen |
| 2010/0311787 A1 | 12/2010 | Chen et al. |
| 2011/0015184 A1 | 1/2011 | Bohnert et al. |
| 2011/0052643 A1 | 3/2011 | Che et al. |
| 2011/0105447 A1 | 5/2011 | Muthuppalaniappan et al. |
| 2011/0112058 A1 | 5/2011 | Muthuppalaniappan et al. |
| 2011/0230536 A1 | 9/2011 | Whitten et al. |
| 2011/0263612 A1 | 10/2011 | Whitten et al. |
| 2011/0305709 A1 | 12/2011 | Braun et al. |
| 2012/0035237 A1 | 2/2012 | Coe et al. |
| 2012/0053210 A1 | 3/2012 | Whitten et al. |
| 2012/0316182 A1 | 12/2012 | Whitten et al. |
| 2012/0316185 A1 | 12/2012 | Beattie et al. |
| 2013/0252974 A1 | 9/2013 | Altenburger et al. |
| 2014/0256771 A1 | 9/2014 | Cao et al. |
| 2020/0101069 A1 | 4/2020 | Stauderman et al. |
| 2020/0253966 A1 | 8/2020 | Stauderman et al. |

FOREIGN PATENT DOCUMENTS

| | | |
|---|---|---|
| JP | 2003527324 A | 9/2003 |
| JP | 2006510737 A | 3/2006 |
| JP | 2011513332 A | 4/2011 |
| WO | WO-9806719 A1 | 2/1998 |
| WO | WO-9951580 A1 | 10/1999 |
| WO | WO-2004056774 A2 | 7/2004 |
| WO | WO-2005009539 A2 | 2/2005 |
| WO | WO-2005009954 A2 | 2/2005 |
| WO | WO-2006006569 A1 | 1/2006 |
| WO | WO-2006034402 A2 | 3/2006 |
| WO | WO-2006081389 A1 | 8/2006 |
| WO | WO-2006081391 A2 | 8/2006 |
| WO | WO-2006083477 A2 | 8/2006 |
| WO | WO-2006089177 A2 | 8/2006 |
| WO | WO-2007052123 A2 | 5/2007 |
| WO | WO-2007056341 A1 | 5/2007 |
| WO | WO-2007081804 A2 | 7/2007 |
| WO | WO-2007087429 A2 | 8/2007 |
| WO | WO-2007093542 A1 | 8/2007 |
| WO | WO-2007112093 A2 | 10/2007 |
| WO | WO-2007120600 A2 | 10/2007 |
| WO | WO-2008002576 A2 | 1/2008 |
| WO | WO-2008063504 A2 | 5/2008 |
| WO | WO-2009020642 A1 | 2/2009 |
| WO | WO-2009035818 A1 | 3/2009 |
| WO | WO-2010025295 A2 | 3/2010 |
| WO | WO-2010027875 A2 | 3/2010 |
| WO | WO-2010034011 A2 | 3/2010 |
| WO | WO-2010122089 A1 | 10/2010 |
| WO | WO-2011034962 A2 | 3/2011 |
| WO | WO-2011063277 A1 | 5/2011 |
| WO | WO-2011139489 A2 | 11/2011 |
| WO | WO-2011139765 A2 | 11/2011 |
| WO | WO-2012027710 A2 | 3/2012 |
| WO | WO-2012151355 A1 | 11/2012 |
| WO | WO-2012170931 A2 | 12/2012 |
| WO | WO-2012170951 A2 | 12/2012 |
| WO | WO-2013059666 A1 | 4/2013 |
| WO | WO-2013059677 A1 | 4/2013 |
| WO | WO-2013164769 A1 | 11/2013 |
| WO | WO-2014043715 A1 | 3/2014 |
| WO | WO-2014059333 A1 | 4/2014 |
| WO | WO-2016138472 A1 | 9/2016 |
| WO | WO-2017027400 A1 | 2/2017 |
| WO | WO-2018140796 A1 | 8/2018 |

OTHER PUBLICATIONS

Baba et al. Coupling of STIM1 to store-operated Ca2+ entry through its constitutive and inducible movement in the endoplasmic reticulum. PNAS USA 103:16704-16709 (2006).

Berridge. Inositol trisphosphate and calcium signalling. Nature 361:315-325 (1993).

Brayer et al. Alleles from chromosomes 1 and 3 of NOD mice combine to influence Sjögren's syndrome-like autoimmune exocrinopathy. J. Rheumatol. 27:1896-1904 (2000).

Chaplan et al. Quantitative assessment of tactile allodynia in the rat paw. J Neurosci Methods 53:55-63 (1994).

Cho. Recent Advances in Oral Prodrug Discovery. Annual Reports in Medicinal Chemistry 41:395-407 (2006).

Churchill et al. Imaging of intracellular calcium stores in single permeabilized lens cells. Am. J. Physiol. 276:C426-434 (1999).

Colitis. http://www.healthline.com/health/ulterative-colitis-take-control-can-it-be-cured? (3 pgs) (2014).

Dargie et al. Comparison of Ca2+ mobilizing activities of cyclic ADP-ribose and inositol trisphosphate. Cell Regul. 1:279-290 (1990).

Derler et al. The action of selective CRAC channel blockers is affected by the Orai pore geometry. Cell Calcium 53(2):139-151 (2013).

European Medicines Agency. Public summary of opinion on orphan designation N-(5-(6-chloro-2,2-difluorobenzo[d][1,3]dioxo1-5-yl)pyrazin-2-y1)-2-fluoro-6-methylbenzamide for the treatment of acute pancreatitis. Committee report [online]. (Dec. 13, 2016) [Retrieved on Feb. 26, 2018]. Retrieved from the Internet:<URL:http://www.ema.europa.eu/docs/en_GB/document_library/Orphan_designation/2016/12NVC500 217961.pdf> (5 pgs.).

Fagan et al. Regulation of the Ca2+-inhibitable adenylyl cyclase type VI by capacitative Ca2+ entry requires localization in cholesterol-rich domains. J Biol Chem 275(34):26530-26537 (Aug. 25, 2000).

Fedorak et al. A novel colon-specific steroid prodrug enhances sodium chloride absorption in rat colitis. Am. J. Physiol. 269:G210-218 (1995).

Feske et al. A Mutation in Orai1 Causes Immune Deficiency by Abrogating CRAC Channel Function. Nature 441:179-185 (2006).

Frick. The role of calcium in acute pancreatitis. Surgery 152(3 Suppl 1):S157-S163 (2012).

Funaba et al. Degranulation in RBL-2H3 cells: regulation by calmodulin pathway. Cell Biol Int 27:879-885 (2003).

Gerasimenko et al. Ca2+ release-activated Ca2+ channel blockade as a potential tool in antipancreatitis therapy. PNAS USA 110(32):13186-13191 (2013).

Gerasimenko et al. Inositol trisphosphate and cyclic ADP-ribose-mediated release of Ca2+ from single isolated pancreatic zymogen granules. Cell 84:473-480 (1996).

Gomez-Puerta et al. Tyrosine kinase inhibitors for the treatment of rheumatoid arthritis. Curr Top Med Chem. 13(6):760-773 (2013).

Gompertz et al. Bedside index for severity in acute pancreatitis (BISAP) score as predictor of clinical outcome in acute pancreatitis: retrospective review of 128 patients. Rev Med Chil 140(8):977-983 (2012).

Griffiths et al. Genetic analysis of collagen-induced arthritis in rats: a polygenic model for rheumatoid arthritis predicts a common framework of cross-species inflammatory/autoimmune disease loci. Immunol. Rev. 184:172-183 (2001).

Gromoda et al. Cyclic ADP-ribose and inositol 1,4,5-triphosphate mobilizes Ca2+ from distinct intracellular pools in permeabilized lacrimal acinar cells. FEBS Lett. 360:303-306 (1995).

Guse et al. Regulation of calcium signalling in T lymphocytes by the second messenger cyclic ADP-ribose. Nature 398:70-73 (1999).

(56) References Cited

OTHER PUBLICATIONS

Hochhaus et al. A selective HPLC/RIA for dexamethasone and its prodrug dexamethasone-21-sulphobenzoate sodium in biological fluids. Biomed. Chrom. 6:283-286 (1992).
Hofer et al. Free [Ca2+] dynamics measured in agonist-sensitive stores of single living intact cells: a new look at the refilling process. EMBO J. 17:1986-1995 (1998).
Huang et al. STIM1 carboxyl-terminus activates native SOC, Icrac and TRPC1 channels. Nature Cell Biology 8(9):1003-1010 (2006).
Humbles et al. The murine CCR3 receptor regulates both the role of eosinophils and mast cells in allergen-induced airway inflammation and hyperresponsiveness. PNAS USA 99:1479-1484 (2002).
Humphreys-Beher et al. New concepts for the development of autoimmune exocrinopathy derived from studies with the NOD mouse model. Arch. Oral Biol. 44( Suppl 1):S21-25 (1999).
Jefferson et al. Experimental mesangial proliferative glomerulonephritis (the anti-Thy-1.1 model). J. Nephrol. 12:297-307 (1999).
Karlsson et al. Pulmonary-Allergy, Dermatological, Gastrointestinal & Arthiritis Phosphodiesterase 4 Inhibitors for the treatment of asthma. Exp. Opin. Their Patents. 7(9):989-1003 (1997).
Larsen et al. Prodrug forms for the sulfonamide group. I. Evaluation of N-acyl derivatives, N-sulfonylamindes, N-sulfonylsulfilimines and sulfonylureas as possible prodrug derivatives. Int. J. Pharmaceutics 37:87-95 (1987).
Larsen et al. Prodrug forms for the sulfonamide group. II. water-soluble amino acid derivatives of N-methylsulfonylamindes as possible prodrug derivatives. Int'l J of Pharmaceutics 47:103-110 (1988).
Lewis. Calcium Signaling Mechanisms in T Lymphocytes. Annu Rev Immunol 19:497-521 (2001).
Liou et al. STIM is a Ca2+ sensor essential for Ca2+-store-depletion-triggered Ca2+ influx. Curr. Biol. 15(13):1235-1241 (2005).
Luik et al. The elementary unit of store-operated Ca2+ entry: local activation of CRAC channels by STIM1 at ER-plasma membrane junctions. J. Cell Biol. 174:815-825 (2006).
Luo et al. Upregulation of dorsal root ganglion (alpha)2(delta) calcium channel subunit and its correlation with allodynia in spinal nerve-injured rats. J. Neurosci 21:1868-1875 (2001).
Macian et al. Transcriptional mechanisms underlying lymphocyte tolerance. Cell 109(6):719-731 (Jun. 14, 2002).
Manji et al. STIM1: a novel phosphoprotein located at the cell surface. Biochim Biophys Acta. 1481(1):147-155 (2000).
McLeod et al. A glucocorticoid prodrug facilitates normal mucosal function in rat colitis without adrenal suppression. Gastroenterol 106:405-413 (1994).
Mercer et al. Large store-operated calcium selective currents due to co-expression of Orai1 or Orai2 with the intracellular calcium sensor, Stim1. JBC 281:24979-24990 (2006).
Millar et al. Functional expression of a cloned Drosophila muscarinic acetylcholine receptor in a stable Drosophila cell line. Exp. Biol. 198:1843-1850 (1995).
Miller et al. Histone deacetylase inhibitors. Med. Chem. 46(24):5097-5116 (2003).
Miyawaki et al. Fluorescent indicators for Ca2+ based on green fluorescent proteins and calmodulin. Nature 388(6645):882-887 (Aug. 28, 1997).
Multiple Sclerosis Prevention. Retrieved from http://www.webmd.com/multiple-sclerosis/tc/multiple-sclerosis-ms-prevention (3 pgs.) (2017).
Multiple Sclerosis Treatment. Retrieved from http://www.webmd.com/multiple-sclerosis/tc/multiple-sclerosis-ms-medications#1 (4 pgs) (2017).
Nogrady. Medicinal Chemistry A Biochemical Approach, Oxford University Press, New York, pp. 388-392 (1985).
Nunez et al. Cell proliferation depends on mitochondrial Ca2+ uptake: inhibition by salicylate. J Physiol. 571(Pt 1):57-73 (Feb. 15, 2006/ Epub Dec. 8, 2005).
Papachristou et al. Comparison of BISAP, Ranson's, APACHE-II, and CTSI scores in predicting organ failure, complications, and mortality in acute pancreatitis. Am J Gastroenterol. 105(2):435-441 (2010).
Parekh et al. Store Depletion and Calcium Influx. Physiol Rev 77(4):901-930 (1997).
Parekh et al. Store-Operated Calcium Channels. Physiol Rev 85:757-810 (2005).
Patani et al. Bioisosterism: A Rational Approach in Drug Design. Chem. Rev. 96:3147-3176 (1996).
Patterson et al. Phospholipase C-γ Is Required for Agonist-Induced Ca2+ Entry. Cell 111(4):529-541 (2002).
PCT/US2011/031992 International Search Report and Written Opinion dated Dec. 7, 2011.
PCT/US2016/019924 International Search Report and Written Opinion dated Jul. 8, 2016.
PCT/US2016/045846 International Search Report and Written Opinion dated Oct. 24, 2016.
PCT/US2018/015555 International Search Report and Written Opinion dated Apr. 4, 2018.
Petersen. Can specific calcium channel blockade be the basis for a drug-based treatment of acute pancreatitis? Expert Reviews 8(4):339-341 (2014).
Prakriya et al. Store-operated calcium channels: properties, functions and the search for a molecular mechanism. Molecular and Cellular Insights into Ion Channel Biology 32:121-140 (2004).
Putney et al. A model for receptor-regulated calcium entry. Cell Calcium. 7(1):1-12 (1986).
Putney et al. The signal for capacitative calcium entry. Cell 75(2):199-201 (1993).
Rao et al. Transcription factors of the NFAT family: regulation and function. Annu Rev Immunol. 15:707-747 (1997).
Roos et al. STIM1, an essential and conserved component of store-operated Ca2+ channel function. J Cell Biol 169(3):435-445 (2005).
Rooseboom et al. Enzyme-catalyzed activation of anticancer prodrugs. Pharmacological Reviews 56:53-102 (2004).
Rudensky et al. FOXP3 and NFAT: partners in tolerance. Cell 126(2):253-256 (2006).
Saulnier et al. An Efficient Method for the Synthesis of Guanidino Prodrugs. Bioorg Med Chem Lett 4(16):1985-1990 (1994).
Silverman. Chapter 8: Prodrugs and Drug Delivery Systems. The Organic Chemistry of Drug Design and Drug Action, Academic Press, Inc., San Diego (pp. 352-401) (1992).
Sinkula et al. Rationale for design of biologically reversible drug derivatives: prodrugs. J. Pharm. Sci. 64:181-210 (1975).
Spassova et al. STIM1 has a plasma membrane role in the activation of store-operated Ca(2+) channels. PNAS USA 103:4040-4045 (2006).
Stathopulos et al. Stored Ca2+ depletion-induced oligomerization of stromal interaction molecule 1 (STIM1) via the EF-SAM region: An initiation mechanism for capacitive Ca2+ entry. J. Biol. Chem. 281:35855-35862 (2006).
Streb et al. Release of Ca2+ from a nonmitochondrial intracellular store in pancreatic acinar cells by inositol-1,4,5-trisphosphate. Nature 306:67-69 (1983).
Takizawa et al. Caplus AN 2006:50793 (WO2006006569) (2 pgs) (2006).
Trevilyan et al. Potent inhibition of NFAT activation and T cell cytokine production by novel low molecular weight pyrazole compounds. J Biol Chem. 276(51):48118-48126 (2001).
U.S. Appl. No. 13/085,324 Office Action dated Feb. 8, 2013.
U.S. Appl. No. 13/969,401 Office Action dated Dec. 10, 2014.
U.S. Appl. No. 13/969,401 Office Action dated Jul. 8, 2014.
U.S. Appl. No. 13/969,401 Office Action dated Mar. 17, 2014.
U.S. Appl. No. 13/975,238 Office Action dated Jan. 27, 2014.
U.S. Appl. No. 13/975,238 Office Action dated Jun. 9, 2014.
U.S. Appl. No. 14/805,292 Office Action dated Aug. 21, 2017.
U.S. Appl. No. 14/805,292 Office Action dated Feb. 6, 2017.
U.S. Appl. No. 14/805,292 Office Action dated Mar. 30, 2018.
U.S. Appl. No. 14/805,292 Office Action dated Oct. 18, 2018.
U.S. Appl. No. 15/553,531 Office Action dated Apr. 6, 2020.
U.S. Appl. No. 15/553,531 Office Action dated Aug. 13, 2019.
U.S. Appl. No. 15/751,098 Office Action dated Nov. 26, 2018.

(56) References Cited

OTHER PUBLICATIONS

Vig et al. CRACM1 is a plasma membrane protein essential for store-operated Ca2+ entry. Science 312(5777):1220-1223 (2006).

Vig et al. CRACM1 Multimers Form the Ion-Selective Pore of the CRAC Channel. Current Biology 16:2073-2079 (2006).

Voronina et al. The role of Ca2+ influx in endocytic vacuole formation in pancreatic acinar cells. Biochemical J 465(3):405-412 (2015).

Wen et al. Orail inhibition prevents calcium toxicity and acute pancreatitis. Pancreatology 3.14 Supp 1:S100-S101 (2014).

Williams et al. Identification and characterization of the STIM (stromal interaction molecule) gene family: coding for a novel class of transmembrane proteins. Biochem. J. 357:673-685 (2001).

Winslow et al. Calcium Signalling in Lymphocytes. Current Opinion in Immunology 16:299-307 (2003).

Wu et al. Ca2+ store depletion causes STIM1 to accumulate in ER regions closely associated with the plasma membrane. J Cell Biol 174(6):803-813 (2006).

Wu et al. FOXP3 controls regulatory T cell function through cooperation with NFAT. Cell 126(2):375-387 (Jul. 28, 2006).

Wu et al. The early prediction of mortality in acute pancreatitis: a large population-based study. Gut 57(12):1698-1703 (2008).

Xu et al. Aggregation of STIM1 underneath the plasma membrane induces clustering of Orai1. Biochem. Biophys. Res. Commun. 350:969-976 (2006).

Yagodin et al. Functional characterization of thapsigargin and agonist-insensitive acidic Ca2+ stores in Drosophila melanogaster S2 cell lines. Cell Calcium 25:429-438 (1999).

Yagodin et al. Thapsigargin and receptor-mediated activation of Drosophila TRPL channels stably expressed in a Drosophila S2 cell line. Cell Calcium 23:219-228 (1998).

Yeromin et al. Molecular identification of the CRAC channel by altered ion selectivity in a mutant of Orai. Nature 443:226-229 (2006).

Yu et al. Rapid turnover of calcium in the endoplasmic reticulum during signaling. Studies with cameleon calcium indicators. J. Biol. Chem. 275:23648-23653 (2000).

Zhang et al. Genome Wide RNAi Screen of Ca2+ influx identifies Genes that Regulate Ca2+ Channel Activity. PNAS USA 103(4):9357-9362 (2006).

Zhang et al. STIM1 is a Ca2+ sensor that activates CRAC channels and migrates from the Ca2+ store to the plasma membrane. Nature 437(7060):902-905 (2005).

Co-pending U.S. Appl. No. 16/653,475, filed Oct. 15, 2019.

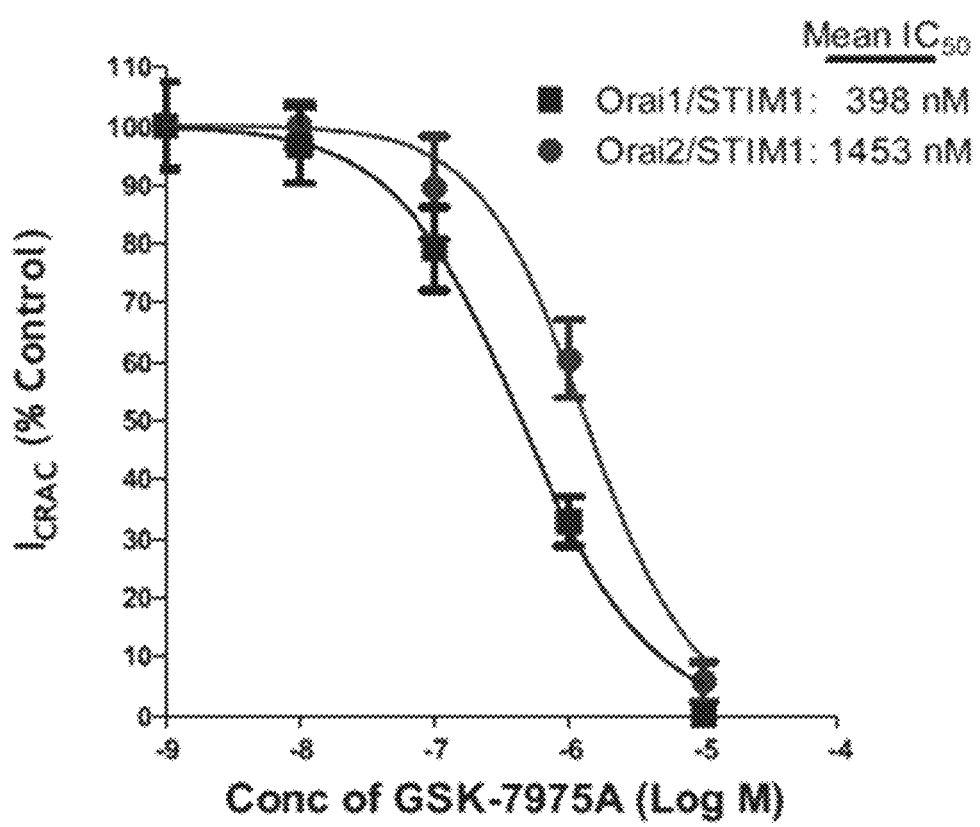

FIG. 7

| Group | Cytokine | Mean IC$_{50}$ (nM) Cpd. I (n=2) |
|---|---|---|
| Cytokines with receptors expressed in acinar cells | IFNγ | 138 |
| | IL-4 | 879 |
| | IL-6 | 135 |
| Cytokines expressed in acinar cells | IL-1β | 240 |
| | IL-6 | 135 |
| | IL-10 | 303 |
| | TNFα | 225 |
| Cytokines important in T cell function | IL-2 | 59 |
| | IL-17 | 120 |

PYRAZINE-CONTAINING COMPOUND

CROSS-REFERENCE

This application is a continuation of U.S. application Ser. No. 15/553,531, filed Aug. 24, 2017, which was filed pursuant to 35 U.S.C. § 371 as a U.S. National Phase Application of International Application No. PCT/US2016/019924, filed Feb. 26, 2016, which claims the benefit of U.S. Provisional Application No. 62/126,386, filed Feb. 27, 2015, each of which are herein incorporated by reference in their entirety.

BACKGROUND

Acute pancreatitis is the number one cause of gastrointestinal hospitalizations and a major cost burden in the United States. Acute pancreatitis demonstrates a 10-25% mortality rate in severe patients, and a 3-5% mortality rate overall. There is as yet no disease modifying therapy available for sufferers of the condition.

SUMMARY OF THE INVENTION

Provided herein are embodiments related to methods of ameliorating the symptoms of pancreatitis in a mammal such as a person. In other embodiments, methods of ameliorating the symptoms of a viral infection in a mammal such as a person are described herein. In further embodiments, methods of ameliorating the symptoms of T helper 17 cell (Th17)-induced inflammation and autoimmune diseases are described herein.

In some embodiments, the methods comprise the steps of identifying a person in need of amelioration of symptoms of pancreatitis, and administering an intracellular Calcium signaling inhibitor to said person at a dose sufficient to ameliorate said symptoms. In other embodiments, the methods comprise the steps of identifying a person in need of amelioration of symptoms of a viral disease, and administering an intracellular Calcium signaling inhibitor to said person a dose sufficient to ameliorate said symptoms. In further embodiments, the methods comprise the steps of identifying a person in need of amelioration of symptoms of Th17-induced diseases, and administering an intracellular Calcium signaling inhibitor to said person a dose sufficient to ameliorate said symptoms. In some aspects the intracellular Calcium signaling inhibitor is a SOC channel inhibitor. In some aspects the intracellular Calcium signaling inhibitor is a CRAC channel inhibitor. In some aspects the intracellular Calcium signaling inhibitor inhibits a channel comprising a STIM1 protein. In some aspects the intracellular Calcium signaling inhibitor inhibits a channel comprising Orai1 protein. In some aspects the intracellular Calcium signaling inhibits a channel comprising Orai2 protein.

In some aspects the intracellular Calcium signaling inhibitor is a compound having a structure of:

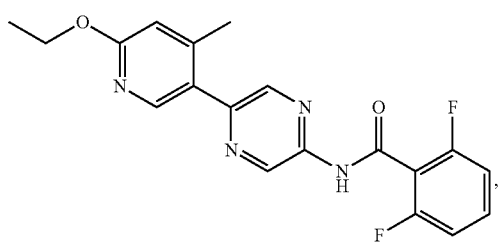

-continued

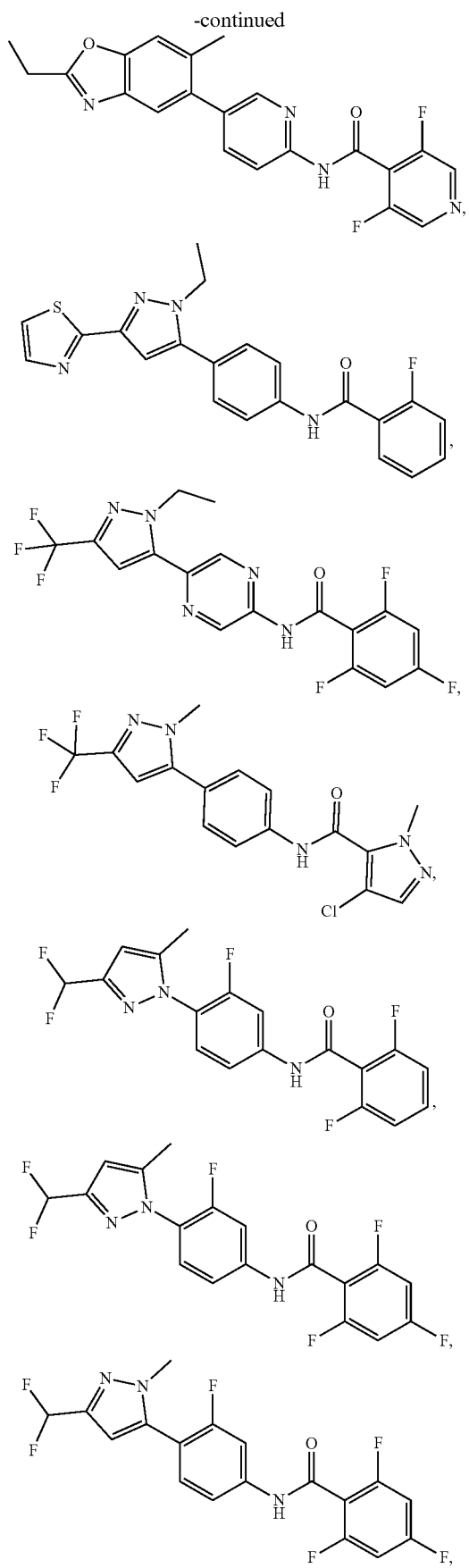

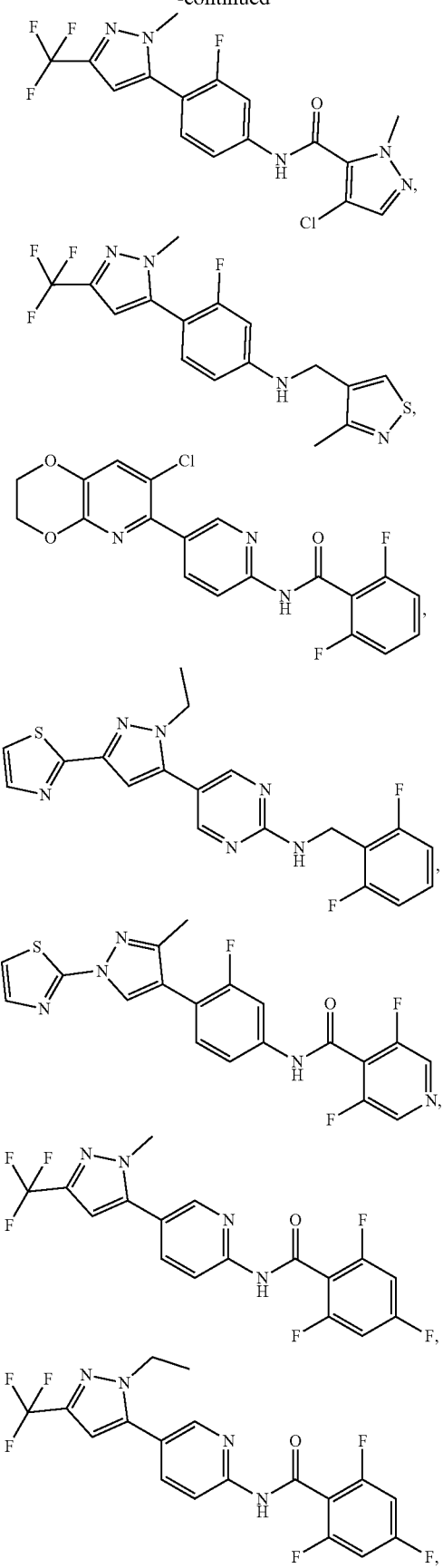
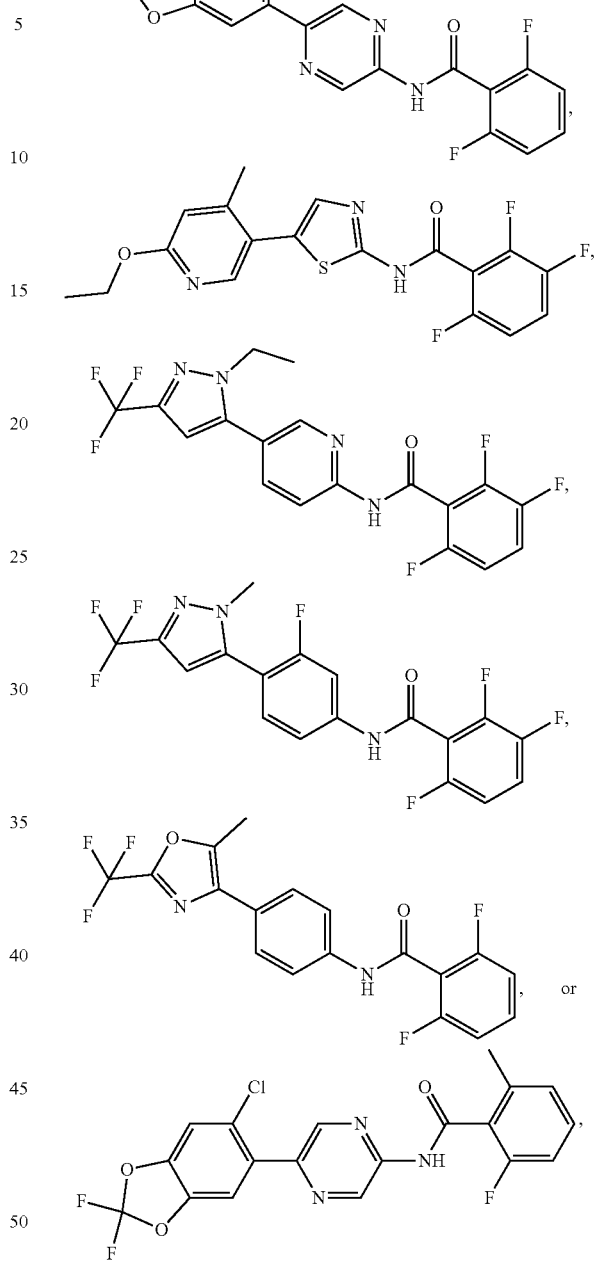

(collectively, "Compound A"), or a pharmaceutically acceptable salt, pharmaceutically acceptable solvate, or pharmaceutically acceptable prodrug thereof. In some embodiments the intracellular Calcium signaling inhibitor is a compound having a structure from the group of Compound A or a nanoparticle formulation thereof, including a nanoparticle suspension or emulsion.

In some aspects the intracellular Calcium signaling inhibitor is a compound of N-(5-(6-chloro-2,2-difluorobenzo[d][1,3]dioxol-5-yl)pyrazin-2-yl)-2-fluoro-6-methylbenzamide. In some aspects the intracellular Calcium signaling inhibitor is a compound of N-(5-(6-chloro-2,2-difluorobenzo[d][1,3]dioxol-5-yl)pyrazin-2-yl)-2-fluoro-6-methylbenzamide or a pharmaceutically acceptable salt, pharmaceutically acceptable solvate, or pharmaceutically acceptable prodrug thereof. In some aspects the intracellular Calcium signaling inhibitor is chosen from among the compounds, N-(5-(6-ethoxy-4-methylpyridin-3-yl)pyrazin-2-yl)-2,6-difluorobenzamide, N-(5-(2-ethyl-6-methylbenzo[d]oxazol-5-yl)pyridin-2-yl)-3,5-difluoroisonicotinamide, N-(4-(1-ethyl-3-(thiazol-2-yl)-1H-pyrazol-5-yl)phenyl)-2-fluorobenzamide, N-(5-(1-ethyl-3-(triflouromethyl)-1H-pyrazol-5-yl)pyrazin-2-yl)-2,4,6-trifluorobenzamide, 4-chloro-1-methyl-N-(4-(1-methyl-3-(trifluoromethyl)-1H-pyrazol-5-yl)phenyl)-1H-pyrazole-5-carboxamide, N-(4-(3-(difluoromethyl)-5-methyl-1H-pyrazol-1-yl)-3-fluorophenyl)-2,6-difluorobenzamide, N-(4-(3-(difluoromethyl)-5-methyl-1H-pyrazol-1-yl)-3-fluorophenyl)-2,4,6-trifluorobenzamide, N-(4-(3-(difluoromethyl)-1-methyl-1H-pyrazol-5-yl)-3-fluorophenyl)-2,4,6-trifluorobenzamide, 4-chloro-N-(3-fluoro-4-(1-methyl-3-(trifluoromethyl)-1H-pyrazol-5-yl)phenyl)-1-methyl-1H-pyrazole-5-carboxamide, 3-fluoro-4-(1-methyl-3-(trifluoromethyl)-1H-pyrazol-5-yl)-N-((3-methylisothiazol-4-yl)methyl)aniline, N-(5-(7-chloro-2,3-dihydro-[1,4]dioxino[2,3-b]pyridin-6-yl)pyridin-2-yl)-2,6-difluorobenzamide, N-(2,6-difluorobenzyl)-5-(1-ethyl-3-(thiazol-2-yl)-1H-pyrazol-5-yl)pyrimidin-2-amine, 3,5-difluoro-N-(3-fluoro-4-(3-methyl-1-(thiazol-2-yl)-1H-pyrazol-4-yl)phenyl)isonicotinamide, 5-(1-methyl-3-(trifluoromethyl)-1H-pyrazol-5-yl)-N-(2,4,6-trifluorobenzyl)pyridin-2-amine, N-(5-(1-ethyl-3-(trifluoromethyl)-1H-pyrazol-5-yl)pyridin-2-yl)-2,4,6-trifluorobenzamide, N-(5-(5-chloro-2-methylbenzo[d]oxazol-6-yl)pyrazin-2-yl)-2,6-difluorobenzamide, N-(5-(6-ethoxy-4-methylpyridin-3-yl)thiazol-2-yl)-2,3,6-trifluorobenzamide, N-(5-(1-ethyl-3-(trifluoromethyl)-1H-pyrazol-5-yl)pyridin-2-yl)-2,3,6-trifluorobenzamide, 2,3,6-trifluoro-N-(3-fluoro-4-(1-methyl-3-(trifluoromethyl)-1H-pyrazol-5-yl)phenyl)benzamide, 2,6-difluoro-N-(4-(5-methyl-2-(trifluoromethyl)oxazol-4-yl)phenyl)benzamide, or N-(5-(6-chloro-2,2-difluorobenzo[d][1,3]dioxol-5-yl)pyrazin-2-yl)-2-fluoro-6-methylbenzamide, (collectively, "Compound A"), or a pharmaceutically acceptable salt, pharmaceutically acceptable solvate, or pharmaceutically acceptable prodrug thereof. In some aspects the symptoms are acute pancreatitis symptoms. In some aspects the symptoms comprise at least one of inflammation and edema of the pancreas, upper abdominal pain radiating to the back, left upper quadrant pain radiating to the back, nausea, vomiting, vomiting that is worsened with eating, elevated heart rate, tachycardia, elevated respiratory rate, elevated blood pressure, decreased blood pressure, dehydration, abdominal tenderness, fever, chills, peritonitis, hemodynamic instability, and reflex bowel paralysis. In some aspects the symptoms are severe acute pancreatitis symptoms. In some aspects the symptoms comprise at least one of pancreatic necrosis and injury to extra-pancreatic organs. In some aspects the symptoms are chronic pancreatitis symptoms. In some aspects the symptoms comprise at least one of persistent abdominal pain, digestive defects, malabsorption of fats, pain during food uptake, weight loss, elevation of serum amylase activity, elevation of serum lipase activity, elevation of a CRP inflammatory marker, impairment of bicarbonate production, elevated fecal elastase levels, elevated serum trypsinogen levels, pancreatic calcification, elevated serum bilirubin levels, and elevated alkaline phosphatase levels. In some aspects the symptoms comprise at least one of elevated ESR levels, elevated IgG4 levels, elevated rheumatoid factor, presence of ANA antibody, presence of antismooth muscle antibody, assay of any of which may indicate chronic pancreatitis in a person In some aspects the symptoms comprise at least one of steatorrhea, Sudan chemical staining of feces or fecal fat excretion of 7 grams or more over a 24 hr period on a 100 g fat diet, and fecal elastase in a stool sample at a value of less than 200 µg/g. In some aspects the symptoms comprise at least one of abdominal pain, increased blood amylase levels, increased blood lipase levels, enlarged pancreas, nausea, vomiting, internal bleeding, bowel paralysis, fever, jaundice, weight loss, and elevated heart rate. In some aspects the symptoms comprise elevated serum levels of amylase. In some aspects the symptoms comprise elevated serum levels of lipase. In some aspects the symptoms comprise findings of necrosis by computed tomography (CT) scan. In some aspects the symptoms comprise premature digestive enzyme activation. In some aspects the premature digestive enzyme activation occurs in a pancreas of said person. In some aspects the enzyme comprises trypsin.

Some embodiments relate to methods of preventing or ameliorating a symptom associated with a pancreatic disorder in a person at risk of a pancreatic disorder. In some embodiments the method comprises the steps of identifying a person having a risk factor associated with a pancreatic disorder; and administering an intracellular Calcium signaling inhibitor at a dose sufficient to prevent or ameliorate said side effect. In some aspects the intracellular Calcium inhibiter is a SOC channel inhibitor. In some aspects the intracellular Calcium inhibiter is a CRAC channel inhibitor. In some aspects the intracellular Calcium signaling inhibitor is a compound having the structure from the group of Compound A, or a pharmaceutically acceptable salt, pharmaceutically acceptable solvate, or pharmaceutically acceptable prodrug thereof. In some aspects the intracellular Calcium signaling inhibitor is a compound of, N-(5-(6-chloro-2,2-difluorobenzo[d][1,3]dioxol-5-yl)pyrazin-2-yl)-2-fluoro-6-methylbenzamide. In some aspects the pancreatic disorder comprises an acute pancreatitis symptom. In some aspects the pancreatic disorder comprises a chronic pancreatitis symptom. In some aspects the person has pancreatitis as a result of being subjected to a drug regimen comprising administration of at least one of a steroid such as a corticosteroid, prednisolone, an HIV drug, didanosine, pentamidine, a diuretic, valproic acid, L-asparaginase, azathioprine, estrogen, a statin such as a cholesterol-lowering statin, an antihyperglycemic agent, metformin, a glipin such as vildagliptin and sitagliptin, an atypical antipsychotic, clozapine, risperidone, and olanzapine. In some aspects the person is identified as harboring an inherited form of pancreatitis. In some aspects the person harbors a mutant allele of at least one of trypsin1, encoding trypsinogen, SPINK1, encoding a trypsin inhibitor, and cystic fibrosis transmembrane conductance regulator. In some aspects the person has pancreatitis as a result of suffering at least one of high blood calcium, hypothermia, endoscopic retrograde cholangiopancreatography (ERCP), pancreas divisum, a congenital malformation of the pancreas, diabetes mellitus type 2, pancreatic cancer, pancreatic duct stones, vasculitis, inflammation of the small blood vessels in the pancreas, coxsackievirus infection, and porphyra, such as acute intermittent porphyria and erythropoietic protoporphyria. In some aspects the bodily health condition of said person has been impacted at least one of a gall stone, ethanol poisoning, alcoholism, trauma, mumps, an autoimmune disorder, a scorpion sting, hyperlipidaemia, hypothermia, hyperparathyroidism, and endoscopic retrograde cholangiopancreatography, azathioprine, and valproic acid. In some aspects the bodily health condition of said person has been impacted by at least one of a Coxsackie virus, a Cytomegalovirus, a Hepatitis B virus, a Herpes simplex virus, Mumps, a Varicella-zoster virus, a *Legionella* bacterium, a *Leptospira* bacterium, a *Mycoplasma* bacterium, a *Salmonella* bacterium, an *Aspergillus* fungus, an *Ascaris* parasite, a *Cryptosporidium* cell and a *Toxoplasma* cell.

Some embodiments relate to methods of preventing or ameliorating a symptom associated with a viral disease in a person at risk of a viral disease. In some embodiments the method comprises the steps of: identifying a person having a risk factor associated with a viral disease; and administering an intracellular Calcium signaling inhibitor at a dose sufficient to prevent or ameliorate said side effect. Some embodiments relate to a composition for use of ameliorating the symptoms of viral disease in a person comprising the steps of identifying a person in need of amelioration of symptoms of viral disease, and administering an intracellular Calcium signaling inhibitor to said person at a dose sufficient to ameliorate said symptoms. In some aspects the intracellular Calcium signaling inhibitor is a CRAC channel inhibitor. In some aspects the intracellular Calcium signaling inhibitor inhibits a channel comprising a STIM1 protein. In some aspects the intracellular Calcium signaling inhibitor inhibits a channel comprising Orai1 protein. In some aspects the intracellular Calcium signaling inhibits a channel comprising Orai2 protein. In some aspects the intracellular Calcium signaling inhibitor is a compound having the structure from the group of Compound A, or a pharmaceutically acceptable salt, pharmaceutically acceptable solvate, or pharmaceutically acceptable prodrug thereof. In some aspects the intracellular Calcium signaling inhibitor is a compound of, N-(5-(6-chloro-2,2-difluorobenzo[d][1,3]dioxol-5-yl)pyrazin-2-yl)-2-fluoro-6-methylbenzamide. In some aspects the intracellular Calcium signaling inhibitor is a compound of N-(5-(6-chloro-2,2-difluorobenzo[d][1,3]dioxol-5-yl)pyrazin-2-yl)-2-fluoro-6-methylbenzamide or a pharmaceutically acceptable salt, pharmaceutically acceptable solvate, or pharmaceutically acceptable prodrug thereof. In some aspects the intracellular Calcium signaling inhibitor blocks budding of the viral disease. In some aspects, the viral disease is a hemorrhagic fever virus. In further aspects, the hemorrhagic fever virus is an arenavirus, a filovirus, a bunyavirus, a flavivirus, a rhabdovirus, or combinations thereof. In even further aspects, the hemorrhagic fever virus is Ebola virus, Marburg virus, Lassa virus, Junin virus, Rotavirus, West Nile virus, Zika virus, Coxsackievirus, Hepatitis B virus, Epstein Barr virus, dengue virus, or Rift Valley virus. In some aspects, the symptoms are fever or bleeding diathesis. In further aspects, the symptoms of a viral disease are at least one of flushing of the face, flushing of the chest, petechiae, capillary leak, bleeding, swelling, edema, hypotension, shock, malaise, muscle pain, headache, vomiting, diarrhea, or combinations thereof.

Some embodiments relate to methods of preventing or ameliorating a symptom associated with a Th17-induced disease in a person at risk of a Th17-induced disease. In some embodiments the method comprises the steps of: identifying a person having a risk factor associated with a Th17-induced disease; and administering an intracellular Calcium signaling inhibitor at a dose sufficient to prevent or ameliorate said side effect. Some embodiments relate to a composition for use of ameliorating the symptoms of Th17-induced disease in a person comprising the steps of identifying a person in need of amelioration of symptoms of pancreatitis, and administering an intracellular Calcium signaling inhibitor to said person at a dose sufficient to ameliorate said symptoms. In some aspects the intracellular Calcium signaling inhibitor is a CRAC channel inhibitor. In some aspects the intracellular Calcium signaling inhibitor inhibits a channel comprising a STIM1 protein. In some aspects the intracellular Calcium signaling inhibitor inhibits a channel comprising Orai1 protein. In some aspects the intracellular Calcium signaling inhibits a channel comprising Orai2 protein. In some aspects the intracellular Calcium signaling inhibitor is a compound having the structure from the group of Compound A, or a pharmaceutically acceptable salt, pharmaceutically acceptable solvate, or pharmaceutically acceptable prodrug thereof. In some aspects the intracellular Calcium signaling inhibitor is a compound of, N-(5-(6-chloro-2,2-difluorobenzo[d][1,3]dioxol-5-yl)pyrazin-2-yl)-2-fluoro-6-methylbenzamide. In some aspects the intracellular Calcium signaling inhibitor is a compound of N-(5-(6-chloro-2,2-difluorobenzo[d][1,3]dioxol-5-yl)pyrazin-2-yl)-2-fluoro-6-methylbenzamide or a pharmaceutically acceptable salt, pharmaceutically acceptable solvate, or pharmaceutically acceptable prodrug thereof. In some aspects the intracellular Calcium signaling inhibitor blocks differentiation of Th17 cells. In some aspects the Th17-induced disease is a chronic inflammatory disease. In further aspects, the chronic inflammatory disease is hay fever, periodontitis, atherosclerosis, rheumatoid arthritis, or cancer. In other aspects the Th17-induced disease is an autoimmune disease. In further aspects, the autoimmune disease is rheumatoid arthritis, lupus, celiac disease, psoriasis, Sjorgen's syndrome, polymyalgia rheumatica, multiple sclerosis, ankylosing spondylitis, type 1 diabetes, alopecia areata, vasculitis, or temporal arteritis. In some aspects, the symptoms of Th17-induced diseases are at least one of localized reddening, swelling, heat, pain, stiffness, fever, chills, fatigue, headache, or appetite loss. In some aspects, the symptoms occur on the body of the person comprising the torso, arms, hands, fingers, legs, feet, toes, head, neck, bones, joints, throat, sinuses, eyes, or combinations thereof.

Some embodiments relate to a composition comprising an intracellular Calcium signaling inhibitor and at least one drug associated with a negative impact on pancreatic activity. In some aspects the drug is selected from the list consisting of: a steroid such as a corticosteroid, prednisolone, an HIV drug, didanosine, pentamidine, a diuretic, valproic acid, L-asparaginase, azathioprine, estrogen, a statin such as a cholesterol-lowering statin, an antihyperglycemic agent, metformin, a glipin such as vildagliptin and sitagliptin, an atypical antipsychotic, clozapine, risperidone, and olanzapine, azathioprine, and valproic acid. In some aspects the intracellular Calcium signaling inhibitor is an SOC inhibitor. In some aspects the intracellular Calcium signaling inhibitor is a CRAC inhibitor. In some aspects the intracellular Calcium signaling inhibitor is a compound having the structure from the group of Compound A, or a pharmaceutically acceptable salt, pharmaceutically acceptable solvate, or pharmaceutically acceptable prodrug thereof. In some aspects the intracellular Calcium signaling inhibitor is a compound of, N-(5-(6-chloro-2,2-difluorobenzo[d][1,3]dioxol-5-yl)pyrazin-2-yl)-2-fluoro-6-methylbenzamide. In some aspects the intracellular Calcium signaling inhibitor is a compound of N-(5-(6-chloro-2,2-difluorobenzo[d][1,3]dioxol-5-yl)pyrazin-2-yl)-2-fluoro-6-methylbenzamide or a pharmaceutically acceptable salt, pharmaceutically acceptable solvate, or pharmaceutically acceptable prodrug thereof.

Some aspects relate to a dosing regimen comprising administration to an individual of a drug associated with a negative impact on pancreatic activity, and administration of an intracellular Calcium signaling inhibitor. In some aspects the drug is selected from the list consisting of: a steroid such as a corticosteroid, prednisolone, an HIV drug, didanosine, pentamidine, a diuretic, valproic acid, L-asparaginase, azathioprine, estrogen, a statin such as a cholesterol-lowering statin, an antihyperglycemic agent, metformin, a glipin such as vildagliptin and sitagliptin, an atypical antipsychotic, clozapine, risperidone, and olanzapine, azathioprine, and valproic acid. In some aspects the intracellular Calcium signaling inhibitor is an SOC inhibitor. In some aspects the intracellular Calcium signaling inhibitor is a CRAC inhibitor. In some aspects the intracellular Calcium signaling inhibitor is a compound having the structure from the group of Compound A, or a pharmaceutically acceptable salt, pharmaceutically acceptable solvate, or pharmaceutically acceptable prodrug thereof. In some aspects the intracellular Calcium signaling inhibitor is a compound of, N-(5-(6-chloro-2,2-difluorobenzo[d][1,3]dioxol-5-yl)pyrazin-2-yl)-2-fluoro-6-methylbenzamide. In some aspects the intracellular Calcium signaling inhibitor is a compound of N-(5-(6-chloro-2,2-difluorobenzo[d][1,3]dioxol-5-yl)pyrazin-2-yl)-2-fluoro-6-methylbenzamide or a pharmaceutically acceptable salt, pharmaceutically acceptable solvate, or pharmaceutically acceptable prodrug thereof.

Some embodiments relate to a composition for use of ameliorating the symptoms of pancreatitis in a person comprising the steps of identifying a person in need of amelioration of symptoms of pancreatitis, and administering an intracellular Calcium signaling inhibitor to said person at a dose sufficient to ameliorate said symptoms. In some aspects the intracellular Calcium signaling inhibitor is a SOC channel inhibitor. In some aspects the intracellular Calcium signaling inhibitor is a CRAC channel inhibitor. In some aspects the intracellular Calcium signaling inhibitor inhibits a channel comprising a STIM1 protein. In some aspects the intracellular Calcium signaling inhibitor inhibits a channel comprising Orai1 protein. In some aspects the intracellular Calcium signaling inhibits a channel comprising Orai2 protein. In some aspects the intracellular Calcium signaling inhibitor is a compound having the structure from the group of Compound A, or a pharmaceutically acceptable salt, pharmaceutically acceptable solvate, or pharmaceutically acceptable prodrug thereof. In some aspects the intracellular Calcium signaling inhibitor is a compound of, N-(5-(6-chloro-2,2-difluorobenzo[d][1,3]dioxol-5-yl)pyrazin-2-yl)-2-fluoro-6-methylbenzamide. In some aspects the intracellular Calcium signaling inhibitor is a compound of N-(5-(6-chloro-2,2-difluorobenzo[d][1,3]dioxol-5-yl)pyrazin-2-yl)-2-fluoro-6-methylbenzamide or a pharmaceutically acceptable salt, pharmaceutically acceptable solvate, or pharmaceutically acceptable prodrug thereof. In some aspects the composition further comprises a painkiller medication. In some aspects the painkiller medication comprises an opiate. In some aspects the painkiller medication comprises morphine. In some aspects the symptoms are acute pancreatitis symptoms. In some aspects the symptoms comprise at least one of inflammation and edema of the pancreas, upper abdominal pain radiating to the back, left upper quadrant pain radiating to the back, nausea, vomiting, vomiting that is worsened with eating, elevated heart rate, tachycardia, elevated respiratory rate, elevated blood pressure, decreased blood pressure, dehydration, abdominal tenderness, fever, chills, peritonitis, hemodynamic instability, and reflex bowel paralysis. In some aspects the symptoms are severe pancreatitis symptoms. In some aspects the symptoms comprise at least one of pancreatic necrosis and injury to extra-pancreatic organs. In some aspects the symptoms are chronic pancreatitis symptoms. In some aspects the symptoms comprise at least one of persistent abdominal pain, digestive defects, malabsorption of fats, pain during food uptake, weight loss, elevation of serum amylase activity, elevation of serum lipase activity, elevation of a CRP inflammatory marker, impairment of bicarbonate production, elevated fecal elastase levels, elevated serum trypsinogen levels, pancreatic calcification, elevated serum bilirubin levels, and elevated alkaline phosphatase levels. In some aspects the symptoms comprise at least one of elevated ESR levels, elevated IgG4 levels, elevated rheumatoid factor, presence of ANA antibody, presence of antismooth muscle antibody, assay of any of which may indicate chronic pancreatitis in a person. In some aspects the symptoms comprise at least one of steatorrhea, Sudan chemical staining of feces or fecal fat excretion of 7 grams or more over a 24 hr period on a 100 g fat diet, and fecal elastase in a stool sample at a value of less than 200 µg/g. In some aspects the symptoms comprise at least one of abdominal pain, increased blood amylase levels, increased blood lipase levels, enlarged pancreas, nausea, vomiting, internal bleeding, bowel paralysis, fever, jaundice, weight loss, and elevated heart rate. In some aspects the symptoms comprise premature digestive enzyme activation. In some aspects the premature digestive enzyme activation occurs in a pancreas of said person. In some aspects the enzyme comprises trypsin.

Some aspects relate to a composition for use of preventing or ameliorating a symptom associated with a pancreatic disorder in a person at risk of a pancreatic disorder, comprising the steps of: identifying a person having a risk factor associated with a pancreatic disorder; and administering an intracellular Calcium signaling inhibitor at a dose sufficient to prevent or ameliorate said side effect. In some aspects the intracellular Calcium inhibiter is a SOC channel inhibitor. In some aspects the intracellular Calcium inhibiter is a CRAC channel inhibitor. In some aspects the intracellular Calcium signaling inhibitor is a compound having the structure from the group of Compound A, or a pharmaceutically acceptable salt, pharmaceutically acceptable solvate, or pharmaceutically acceptable prodrug thereof. In some aspects the intracellular Calcium signaling inhibitor is a compound of, N-(5-(6-chloro-2,2-difluorobenzo[d][1,3]dioxol-5-yl)pyrazin-2-yl)-2-fluoro-6-methylbenzamide. In some aspects the intracellular Calcium signaling inhibitor is a compound of N-(5-(6-chloro-2,2-difluorobenzo[d][1,3]dioxol-5-yl)pyrazin-2-yl)-2-fluoro-6-methylbenzamide or a pharmaceutically acceptable salt, pharmaceutically acceptable solvate, or pharmaceutically acceptable prodrug thereof. In some aspects the pancreatic disorder comprises an acute pancreatitis symptom. In some aspects the pancreatic disorder comprises a chronic pancreatitis symptom. In some aspects the person is subjected to a drug regimen comprising administration of at least one of a steroid such as a corticosteroid, prednisolone, an HIV drug, didanosine, pentamidine, a diuretic, valproic acid, L-asparaginase, azathioprine, estrogen, a statin such as a cholesterol-lowering statin, an antihyperglycemic agent, metformin, a glipin such as vildagliptin and sitagliptin, an atypical antipsychotic, clozapine, risperidone, and olanzapine. In some aspects the person is identified as harboring an inherited form of pancreatitis. In some aspects the person harbors a mutant allele of at least one of trypsin, encoding trypsinogen, SPINK1, encoding a trypsin inhibitor, and cystic fibrosis transmembrane conductance regulator. In some aspects the person has suffered at least one of high blood calcium, hypothermia, endoscopic retrograde cholangiopancreatography (ERCP), pancreas divisum, a congenital malformation of the pancreas, diabetes mellitus type 2, pancreatic cancer, pancreatic duct stones, vasculitis, inflammation of the small blood vessels in the pancreas, coxsackie virus infection, and porphyra, such as acute intermittent porphyria and erythropoietic protoporphyria. In some aspects the bodily health condition of said person has been impacted at least one of a gall stone, ethanol poisoning, alcoholism, trauma, mumps, an autoimmune disorder, a scorpion sting, hyperlipidaemia, hypothermia, hyperparathyroidism, and endoscopic retrograde cholangiopancreatography, azathioprine, and valproic acid. In some aspects the bodily health condition of said person has been impacted by at least one of a Cytomegalovirus, a Hepatitis B virus, a Herpes simplex virus, Mumps, a Varicella-zoster virus, a *Legionella* bacterium, a *Leptospira* bacterium, a *Mycoplasma* bacterium, a *Salmonella* bacterium, an *Aspergillus* fungus, an *Ascaris* parasite, a *Cryptosporidium* cell and a *Toxoplasma* cell.

INCORPORATION BY REFERENCE

All publications, patents, and patent applications mentioned in this specification are herein incorporated by reference to the same extent as if each individual publication, patent, or patent application was specifically and individually indicated to be incorporated by reference.

In particular, PCT Publication No. WO 2011/139489 A2, published Nov. 10, 2011, is hereby incorporated by reference in its entirety; PCT Publication No. WO 2009/035818, published Mar. 19, 2009, is hereby incorporated by reference in its entirety; PCT Publication No. WO 2010/025295, published Jun. 17, 2010, is hereby incorporated by reference in its entirety; PCT Publication No. WO 2010/027875, published Jun. 10, 2010, is hereby incorporated by reference in its entirety; PCT Publication No. WO 2011/034962, published Jul. 28, 2011, is hereby incorporated by reference in its entirety; PCT Publication No. WO 2011/139489, published Jan. 26, 2012, is hereby incorporated by reference in its entirety; PCT Publication No. WO 2011/139765 published Mar. 8, 2012, is hereby incorporated by reference in its entirety; PCT Publication No. WO 2012/027710, published May 18, 2012, is hereby incorporated by reference in its entirety; PCT Publication No. WO 2012/170931, published Feb. 21, 2013 is hereby incorporated by reference in its entirety; PCT Publication No. WO 2012/170951, published Apr. 25, 2013, is hereby incorporated by reference in its entirety; PCT Publication No. WO 2013/059666, published Apr. 25, 2013, is hereby incorporated by reference in its entirety; PCT Publication No. WO 2013/059677, published Apr. 25, 2013, is hereby incorporated by reference in its entirety; PCT Publication No. WO 2014/043715, published Mar. 20, 2014, is hereby incorporated by reference in its entirety; and PCT Publication No. WO 2014/059333, published Apr. 17, 2014, is hereby incorporated by reference in its entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3B shows an $IC_{50}$ determination for 2,6-Difluoro-N-(1-(4-hydroxy-2-(trifluoromethyl)benzyl)-1H-pyrazol-3-yl)benzamide ("GSK-7975A").

FIG. 7 shows $IC_{50}$ values for Compound I against a number of cytokines.

DETAILED DESCRIPTION OF THE INVENTION

Figure 1A:
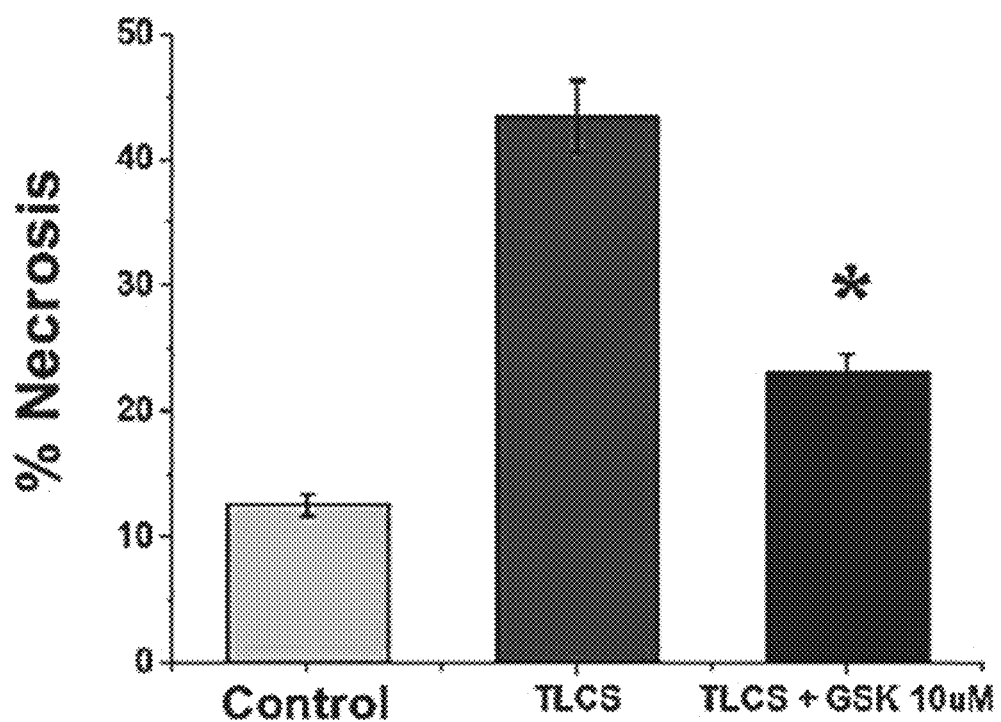
FIG. 1A shows mouse Acinar cell necrosis upon treatment with TLCS.

Methods and compositions disclosed herein are used for modulating intracellular calcium to ameliorate or prevent symptoms of pancreatitis. In some aspects, the pancreatitis is acute pancreatitis. In some aspects the pancreatitis is chronic pancreatitis. In some embodiments, methods and compositions disclosed herein are used for modulating intracellular calcium to ameliorate or prevent symptoms of a viral disease. In some aspects the viral disease is a hemorrhagic fever virus. In some aspects, the hemorrhagic fever virus is an arenavirus, a filovirus, a bunyavirus, a flavivirus, a rhabdovirus, or combinations thereof. Hemorrhagic fever viruses include, by way of non-limiting examples, Ebola virus, Marburg virus, Lassa virus, Junin virus, Rotavirus. West Nile virus, Zika virus, Coxsackievirus. Hepatitis B virus, Epstein Barr virus, etc. In further embodiments, methods and compositions disclosed herein are used for modulating intracellular calcium to ameliorate or prevent symptoms of Th17-induced diseases. In some aspects, the Th17-induced disease is an inflammatory disease. In further aspects, the Th17-induced disease is an autoimmune disorder. In some aspects, compounds provided herein modulate SOC channel activity. In some aspects, methods and compounds provided herein modulate CRAC channel activity. In another aspect, compounds provided herein modulate STIM protein activity. In another aspect, methods and compounds provided herein modulate Orai protein activity. In another aspect, methods and compounds provided herein modulate the functional interactions of STIM proteins with Orai proteins. In another aspect, methods and compounds provided herein reduce the number of functional SOC channels. In another aspect, methods and compounds provided herein reduce the number of functional CRAC channels. In some aspects, methods and compounds described herein are SOC channel blockers. In some aspects, methods and compounds described herein are CRAC channel blockers or CRAC channel modulators.

Calcium plays a vital role in cell function and survival. For example, calcium is a key element in the transduction of signals into and within cells. Cellular responses to growth factors, neurotransmitters, hormones and a variety of other signal molecules are initiated through calcium-dependent processes.

Virtually all cell types depend in some manner upon the generation of cytoplasmic $Ca^{2+}$ signals to regulate cell function, or to trigger specific responses. Cytosolic $Ca^{2+}$ signals control a wide array of cellular functions ranging from short-term responses such as contraction and secretion to longer-term regulation of cell growth and proliferation. Usually, these signals involve some combination of release of $Ca^{2+}$ from intracellular stores, such as the endoplasmic reticulum (ER), and influx of $Ca^{2+}$ across the plasma membrane. In one example, cell activation begins with an agonist binding to a surface membrane receptor, which is coupled to phospholipase C (PLC) through a G-protein mechanism. PLC activation leads to the production of inositol 1,4,5-triphosphate ($IP_3$), which in turn activates the $IP_3$ receptor causing release of $Ca^{2+}$ from the ER. The fall in ER $Ca^{2+}$ then signals to activate plasma membrane store-operated calcium (SOC) channels.

Store-operated calcium (SOC) influx is a process in cellular physiology that controls such diverse functions such as, but not limited to, refilling of intracellular $Ca^{2+}$ stores (Putney et al. Cell, 75, 199-201, 1993), activation of enzymatic activity (Fagan et al., J. Biol. Chem. 275:26530-26537, 2000), gene transcription (Lewis, Annu. Rev. Immunol. 19:497-521, 2001), cell proliferation (Nunez et al., J. Physiol. 571.1, 57-73, 2006), and release of cytokines (Winslow et al., Cur. Opin. Immunol. 15:299-307, 2003). In some nonexcitable cells, e.g., blood cells, immune cells, hematopoietic cells, T lymphocytes and mast cells, pancreatic acinar cells (PACs), epithelial and ductal cells of other glands (eg salivary glands), endothelial and endothelial progenitor cells, SOC influx occurs through calcium release-activated calcium (CRAC) channels, a type of SOC channel.

The calcium influx mechanism has been referred to as store-operated calcium entry (SOCE). Stromal interaction molecule (STIM) proteins are an essential component of SOC channel function, serving as the sensors for detecting the depletion of calcium from intracellular stores and for activating SOC channels.

Calcium Homeostasis

Cellular calcium homeostasis is a result of the summation of regulatory systems involved in the control of intracellular calcium levels and movements. Cellular calcium homeostasis is achieved, at least in part, by calcium binding and by movement of calcium into and out of the cell across the plasma membrane and within the cell by movement of calcium across membranes of intracellular organelles including, for example, the endoplasmic reticulum, sarcoplasmic reticulum, mitochondria and endocytic organelles including endosomes and lysosomes.

Movement of calcium across cellular membranes is carried out by specialized proteins. For example, calcium from the extracellular space can enter the cell through various calcium channels and a sodium/calcium exchanger and is actively extruded from the cell by calcium pumps and sodium/calcium exchangers. Calcium can also be released from internal stores through inositol trisphosphate or ryanodine receptors and can be taken up by these organelles by means of calcium pumps.

Calcium can enter cells by any of several general classes of channels, including but not limited to, voltage-operated calcium (VOC) channels, store-operated calcium (SOC) channels, and sodium/calcium exchangers operating in reverse mode. VOC channels are activated by membrane depolarization and are found in excitable cells like nerve and muscle and are for the most part not found in nonexcitable cells. Under some conditions, $Ca^{2+}$ can enter cells via $Na+$-$Ca^{2+}$ exchangers operating in reverse mode.

Endocytosis provides another process by which cells can take up calcium from the extracellular medium through endosomes. In addition, some cells, e.g., exocrine cells, can release calcium via exocytosis.

Cytosolic calcium concentration is tightly regulated with resting levels usually estimated at approximately 0.1 µM in mammalian cells, whereas the extracellular calcium concentration is typically about 2 mM. This tight regulation facilitates transduction of signals into and within cells through transient calcium flux across the plasma membrane and membranes of intracellular organelles. There is a multiplicity of intracellular calcium transport and buffer systems in cells that serve to shape intracellular calcium signals and maintain the low resting cytoplasmic calcium concentration. In cells at rest, the principal components involved in maintaining basal calcium levels are calcium pumps and leak pathways in both the endoplasmic reticulum and plasma membrane. Disturbance of resting cytosolic calcium levels can affect transmission of calcium-dependent signals and give rise to defects in a number of cellular processes. For example, cell proliferation involves a prolonged calcium signaling sequence. Other cellular processes that involve calcium signaling include, but are not limited to, secretion, transcription factor signaling, and fertilization.

Cell-surface receptors that activate phospholipase C (PLC) create cytosolic $Ca^{2+}$ signals from intra- and extracellular sources. An initial transient rise of $[Ca^{2+}]i$ (intracellular calcium concentration) results from the release of $Ca^{2+}$ from the endoplasmic reticulum (ER), which is triggered by the PLC product, inositol-1,4,5-trisphosphate ($IP_3$), opening $IP_3$ receptors in the ER (Streb et al. Nature, 306, 67-69, 1983). A subsequent phase of sustained $Ca^{2+}$ entry across the plasma membrane then ensues, through specialized store operated calcium (SOC) channels (in the case of non-excitable cells like immune PAC cells, the SOC channels are calcium release-activated calcium (CRAC) channels) in the plasma membrane. Store-operated Ca2+ entry (SOCE) is the process in which the emptying of $Ca^{2+}$ stores itself activates $Ca^{2+}$ channels in the plasma membrane to help refill the stores (Putney, Cell Calcium, 7, 1-12, 1986; Parekh et al., Physiol. Rev. 757-810; 2005). SOCE does more than simply provide Ca2+ for refilling stores, but can itself generate sustained $Ca^{2+}$ signals that control such essential functions as gene expression, cell metabolism and exocytosis (Parekh and Putney, Physiol. Rev. 85, 757-810 (2005).

In lymphocytes and mast cells, activation of antigen or Fc receptors, respectively causes the release of $Ca^{2+}$ from intracellular stores, which in turn leads to $Ca^{2+}$ influx through CRAC channels in the plasma membrane. The subsequent rise in intracellular $Ca^{2+}$ activates calcineurin, a phosphatase that regulates the transcription factor NFAT. In resting cells, NFAT is phosphorylated and resides in the cytoplasm, but when dephosphorylated by calcineurin, NFAT translocates to the nucleus and activates different genetic programs depending on stimulation conditions and cell type. In response to infections and during transplant rejection, NFAT partners with the transcription factor AP-1 (Fos-Jun) in the nucleus of "effector" T cells, thereby trans-activating cytokine genes, genes that regulate T cell proliferation and other genes that orchestrate an active immune response (Rao et al., Annu Rev Immunol., 1997; 15:707-47). In contrast, in T cells recognizing self-antigens, NFAT is activated in the absence of AP-1, and activates a transcriptional program known as "anergy" that suppresses autoimmune responses (Macian et al., Transcriptional mechanisms underlying lymphocyte tolerance. Cell. 2002 Jun. 14; 109(6):719-31). In a subclass of T cells known as regulatory T cells which suppress autoimmunity mediated by self-reactive effector T cells, NFAT partners with the transcription factor FOXP3 to activate genes responsible for suppressor function (Wu et al., Cell, 2006 Jul. 28; 126(2): 375-87; Rudensky A Y, Gavin M. Zheng Y. Cell. 2006 Jul. 28; 126(2):253-256).

The endoplasmic reticulum (ER) carries out a variety processes. The ER has a role as both a $Ca^{2+}$ sink and an agonist-sensitive $Ca^{2+}$ store, and protein folding/processing takes place within its lumen. In the latter case, numerous $Ca^{2+}$-dependent chaperone proteins ensure that newly synthesized proteins are folded correctly and sent off to their appropriate destination. The ER is also involved in vesicle trafficking, release of stress signals, regulation of cholesterol metabolism, and apoptosis. Many of these processes require intraluminal $Ca^{2+}$ and protein misfolding, ER stress responses, and apoptosis can all be induced by depleting the ER of $Ca^{2+}$ for prolonged periods of time. Because it contains a finite amount of $Ca^{2+}$, it is clear that ER $Ca^{2+}$ content must fall after release of that $Ca^{2+}$ during stimulation. However, to preserve the functional integrity of the ER, it is vital that the $Ca^{2+}$ content does not fall too low or is maintained at least at a low level. Replenishment of the ER with $Ca^{2+}$ is therefore a central process to all eukaryotic cells. Because a fall in ER $Ca^{2+}$ content activates store-operated $Ca^{2+}$ channels in the plasma membrane, a major function of this $Ca^{2+}$ entry pathway is believed to be maintenance of ER $Ca^{2+}$ levels that are necessary for proper protein synthesis and folding. However, store-operated $Ca^{2+}$ channels have other important roles.

The understanding of store-operated calcium entry was provided by electrophysiological studies which established that the process of emptying the stores activated a $Ca^{2+}$ current in mast cells called $Ca^{2+}$ release-activated $Ca^{2+}$ current or ICRAC. ICRAC is non-voltage activated, inwardly rectifying, and remarkably selective for $Ca^{2+}$. It is found in several cell types mainly of hemapoietic origin. ICRAC is not the only store-operated current, and it is now apparent that store-operated influx encompasses a family of $Ca^{2+}$ permeable channels, with different properties in different cell types. ICRAC was the first store-operated $Ca^{2+}$ current to be described and remains a popular model for studying store-operated influx.

Store-operated calcium channels can be activated by any procedure that empties ER $Ca^{2+}$ stores; it does not seem to matter how the stores are emptied, the net effect is activation of store-operated $Ca^{2+}$ entry. Physiologically, store emptying is evoked by an increase in the levels of $IP_3$ or other $Ca^{2+}$-releasing signals followed by $Ca^{2+}$ release from the stores. But there are several other methods for emptying stores. These methods include the following:

1) elevation of $IP_3$ in the cytosol (following receptor stimulation or, dialyzing the cytosol with $IP_3$ itself or related congeners like the nonmetabolizable analog $Ins(2,4,5)P_3$);
2) application of a $Ca^{2+}$ ionophore (e.g., ionomycin) to permeabilize the ER membrane;
3) dialyzing the cytoplasm with high concentrations of $Ca^{2+}$ chelators (e.g., EGTA or BAPTA), which chelate $Ca^{2+}$ that leaks from the stores and hence prevent store refilling;
4) exposure to the sarcoplasmic/endoplasmic reticulum $Ca^{2+}$-ATPase (SERCA) inhibitors like thapsigargin, cyclopiazonic acid, and di-tert-butylhydroquinone;
5) sensitizing the $IP_3$ receptors to resting levels of InsP3 with agents like thimerosal; and
6) loading membrane-permeable metal $Ca^{2+}$ chelators like N,N,N',N'-tetrakis(2-pyridylmethyl)ethylene diamine (TPEN) directly into the stores.

Through mass action, TPEN lowers free intraluminal $Ca^{2+}$ concentration without changing total store $Ca^{2+}$ such that the store depletion-dependent signal is generated.

These methods of emptying stores are not devoid of potential problems. The key feature of store-operated $Ca^{2+}$ entry is that it is the fall in $Ca^{2+}$ content within the stores and not the subsequent rise in cytoplasmic $Ca^{2+}$ concentration that activates the channels. However, ionomycin and SERCA pump blockers generally cause a rise in cytoplasmic $Ca^{2+}$ concentration as a consequence of store depletion, and such a rise in Ca could open $Ca^{2+}$-activated cation channels permeable to $Ca^{2+}$. One way to avoid such problems is to use agents under conditions where cytoplasmic $Ca^{2+}$ has been strongly buffered with high concentrations of $Ca^{2+}$ chelator such as EGTA or BAPTA.

Store-Operated Calcium Entry

Reduced calcium concentration in intracellular calcium stores such as the endoplasmic reticulum resulting from release of calcium therefrom provides a signal for influx of calcium from the extracellular medium into the cell. This influx of calcium, which produces a sustained "plateau" elevation of cytosolic calcium concentration, generally does not rely on voltage-gated plasma membrane channels and does not involve activation of calcium channels by calcium. This calcium influx mechanism is referred to as capacitive calcium entry (CCE), calcium release-activated, store-operated or depletion-operated calcium entry. Store-operated calcium entry can be recorded as an ionic current with distinctive properties. This current is referred to as $I_{SOC}$ (store-operated current) or $I_{CRAC}$ (calcium release-activated current).

Electrophysiological analysis of store-operated or calcium release-activated currents reveal distinct biophysical properties (see, e.g., Parekh and Penner (1997) *Physiol. Rev.* 77:901-930) of these currents. For example, the current can be activated by depletion of intracellular calcium stores (e.g., by non-physiological activators such as thapsigargin, CPA, ionomycin and BAPTA, and physiological activators such as $IP_3$) and can be selective for divalent cations, such as calcium, over monovalent ions in physiological solutions or conditions, can be influenced by changes in cytosolic calcium levels, and can show altered selectivity and conductivity in the presence of low extracellular concentrations of divalent cations. The current may also be blocked or enhanced by 2-APB (depending on concentration) and blocked by SKF96365 and $Gd^{3+}$ and generally can be described as a calcium current that is not strictly voltage-gated.

Patch-clamp studies in mast cells and Jurkat leukemic T cells have established the CRAC entry mechanism as an ion channel with distinctive biophysical characteristics, including a high selectivity for $Ca^{2+}$ paired with an exceedingly low conductance. Furthermore, the CRAC channel was shown to fulfill the rigorous criteria for being store-operated, which is the activation solely by the reduction of $Ca^{2+}$ in the ER rather than by cytosolic $Ca^{2+}$ or other messengers generated by PLC (Prakriya et al., In *Molecular and Cellular Insights into Ion Channel Biology* (ed. Robert Maue) 121-140 (Elsevier Science, Amsterdam. 2004)).

Regulation of Store-Operated Calcium Entry by Intracellular Calcium Stores

Store-operated calcium entry is regulated by the level of calcium within an intracellular calcium store. Intracellular calcium stores can be characterized by sensitivity to agents, which can be physiological or pharmacological, which activate release of calcium from the stores or inhibit uptake of calcium into the stores. Different cells have been studied in characterization of intracellular calcium stores, and stores have been characterized as sensitive to various agents, including, but not limited to, $IP_3$ and compounds that effect the $IP_3$ receptor, thapsigargin, ionomycin and/or cyclic ADP-ribose (cADPR) (see, e.g., Berridge (1993) *Nature* 361:315-325; Churchill and Louis (1999) *Am. J. Physiol.* 276:$C_4$26-$C_4$34; Dargie et al. (1990) *Cell Regul.* 1 :279-290; Gerasimenko et al. (1996) *Cell* 84:473-480; Gromoda et al. (1995) *FEBS Lett.* 360:303-306, Guse et al. (1999) *Nature* 398:70-73).

Accumulation of calcium within endoplasmic reticulum and sarcoplasmic reticulum (SR; a specialized version of the endoplasmic reticulum in striated muscle) storage organelles is achieved through sarcoplasmic-endoplasmic reticulum calcium ATPases (SERCAs), commonly referred to as calcium pumps. During signaling (i.e., when endoplasmic reticulum channels are activated to provide for calcium release from the endoplasmic reticulum into the cytoplasm), endoplasmic reticulum calcium is replenished by the SERCA pump with cytoplasmic calcium that has entered the cell from the extracellular medium (Yu and Hinkle (2000) *J. Biol. Chem.* 275:23648-23653; Hofer et al. (1998) *EMBO J.* 17:1986-1995).

Calcium release channels associated with $IP_3$ and ryanodine receptors provide for controlled release of calcium from endoplasmic and sarcoplasmic reticulum into the cytoplasm resulting in transient increases in cytoplasmic calcium concentration. $IP_3$ receptor-mediated calcium release is triggered by $IP_3$ formed by the breakdown of plasma membrane phosphoinositides through the action of phospholipase C, which is activated by binding of an agonist to a plasma membrane G protein-coupled receptor or tyrosine kinase. Ryanodine receptor-mediated calcium release is triggered by an increase in cytoplasmic calcium and is referred to as calcium-induced calcium release (CICR). The activity of ryanodine receptors (which have affinity for ryanodine and caffeine) may also be regulated by cyclic ADP-ribose.

Thus, the calcium levels in the stores, and in the cytoplasm, fluctuate. For example, ER free calcium concentration can decrease from a range of about 60-400 μM to about 1-50 μM when HeLa cells are treated with histamine, an agonist of PLC-linked histamine receptors (Miyawaki et al. (1997) *Nature* 388:882-887). Store-operated calcium entry is activated as the free calcium concentration of the intracellular stores is reduced. Depletion of store calcium, as well as a concomitant increase in cytosolic calcium concentration, can thus regulate store-operated calcium entry into cells.

Cytoplasmic Calcium Buffering

Agonist activation of signaling processes in cells can involve dramatic increases in the calcium permeability of the endoplasmic reticulum, for example, through opening of $IP_3$ receptor channels, and the plasma membrane through store-operated calcium entry. These increases in calcium permeability are associated with an increase in cytosolic calcium concentration that can be separated into two components: a "spike" of calcium release from the endoplasmic reticulum during activation of the $IP_3$ receptor and a plateau phase which is a sustained elevation of calcium levels resulting from entry of calcium into the cytoplasm from the extracellular medium. Upon stimulation, the resting intracellular free calcium concentration of about 100 nM can rise globally to greater than 1 μM and higher in microdomains of the cell. The cell modulates these calcium signals with endogenous calcium buffers, including physiological buffering by organelles such as mitochondria, endoplasmic reticulum and Golgi. Mitochondrial uptake of calcium through a uniporter in the inner membrane is driven by the large negative mitochondrial membrane potential, and the accumulated calcium is released slowly through sodium-dependent and -independent exchangers, and, under some circumstances, the permeability transition pore (PTP). Thus, mitochondria can act as calcium buffers by taking up calcium during periods of cellular activation and can slowly release it later. Uptake of calcium into the endoplasmic reticulum is regulated by the sarcoplasmic and endoplasmic reticulum calcium ATPase (SERCA). Uptake of calcium into the Golgi is mediated by a P-type calcium transport ATPase ($PMR_1$/$ATP2C_1$). Additionally, there is evidence that a significant amount of the calcium released upon $IP_3$ receptor activation is extruded from the cell through the action of the plasma membrane calcium ATPase. For example, plasma membrane calcium ATPases provide the dominant mechanism for calcium clearance in human T cells and Jurkat cells, although sodium/calcium exchange also contributes to calcium clearance in human T cells. Within calcium-storing organelles, calcium ions can be bound to specialized calcium-buffering proteins, such as, for example, calsequestrins, calreticulins and calnexins. Additionally, there are calcium-buffering proteins in the cytosol that modulate calcium spikes and assist in redistribution of calcium ions. Thus, proteins and other molecules that participate in any of these and other mechanisms through which cytosolic calcium levels can be reduced are proteins that are involved in, participate in and/or provide for cytoplasmic calcium buffering. Thus, cytoplasmic calcium buffering helps regulate cytoplasmic $Ca^{2+}$ levels during periods of sustained calcium influx through SOC channels or bursts of $Ca^{2+}$ release. Large increases in cytoplasmic $Ca^{2+}$ levels or store refilling deactivate SOCE.

Downstream Calcium Entry-Mediated Events

In addition to intracellular changes in calcium stores, store-operated calcium entry affects a multitude of events that are consequent to or in addition to the store-operated changes. For example $Ca^{2+}$ influx results in the activation of a large number of calmodulin-dependent enzymes including the serine phosphatase calcineurin. Activation of calcineurin by an increase in intracellular calcium results in acute secretory processes such as mast cell degranulation. Activated mast cells release preformed granules containing histamine, heparin, TNFα and enzymes such as β-hexosaminidase. Some cellular events, such as B and T cell proliferation, require sustained calcineurin signaling, which requires a sustained increase in intracellular calcium. A number of transcription factors are regulated by calcineurin, including NFAT (nuclear factor of activated T cells), MEF$_2$ and NFκB. NFAT transcription factors play important roles in many cell types, including immune cells. In immune cells NFAT mediates transcription of a large number of molecules, including cytokines, chemokines and cell surface receptors. Transcriptional elements for NFAT have been found within the promoters of cytokines such as IL-2, IL-3, IL-4, IL-5, IL-8, IL-13, as well as tumor necrosis factor alpha (TNFα), granulocyte colony-stimulating factor (G-CSF), and gamma-interferon (γ-IFN).

The activity of NFAT proteins is regulated by their phosphorylation level, which in turn is regulated by both calcineurin and NFAT kinases. Activation of calcineurin by an increase in intracellular calcium levels results in dephosphorylation of NFAT and entry into the nucleus. Rephosphorylation of NFAT masks the nuclear localization sequence of NFAT and prevents its entry into the nucleus. Because of its strong dependence on calcineurin-mediated dephosphorylation for localization and activity, NFAT is a sensitive indicator of intracellular free calcium levels.

Calcium Channel Inhibitors

Disclosed herein are a number of Calcium channel inhibitors consistent with the methods, compositions, administration regimens and compositions for use disclosed herein. In some embodiments a Calcium channel inhibitor is a SOC inhibitor. In some embodiments the Calcium channel inhibitor is a CRAC inhibitor. In some embodiments, the Calcium channel inhibitor inhibits a channel comprising STIM1 protein. In some embodiments, the Calcium channel inhibitor inhibits a channel comprising Orai1 protein. In some embodiments, the Calcium channel inhibitor inhibits a channel comprising Orai2 protein.

In some embodiments the compound is a compound having the structure of:

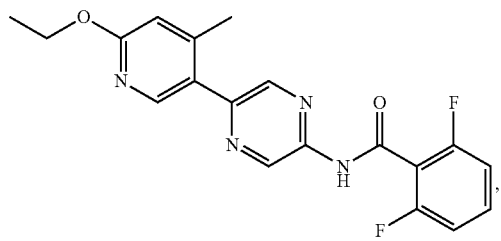

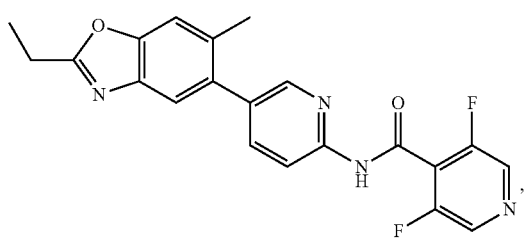

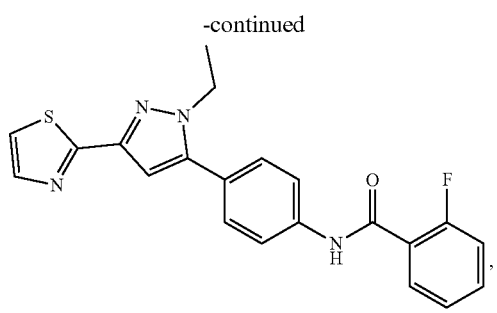

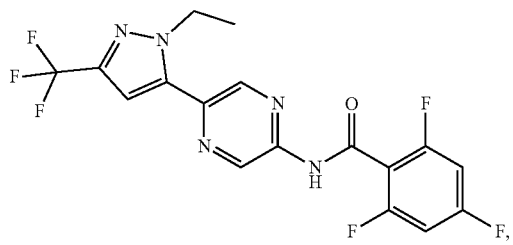

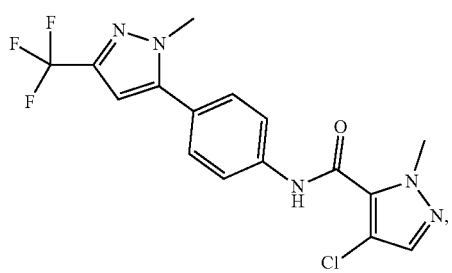

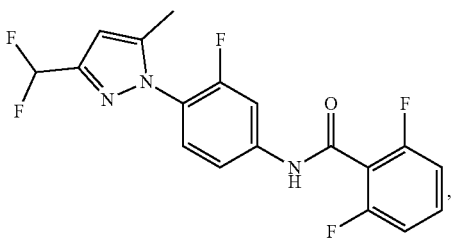

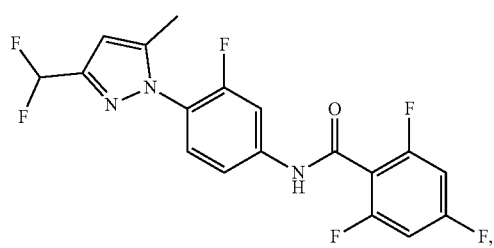

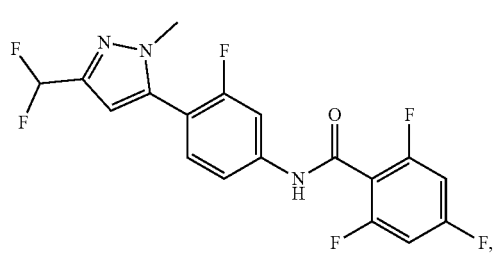

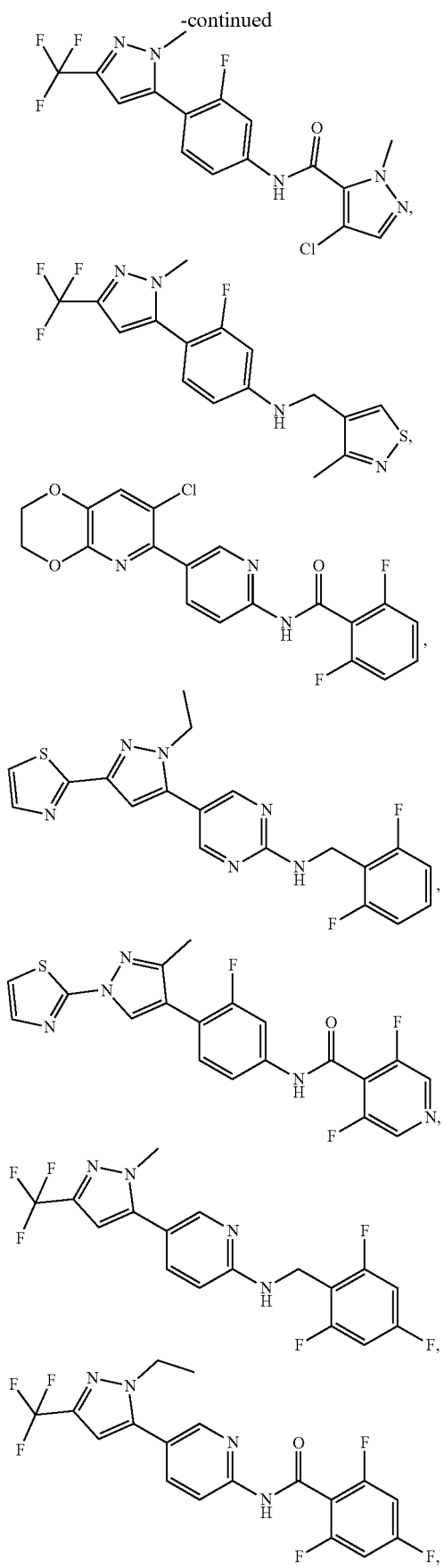
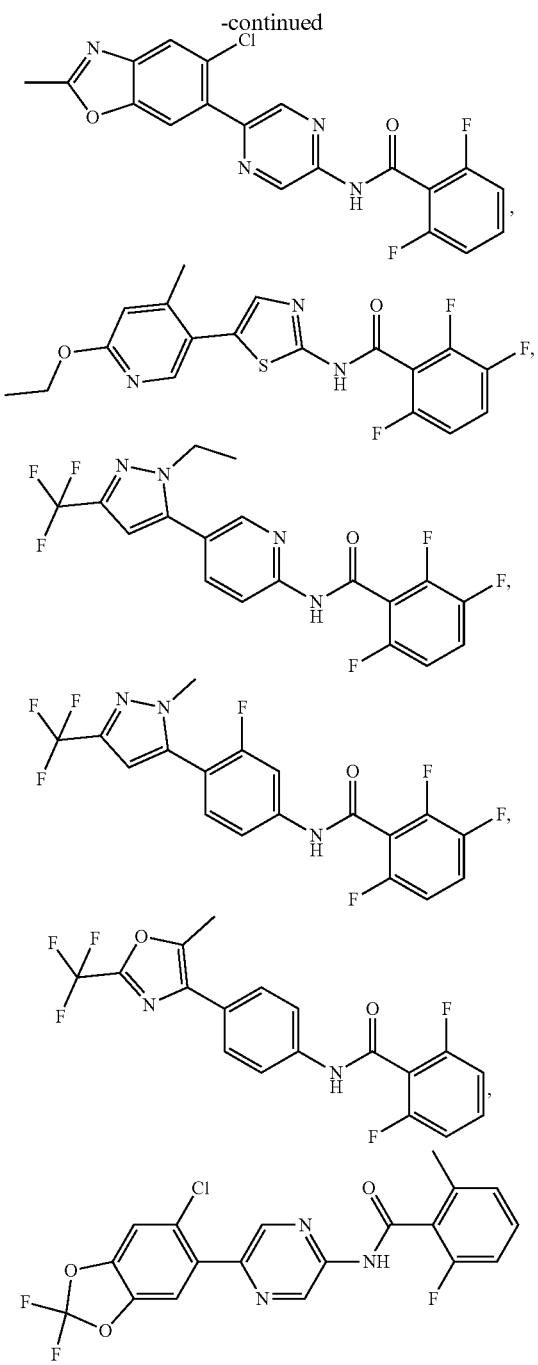

or a pharmaceutically acceptable salt, pharmaceutically acceptable solvate, or pharmaceutically acceptable prodrug thereof. In some embodiments the compound is selected form a list of compounds consisting: N-(5-(6-chloro-2,2-difluorobenzo[d][1,3]dioxazol-5-yl)pyridin-2-yl)-2-fluoro-6-methylbenzamide. In some aspects the intracellular Calcium signaling inhibitor is a compound of N-(5-(6-chloro-2,2-difluorobenzo[d][1,3]dioxol-5-yl)pyrazin-2-yl)-2-fluoro-6-methylbenzamide or a pharmaceutically acceptable-salt, pharmaceutically acceptable solvate, or pharmaceutically acceptable prodrug thereof. In some aspects the intracellular Calcium signaling inhibitor is chosen from among the compounds, N-(5-(6-ethoxy-4-methyl-pyridin-3-yl)pyrazin-2-yl)-2,6-difluorobenzamide, N-(5-(2- ethyl-6-methylbenzo[d]oxazol-5-yl)pyridin-2-yl)-3,5-difluoroisonicotinamide, N(4-(1-methyl-3-(thiazol-2-yl)-1H-pyrazol-5-yl)phenyl)-2-fluorobenzamide, N-(5-(1-ethyl-3-(triflouromethyl)-1H-pyrazol-5-yl)pyrazin-2-yl-2,4,6-trifluorobenzamide, 4-chloro-1-methyl-N-(4-(1-methyl-3-(trifluoromethyl)-1H-pyrazol-5-yl)phenyl)-1H-pyrazole-5-carboxamide, N-(4-(3-(difluoromethyl)-5-methyl-1H-pyrazol-1-yl)-3-fluorophenyl)-2,6-difluorobenzamide, N-(4-(3-(difluoromethyl)-5-methyl-1H-pyrazol-1-yl)-3-fluorophenyl)-2,4,6-trifluorobenzamide, N-(4-(3-(difluoromethyl)-1-methyl-1H-pyrazol-5-yl)-3-fluorophenyl)-2,4,6-trifluorobenzamide, 4-chloro-N-(3-fluoro-4-(1-methyl-3-(trifluoromethyl)-1H-pyrazol-5-yl)phenyl)-1-methyl-1H-pyrazole-5-carboxamide, 3-fluoro-4-(1-methyl-3-(trifluoromethyl)-1H-pyrazol-5-yl)-N-((3-methylisothiazol-4-yl)methyl)aniline, N-(5-(7-chloro-2,3-dihydro-[1,4]dioxino[2,3-b]pyridin-6-yl)pyridin-2-yl)-2,6-difluorobenzamide, N-(2,6-difluorobenzyl)-5-(1-ethyl-3-(thiazol-2-yl)-1H-pyrazol-5-yl)pyrimidin-2-amine, 3,5-difluoro-N-(3-fluoro-4-(3-methyl-1-(thiazol-2-yl)-1H-pyrazol-4-yl)phenyl)isonicotinamide, 5-(1-methyl-3-(trifluoromethyl)-1H-pyrazol-5-yl)-N-(2,4,6-trifluorobenzyl)pyridin-2-amine, N-(5-(1-ethyl-3-(trifluoromethyl)-1H-pyrazol-5-yl)pyridin-2-yl)-2,4,6-trifluorobenzamide, N-(5-(5-chloro-2-methylbenzo[d]oxazol-6-yl)pyrazin-2-yl)-2,6-difluorobenzamide, N-(5-(6-ethoxy-4-methylpyridin-3-yl)thiazol-2-yl)-2,3,6-trifluorobenzamide, N-(5-(1-ethyl-3-(trifluoromethyl)-1H-pyrazol-5-yl)pyridin-2-yl)-2,3,6-trifluorobenzamide, 2,3,6-trifluoro-N-(3-fluoro-4-(1-methyl-3-(trifluoromethyl)-1H-pyrazol-5-yl)phenyl)benzamide, 2,6-difluoro-N-(4-(5-methyl-2-(trifluoromethyl)oxazol-4-yl)phenyl)benzamide, or N-(5-(6-chloro-2,2-difluorobenzo[d][1,3]dioxol-5-yl)pyrazin-2-yl)-2-fluoro-6-methylbenzamide or a pharmaceutically acceptable salt, pharmaceutically acceptable solvate, or pharmaceutically acceptable prodrug thereof.

Calcium Signaling and Pancreatic Health

Calcium signaling is central to healthy pancreatic activity. Food stimulates the release of acetylcholine (ACh) and cholecyctokinin (CCK), which interact with Phospholipase C (PLC)-linked receptors on Pancreatic Acinar Cells (PACs). In healthy PACs, ACh or CCK receptors trigger formation of $IP_3$, 1,4,5-inositol triphosphate, which diffuses to the apical region and stimulates $IP_3$ receptors on the Endoplasmic Reticulum (ER) to release $Ca^{2+}$ in a controlled, pulsatile manner. $Ca^{2+}$ oscillations stimulate release of zymogens (pro-enzymes) into the pancreatic duct. Over time, the ER $Ca^{2+}$ needs to be replenished, which is accomplished by gentile activation of CRAC channels in the basolateral region of the cell.

In certain situations (e.g., alcoholism or binge drinking, gall stones, etc.), fatty acid ethyl esters (FAEEs) formed from alcohol, or bile acids which accumulate due to gallstones diffuse into the PACs. Inside the PACs, FAEEs and bile acids cause massive release of ER $Ca^{2+}$ by activating $IP_3$ receptors. Hyperstimulation of CCK receptors can also elicit robust $Ca^{2+}$ release from ER stores. Emptying of $Ca^{2+}$ stores leads to hyperactivation of CRAC channels, causing excessive influx of $Ca^{2+}$. The large $Ca^{2+}$ influx causes release of enzymes from zymogen granules, and inappropriate activation of intracellular trypsin, which itself then activated other pancreatic digestive enzymes and initiates autodigestion and necrosis of the pancreas that can be blocked by a CRAC channel inhibitor such as Compound I, GSK-7975A, N-(5-(2,5-dimethylbenzo[d]oxazol-6-yl)thiazol-2-yl)-2,3,6-trifluorobenzamide ("Compound II"), or 2,3,6-trifluoro-N-(3-fluoro-4-(1-methyl-3-(trifluoromethyl)-1H-pyrazol-5-yl)phenyl)benzamide ("Compound III").

If unaddressed, the inappropriate release and activation of digestive enzymes such as trypsin from zymogen granules can lead to autodigestion of pancreatic cells, leading to pancreatitis. As mentioned above, acute or chronic pancreatitis can have a substantial negative effect on an individual's health.

Symptoms and Causes of Pancreatitis

Pancreatitis, acute or chronic, is associated with severe upper abdominal or left upper quadrant burning pain radiating to the back, nausea, and vomiting that is worsened with eating. Depending on the severity of the condition, internal bleeding may also occur. Blood pressure, heart and respiratory rates are often elevated, although dehydration may lead to a decrease rather than an increase in blood pressure. The abdomen is often tender but less so than the pain at the pancreas itself. Reflex bowel paralysis is commonly seen in pancreatitis cases, and fever or jaundice is not uncommon. Common symptoms and signs of pancreatitis include: severe epigastric pain (upper abdominal pain) radiating to the back, nausea, vomiting, loss of appetite, fever, chills (shivering), hemodynamic instability (which includes shock), tachycardia (rapid heartbeat), respiratory distress, and peritonitis.

Less commonly observed symptoms, indicative of severe disease, include a number of medical 'signs' indicative of severe abdomina distress: Grey-Turner's sign (hemorrhagic discoloration of the flanks), Cullen's sign (hemorrhagic discoloration of the umbilicus), Pleural effusions (fluid in the bases of the pleural cavity), Grünwald sign (appearance of ecchymosis, large bruise, around the umbilicus due to local toxic lesion of the vessels), Körte's sign (pain or resistance in the zone where the head of pancreas is located (in epigastrium, 6-7 cm above the umbilicus)), Kamenchik's sign (pain with pressure under the xiphoid process), Mayo-Robson's sign (pain while pressing at the top of the angle lateral to the Erector spinae muscles and below the left 12th rib (left costovertebral angle (CVA)) such as at Mayo-Robson's point (a point on border of inner ⅔ with the external ⅓ of the line that represents the bisection of the left upper abdominal quadrant, where tenderness on pressure exists in disease of the pancreas. At this point the tail of pancreas is projected on the abdominal wall).

A person suffering from pancreatitis may demonstrate some, all, or few to none of the above-mentioned symptoms. In some cases abdominal pain may be the sole symptom of the condition.

Chronic pancreatitis can lead to diabetes or pancreatic cancer. Defects in the delivery of digestive enzymes such as trypsin may lead to impaired digestion, leading to weight loss.

As many as eighty percent of cases of pancreatitis are caused by alcohol and gallstones. Gallstones are the single most common etiology of acute pancreatitis. Alcohol is the single most common etiology of chronic pancreatitis.

However, aside from alcohol and gall stones, there are a number of additional causes of pancreatitis. Some medications may be associated with pancreatitis. Examples of medications associated with pancreatitis include corticosteroids such as prednisolone, HIV drugs such as didanosine and pentamidine, diuretics, anticonvulsants such as valproic acid, chemotherapeutic agents such as L-asparaginase and azathioprine, estrogen, medications that increase blood triglycerides, statins such as cholesterol-lowering statins, antihyperglycemic agents like metformin, and gliptins such as vildagliptin, sitagliptin, saxagliptin, and linagliptin, tetracycline, sulfonamides, azathioprine, mercaptopurine, pentamidine, Grimethoprim-suilfamethoxazole, and salicylates. In some cases, drugs which are used to treat conditions associated with increased events of pancreatitis may also be incidentally linked to pancreatitis. Examples include statins in dyslipidemia and gliptins in diabetes. Additionally, some atypical antipsychotics such as clozapine, risperidone, and olanzapine may also be responsible for causing pancreatitis. This list is not exhaustive.

Non-pharmaceutical causes of pancreatitis are also known. For example, inherited forms of pancreatitis are known that result in the activation of trypsinogen within the pancreas, leading to autodigestion. Genes implicated in heritable pancreatitis include Trypsin1, which codes for trypsinogen, SPINK1, which codes for a trypsin inhibitor, and cystic fibrosis transmembrane conductance regulator.

Other common nonpharmaceutical causes of pancreatitis include trauma, mumps, autoimmune disease, high blood calcium, hypothermia, and undergoing endoscopic retrograde cholangiopancreatography (ERCP). Pancreas divisum is a common congenital malformation of the pancreas that may underlie some recurrent cases. Penetrating ulcers are also associated with pancreatitis. Diabetes mellitus type 2 is associated with a 2.8-fold higher risk of developing symptoms of pancreatitis. Additional conditions associated with pancreatitis include pancreatic cancer, pancreatic duct stones, vasculitis (inflammation of the small blood vessels in the pancreas), coxsackie virus infection, and porphyria, particularly acute intermittent porphyria and erythropoietic protoporphyria. Pregnancy is associated with pancreatitis in some cases. Repeated marathon running, anorexia and bulemia, as well as fatty necrosis, cystic fibrosis, and scorpion venom are implicated in some pancreatitis cases.

A number of infectious agents are implicated in pancreatitis. Examples include viral infection by viruses such as Cytomegalovirus, Hepatitis B, Herpes simplex virus, Mumps Rubulavirus, Varicella-zoster virus; Bacterial infection, such as by bacteria of the genera *Legionella, Leptospira, Mycoplasma,* or *Salmonella*; fungal infection such as by fungi of the genera *Aspergillus*; or parasitic infection by nematodes of the genus *Ascaris* or by apicomplexan alveolates of the genera *Cryptosporidium* and *Toxoplasma*; among others.

The medical students' mnemonic 'GETSMASHED' is often used to remember some of the common causes of Pancreatitis: G—Gall stones E—Ethanol T—Trauma S—Steroids M—Mumps A—Autoimmune Pancreatitis S—Scorpion sting H—Hyperlipidaemia, Hypothermia, Hyperparathyroidism E—Endoscopic retrograde cholangiopancreatography D—Drugs commonly azathioprine, valproic acid.

Pancreatitis may also be idiopathic, in which case no cause is identified.

Categorization of Pancreatitis

Pancreatitis, particularly acute pancreatitis, is often classified as either 'mild', 'moderate', or 'severe' depending upon the predominant response to cell injury. These categories are all characterized by misactivation of pancreatic zymogens such as trypsinogen inside the pancreas, often due to colocalization with the trypsinogen maturase cathepsin, which activates trypsinogen to trypsin. All three categories are characterized by inflammation and edema of the pancreas. Moderate and severe pancreatitis are further characterized by pancreatic necrosis and secondary injury to extrapancreatic organs, with moderate acute pancreatitis patients suffering transient (<48 hour) organ failure, while severe acute pancreatitis patients have persistent (>48 hour) organ failure.

In response to the above-mentioned issues, the pancreas may directly synthesize inflammatory mediators such as TNF-α and IL-1, associated with an inflammatory response and recruitment of neutrophils to the pancreas, or due to necrosis and leakage of cellular components, otherwise activate the immune system. The inflammatory response may lead to secondary manifestations of pancreatitis, such as hypovolemia from capillary permeability, acute respiratory distress syndrome, disseminated intravascular coagulations, renal failure, cardiovascular failure, and gastrointestinal hemorrhage.

Acute pancreatitis (acute hemorrhagic pancreatic necrosis) may further be characterized by acute inflammation and necrosis of pancreas parenchyma, focal enzymic necrosis of pancreatic fat, and vessel necrosis (hemorrhage) resulting from intrapancreatic activation of pancreatic enzymes. Lipase activation may produce necrosis of fat tissue in pancreatic interstitium and peripancreatic spaces as well as vessel damage. Digestion of vascular walls results in thrombosis and hemorrhage. Inflammatory infiltrate is rich in neutrophils. Due to the pancreas lacking a capsule, the inflammation and necrosis can extend to include fascial layers in the immediate vicinity of the pancreas.

Chronic pancreatitis is a prolonged inflammation of the pancreas that alters the organ's normal structure and function. It may be associated with episodes of acute pancreatitis or with persistent abdominal pain or digestive defects. Chronic pancreatitis sufferers usually demonstrate persistent abdominal pain or malabsorption of the fats in foods. Pain during food uptake, particularly fatty or high-protein food uptake, is also common. Weight loss, due to malabsorption of food uptake or to a reduction in food uptake due to discomfort, is also common.

A common complication of chronic pancreatitis is diabetes.

Alcoholism, tobacco use, malnutrition, trauma, hypercalcemia, calcified stones, cystic fibrosis, and hereditary defects in trypsinogen processing and stability are commonly associated with chronic pancreatitis.

Chronic pancreatitis is typically diagnosed based on tests on pancreatic structure and function. Serum amylase and lipase may or may not be moderately elevated in cases of chronic pancreatitis, owing to the uncertain levels of productive cell damage. Elevated lipase is the more likely found of the two. Amylase and lipase are nearly always found elevated in the acute condition along with an elevated CRP inflammatory marker that is broadly in line with the severity of the condition.

A secretin stimulation test is perhaps the most accurate functional test for diagnosis of chronic pancreatitis. Impairment of bi-carbonate production early in chronic pancreatitis is used to identify persons in early stages of disease (sensitivity of 95%). Additional tests used to determine chronic pancreatitis are fecal elastase measurement in stool, serum trypsinogen, computed tomography (CT), ultrasound, EUS, MRI, ERCP and MRCP. Pancreatic calcification may be seen on abdominal X-rays, as well as CT scans. Notably, however, ERCP and X-rays may trigger acute pancreatitis.

A number of additional tests are available to assay for chronic pancreatitis. Elevated serum bilirubin and alkaline phosphatase levels may indicate chronic pancreatitis, in some cases indicating stricturing of the common bile duct due to edema, fibrosis or cancer. Autoimmune response-related chronic pancreatitis may be accompanied by elevations in ESR, IgG4, rheumatoid factor, ANA and anti-smooth muscle antibody, assay of any of which may indicate chronic pancreatitis in a person. A classic symptom of chronic pancreatitis, steatorrhea or food malabsorption, may be diagnosed by two different studies: Sudan chemical staining of feces or fecal fat excretion of 7 grams or more over a 24 hr period on a 100 g fat diet. To check for pancreatic exocrine dysfunction, an exemplary sensitive and specific test is the measurement of fecal elastase, which may be done with a single stool sample, and a value of less than 200 µg/g indicates pancreatic insufficiency.

A number of methods are known to evaluate the severity of pancreatitis in a person. Common tests include BISAP, Ranson's, APACHE-II, and CTSI. The BISAP test, for example, is based upon the following criteria assessed in the first 24 hours after admission: blood urea nitrogen >25 mg/dL (8.92 mmol/L); Impaired Mental Status, defined as: disorientation, lethargy, somnolence, coma or stupor; >2 Systemic Inflammatory Response Syndrome Criteria; Age>60; and Pleural Effusion Present. A positive assessment on any of these criteria results in a 'point' in a total score ranging from 0 to 5. In some implementations of the test, mortality rates ranged from less than 1% in the lowest-risk group to more than 20% in the highest-risk group.

A number of references discuss tests for pancreatitis severity, each of which is hereby incorporated by reference: Wu B U, Johannes R S, Sun X, Tabak Y, Conwell D L, Banks P A. The early prediction of mortality in acute pancreatitis: a large population-based study. Gut. 2008 December; 57(12):1698-703. doi: 10.1136/gut.2008.152702. Epub 2008 Jun. 2. PubMed PMID: 18519429; Papachristou G I, Muddana V, Yadav D, O'Connell M, Sanders M K, Slivka A, Whitcomb D C. Comparison of BISAP, Ranson's, APACHE-II, and CTSI scores in predicting organ failure, complications, and mortality in acute pancreatitis. Am J Gastroenterol. 2010 February; 105(2):435-41; quiz 442. doi: 10.1038/ajg.2009.622. Epub 2009 Oct. 27. PubMed PMID: 19861954; and Gompertz M. Femández L, Lara I, Miranda J P, Mancilla C, Berger Z. [Bedside index for severity in acute pancreatitis (BISAP) score as predictor of clinical outcome in acute pancreatitis: retrospective review of 128 patients]. Rev Med Chil. 2012 August; 140(8):977-83. doi: 10.1590/50034-98872012000800002. Spanish. PubMed PMID: 23282769.

Therapeutic Amelioration of Pancreatitis

Disclosed herein are compositions and methods for the therapeutic amelioration of pancreatitis and symptoms thereof, such as through the administration of a calcium channel inhibitor such as a CRAC inhibitor. In some embodiments the pancreatitis is acute pancreatitis. In some embodiments the pancreatitis is chronic pancreatitis. In some embodiments a method of ameliorating the symptoms of pancreatitis in a person is disclosed. In some embodiments a method of ameliorating the symptoms of pancreatitis in a person is disclosed comprising the steps of identifying a person in need of amelioration of symptoms of pancreatitis, and administering an intracellular Calcium signaling inhibitor to said person at a dose sufficient to ameliorate said symptoms.

The person may be identified using, for example, a common test for pancreatitis symptoms, such as BISAP, Ranson's, APACHE-II, and CTSI. The test may be BISAP. The test may be Ranson's. The test may be APACHE II. The test may be CTSI. In some embodiments a person is identified as a person in need of amelioration of symptoms of pancreatitis by having a BISAP score of 5, 4, 3, 2, or 1. In some embodiments the person is identified as having a BISAP score of 2. In some embodiments the person is identified as having a BISAP score of 3. In some embodiments the person is identified as having a BISAP score of 4. In some embodiments the person is identified as having a BISAP score of 5. In some embodiments a person is identified as having at least 1, 2, 3, 4, 5, 6, 7, 8, 9, or more than 9 symptoms of pancreatitis, such as the symptoms of pancreatitis disclosed herein. In some embodiments, rather than a person, the subject is a non-human mammal.

In some embodiments the symptoms are acute pancreatitis symptoms. In some embodiments the symptoms are chronic pancreatitis symptoms.

The symptoms may comprise at least one of abdominal pain, increased blood anylase levels, increased blood lipase levels, enlarged pancreas, nausea, vomiting, internal bleeding, bowel paralysis, fever, jaundice, weight loss, and elevated heart rate. The symptoms may comprise premature digestive enzyme activation. The premature digestive enzyme activation may, for example, occur in a pancreas of said person. In some embodiments the enzyme comprises trypsin.

In some embodiments, the intracellular Calcium signaling inhibitor is an SOC channel inhibitor. In some embodiments, the intracellular Calcium signaling inhibitor is a CRAC channel inhibitor. In some embodiments, the CRAC channel inhibitor comprises Compound I. In some embodiments, the CRAC channel inhibitor comprises GSK-7975A. In some embodiments, the CRAC channel inhibitor comprises Compound II. In some embodiments, the CRAC channel inhibitor comprises Compound III. In some embodiments, ameliorating symptoms of pancreatitis further comprises administering a painkiller medication. In some embodiments, ameliorating symptoms of pancreatitis further comprises administering a painkiller medication wherein the painkiller medication comprises an opiate. In some embodiments, ameliorating symptoms of pancreatitis further comprises administering a painkiller medication wherein the painkiller medication comprises morphine. In some embodiments, ameliorating symptoms of pancreatitis further comprises administering a painkiller medication wherein the painkiller medication comprises fentanyl. In some embodiments, ameliorating symptoms of pancreatitis further comprises administering a painkiller medication wherein the painkiller medication comprises tramadol. In some embodiments, ameliorating symptoms of pancreatitis further comprises administering a painkiller medication wherein the painkiller medication comprises meperidine.

In some embodiments, the intracellular Calcium signaling inhibitor is delivered to achieve a tissue level concentration that is equal to, about, or greater than the in vitro $IC_{50}$ value determined for the compound. In some embodiments the Calcium signaling inhibitor is delivered to achieve a tissue level concentration that is 1.5×, 2×, 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×. 33×, 34×, 35×, 36×, 37×, 38×, 39×, 40×, 41×, 42×, 43×, 44×, 45×, 46×, 47×, 48×, 49×, 50×, 51×, 52×, 53×, 54×, 55×, 56×, 57×, 58×, 59×, 60×, 61×, 62×, 63×, 64×, 65×, 66×, 67×, 68×, 69×, 70×, 71×. 72×, 73×, 74×, 75×, 76×, 77×, 78×, 79×, 80×, 81×, 82×, 83×, 84×, 85×, 86×, 87×, 88×, 89×, 90×, 91×, 92×, 93×, 94×, 95×, 96×, 97×, 98×, 99×, 100×, or any non-integer multiple ranging from 1× to 100× of the in vitro $IC_{50}$ value determined for the compound.

In some embodiments the Calcium signaling inhibitor is delivered to achieve a tissue level concentration that ranges from 1× to 100×, 2× to 80×, 3× to 60×, 4× to 5×, 5× to 45×, 6× to 44×, 7× to 43×, 8× to 43×, 9× to 41×, or 10× to 40×, or any non-integer within said range, of the in vitro IC$_{50}$ value determined for the compound.

In some embodiments the Calcium signaling inhibitor is delivered to achieve a tissue level concentration that is 1 µM, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 21µM, 22 µM, 23 µM, 24 µM, 25 µM, 26 µM, 27 µM, 28 µM, 29 µM, 30 µM, 31 µM, 32 µM, 33 µM, 34 µM, 35 µM, 36 µM, 37 µM, 38 µM, 39 µM, 40M, 41 µM, 42 µM, 43 µM, 44 µM, 45 µM, 46 µM, 47 µM, 48 µM, 49 µM, 50 µM, 51 µM 52 µM, 53 µM, 54 µM, 55 µM, 56 µM, 57 µM, 58 µM, 59 µM, 60 µM 61 µM, 62 µM, 63 µM, 64 µM, 65 µM, 66 µM, 67 µM, 68 µM, 69 µM, 70 µM, 71 µM, 72 µM, 73 µM, 74 µM, 75 µM, 76 µM, 77 µM, 78 µM, 79 µM, 80 µM, 81 µM, 82 µM, 83 µM, 84 µM, 85 µM, 86 µM, 87 µM, 88 µM, 89 µM, 90 µM, 91 µM, 92 µM, 93 µM, 94 µM, 95 µM, 96 µM, 97M, 98 µM, 99 µM, 100 µM, or any non-integer multiple ranging from about 1 µM to about 100 µM.

In some embodiments the Calcium signaling inhibitor is delivered to achieve a tissue level concentration that ranges from 1 µM to 100 µM, 2 µM to 90 µM, 3 µM to 80 µM, 4 µM to 70 µM, 5 µM to 60 µM, 6 µM to 50 µM, 7 µM to 40 µM, 8 µM to 30 µM, 9 µM to 20 µM, or 10 µM to 40 µM, or any integer or non-integer within said range.

In some embodiments the Calcium signaling inhibitor is delivered to achieve a tissue level concentration that ranges from 9.5 µM to 10.5 µM 9 µM to 11 µM, 8 µM to 12 µM, 7 µM to 13 µM, 5 µM to 15 µM, 2 µM to 20 µM or 1 µM to 50 µM, or any integer or non-integer within said range.

In some embodiments amelioration of pancreatitis comprises reduction in severity of at least one pancreatitis symptom. In some embodiments amelioration of pancreatitis comprises reduction in severity of at least one pancreatitis symptom such that said symptom no longer impacts the previously affected person. In some embodiments amelioration comprises reduction of at least one symptom so that it has no effect on the person. In some embodiments amelioration comprises a 10%, 20%, 30%, 40%, 40%, 50%, 60%, 70%, 80%, 90%, 95%, or 100% reduction in said symptom. In some embodiments, amelioration comprises reduction in severity of a plurality of symptoms, such as 2, 3, 4, 5, 6, 7, 8, 9, or more than 9 symptoms, up to and including all symptoms, said reduction comprising a 10%, 20%, 30%, 40%, 40%, 50%, 60%, 70%, 80%, 90%, 95%, or 100% reduction in said symptoms.

In some embodiments amelioration comprises halting the progression of pancreatitis such as acute pancreatitis or chronic pancreatitis. In some embodiments amelioration comprises halting the progression of pancreatitis such as acute pancreatitis or chronic pancreatitis such that more severe symptoms such as organ failure, pancreas necrosis or death do not occur.

Prophylactic Amelioration of Acute and Chronic Pancreatitis

Disclosed herein are compositions and methods for the prophylactic amelioration of acute pancreatitis and symptoms thereof, such as through the administration of a calcium channel inhibitor such as a CRAC inhibitor. In some embodiments a method of ameliorating the symptoms of pancreatitis in a person is disclosed. In some embodiments a method of ameliorating the symptoms of pancreatitis in a person is disclosed comprising the steps of identifying a person in need of prophylactic amelioration of symptoms of pancreatitis, and administering an intracellular Calcium signaling inhibitor to said person at a dose sufficient to prophylactically ameliorate said symptoms.

In some embodiments, the intracellular Calcium signaling inhibitor is a SOC channel inhibitor. In some embodiments, the intracellular Calcium signaling inhibitor is a CRAC channel inhibitor. In some embodiments, the CRAC channel inhibitor comprises Compound I.

In some embodiments, the CRAC channel inhibitor comprises GSK-7975A. In some embodiments, the CRAC channel inhibitor comprises Compound II. In some embodiments, the CRAC channel inhibitor comprises Compound III. In some embodiments, ameliorating symptoms of pancreatitis further comprises administering a painkiller medication such as an opiate. Morphine is an exemplary painkiller in some embodiments.

In some embodiments, the intracellular Calcium signaling inhibitor is delivered to achieve a tissue level concentration that is equal to, about, or greater than the in vitro IC$_{50}$ value determined for the compound. In some embodiments the Calcium signaling inhibitor is delivered to achieve a tissue level concentration that is 1.5×. 2×, 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×. 33×, 34×, 35×, 36×, 37×, 38×, 39×, 40×, 41×, 42×, 43×, 44×, 45×, 46×, 47×, 48×, 49×, 50×, 51×, 52×, 53×, 54×, 55×, 56×, 57×, 58×, 59×, 60×, 61×, 62×, 63×, 64×, 65×, 66×, 67×, 68×, 69×, 70×, 71×. 72×, 73×, 74×, 75×, 76×, 77×, 78×, 79×, 80×, 81×, 82×, 83×, 84×, 85×, 86×, 87×. 88×, 89×, 90×, 91×, 92×, 93×, 94×, 95×, 96×, 97×, 98×, 99×, 100×, or any non-integer multiple ranging from 1× to 100× of the in vitro IC$_{50}$ value determined for the compound.

In some embodiments the Calcium signaling inhibitor is delivered to achieve a tissue level concentration that ranges from 1× to 100×, 2× to 80×, 3× to 60×, 4× to 50×, 5× to 45×, 6× to 44×, 7× to 43×, 8× to 43×. 9× to 41×, or 10× to 40×, or any non-integer within said range, of the in vitro IC$_{50}$ value determined for the compound.

In some embodiments the Calcium signaling inhibitor is delivered to achieve a tissue level concentration that is 1 µM 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM. 18 µM, 19 µM, 20 µM, 21 µM, 22 µM, 23 µM, 24 µM. 25 µM, 26 µM, 27 µM, 28 µM, 29 µM, 30 µM, 31 µM, 32 µM, 33 µM, 34 µM, 35 µM, 36 µM, 37 µM, 38 µM 39 µM, 40 µM, 41 µM, 42 µM, 43 µM, 44 µM, 45 µM 46 µM, 47 µM, 48 µM, 49 µM, 50 µM, 51 µM, 52 µM, 53 µM, 54 µM, 55 µM. 56 µM, 57 µM, 58 µM, 59 µM, 60 µM, 61 µM, 62 µM, 63 µM, 64 µM, 65 µM, 66 µM, 67 µM, 68 µM, 69 µM, 70 µM, 71 µM, 72 µM, 73 µM, 74 µM, 75 µM, 76 µM, 77 µM, 78 µM, 79 µM, 80 µM, 81 µM, 82 µM, 83 µM, 84 µM, 85 µM, 86 µM, 87 µM, 88 µM, 89 µM, 90 µM, 91 µM, 92 µM, 93 µM, 94 µM, 95 µM, 96 µM, 97 µM, 98 µM, 99 µM, 100 µM, or any non-integer multiple ranging from about 1 µM to about 100 µM.

In some embodiments the Calcium signaling inhibitor is delivered to achieve a tissue level concentration that ranges from 1 µM to 100 µM, 2 µM to 90 µM, 3 µM to 80 µM, 4 µM to 70 µM, 5 µM to 60 µM, 6 µM to 50 µM, 7 µM to 40 µM, 8 µM to 30 µM, 9 µM to 20 µM, or 10 µM to 40 µM, or any integer or non-integer within said range.

In some embodiments the Calcium signaling inhibitor is delivered to achieve a tissue level concentration that ranges from 9.5 µM to 10.5 µM, 9 µM to 11 µM, 8 µM to 12 µM, 7 µM to 13 µM, 5 µM to 15 µM, 2 µM to 20 µM or 1 µM to 50 µM, or any integer or non-integer within said range.

In some embodiments the method comprises prophylactically ameliorating an acute pancreatitis symptom. In some embodiments the method comprises prophylactically ameliorating a chronic pancreatitis symptom.

Prophylactically ameliorating a symptom of pancreatitis may comprise reducing the severity, likelihood of occurrence, or duration of at least one symptom of pancreatitis. Prophylactically ameliorating a symptom of pancreatitis may comprise reducing the severity, likelihood of occurrence, or duration of at least one symptom of pancreatitis up to the point that said at least one symptom does not occur in the person. In some embodiments, prophylactically ameliorating a symptom of pancreatitis may comprise reducing the severity, likelihood of occurrence, or duration of 2, 3, 4, 5, 6, 7, 8, 9, or more than 9 symptoms of pancreatitis, up to and including reducing the severity, likelihood of occurrence, or duration of all symptoms of pancreatitis in a person, such as the symptoms of pancreatitis disclosed herein. In some embodiments, rather than a person, the subject is a non-human mammal.

In some embodiments the person is diagnosed as having a gall stone. In some embodiments the person exhibits symptoms of having a gall stone, such as pain, for example intense pain, in the upper-right side of the abdomen, and/or nausea and vomiting, which may steadily increase for from approximately 30 minutes to several hours. A patient may also experience referred pain between the shoulder blades or below the right shoulder.

In some embodiments the person suffers from alcoholism. In some embodiments the person suffers from chronic alcohol use. In some embodiments the person has suffered from at least one instance of acute alcohol poisoning.

In some embodiments the person is subjected to a drug regimen comprising administration of at least one of a steroid such as a corticosteroid, prednisolone, an HIV drug, didanosine, pentamidine, a diuretic, valproic acid. L-asparaginase, azathioprine, estrogen, a statin such as a cholesterol-lowering statin, an antihyperglycemic agent, metformin, a glipin such as vildagliptin and sitagliptin, an atypical antipsychotic, clozapine, risperidone, and olanzapine.

In some embodiments the person is identified as harboring an inherited form of pancreatitis. In some embodiments the person harbors a mutant allele of Trypsin1 associated with inherited pancreatitis. In some embodiments the person harbors a trypsinogen enzyme variant associated with pancreatitis. In some embodiments the person harbors a mutant allele of SPINK1 associated with inherited pancreatitis. In some embodiments the person harbors a mutant allele of a cystic fibrosis transmembrane conductance regulator associated with inherited pancreatitis.

In some embodiments the person has suffered at least one of high blood calcium, hypothermia, endoscopic retrograde cholangiopancreatography (ERCP), pancreas divisum, a congenital malformation of the pancreas, diabetes mellitus type 2, pancreatic cancer, pancreatic duct stones, vasculitis, inflammation of the small blood vessels in the pancreas, coxsackie virus infection, and porphyra, such as acute intermittent *porphyria* and erythropoietic protoporphyria.

In some embodiments a bodily health condition of said person has been impacted at least one of a gall stone, ethanol poisoning, alcoholism, trauma, mumps, an autoimmune disorder, a scorpion sting, hyperlipidaemia, hypothermia, hyperparathyroidism, and endoscopic retrograde cholangiopancreatography, azathioprine, and valproic acid.

In some embodiments a bodily health condition of said person has been impacted by at least one of a Coxsackie virus, a Cytomegalovirus, a Hepatitis B virus, a Herpes simplex virus, Mumps, a Varicella-zoster virus, a *Legionella* bacterium, a *Leptospira* bacterium, a *Mycoplasma* bacterium, a *Salmonella* bacterium, an *Aspergillus* fungus, an *Ascaris* parasite, a *Cryptosporidium* cell and a *Toxoplasma* cell.

Combination Administration with a Drug or Drugs Associated with Nancreatitis

Disclosed herein are compositions and administration regimens for the combinatorial administration of a Calcium channel inhibitor and a drug associated with pancreatitis. In some embodiments an administration regimen comprises administration to an individual of a drug associated with a negative impact on pancreatic activity, and administration of an intracellular Calcium signaling inhibitor.

In some embodiments the drug associated with a negative impact on pancreatic activity is a drug is selected from the list consisting of: a steroid such as a corticosteroid, prednisolone, an HIV drug, didanosine, pentamidine, a diuretic, valproic acid, L-asparaginase, azathioprine, estrogen, a statin such as a cholesterol-lowering statin, an antihyperglycemic agent, metformin, a glipin such as vildagliptin and sitagliptin, an atypical antipsychotic, clozapine, risperidone, and olanzapine, azathioprine, and valproic acid.

In some embodiments the intracellular Calcium signaling inhibitor is an SOC inhibitor. In some embodiments the intracellular Calcium signaling inhibitor is a CRAC inhibitor. An exemplary CRAC inhibitor comprises Compound I. An exemplary CRAC inhibitor comprises GSK-7975A. An exemplary CRAC inhibitor comprises Compound II. An exemplary CRAC inhibitor comprises Compound III.

In some embodiments the administration regimen comprises administration of a calcium channel inhibitor such as a CRAC inhibitor such as at least one of Compound I, GSK 7975A, Compound II, and Compound III in concert with a drug associated with a negative impact on pancreatic activity. In some embodiments the calcium channel inhibitor such as a CRAC inhibitor such as at least one of Compound I, GSK 7975A, Compound II, and Compound III is administered on the same day as a drug associated with a negative impact on pancreatic activity.

In some embodiments the calcium channel inhibitor such as a CRAC inhibitor such as at least one of Compound I, GSK 7975A, Compound II, and Compound III is administered on the same week as a drug associated with a negative impact on pancreatic activity. In some embodiments the calcium channel inhibitor such as a CRAC inhibitor such as at least one of Compound I, GSK 7975A, Compound II, and Compound III is administered concurrently with each administration of a drug associated with a negative impact on pancreatic activity. In some embodiments the calcium channel inhibitor such as a CRAC inhibitor such as at least one of Compound I, GSK 7975A, Compound II, and Compound III is administered on an administration regimen pattern that is independent of the administration pattern for a drug associated with a negative impact on pancreatic activity. In some embodiments the calcium channel inhibitor such as a CRAC inhibitor such as at least one of Compound I, GSK 7975A, Compound II, and Compound III is administered through the same route of delivery, such as orally or intravenously, as a drug associated with a negative impact on pancreatic activity. In some embodiments the calcium channel inhibitor such as a CRAC inhibitor such as at least one of Compound I, GSK 7975A, Compound II, and Compound III is administered through a separate route of delivery compared to a drug associated with a negative impact on pancreatic activity. In some embodiments the calcium channel inhibitor such as a CRAC inhibitor such as at least one of Compound I, GSK 7975A, Compound II, and Compound III is administered to a person receiving a drug associated with a negative impact on pancreatic activity only after said person shows at least one sign of an impact of said drug on pancreatic activity, for example through an increase in blood amylase activity or blood lipase activity, or through manifestation of at least one pancreatitis symptom as disclosed herein. In some embodiments the calcium channel inhibitor such as a CRAC inhibitor such as at least one of Compound I, GSK 7975A, Compound II, and Compound III is administered to a person receiving a drug associated with a negative impact on pancreatic activity in the absence of any evidence in or from said person related to any sign of an impact of said drug on pancreatic activity, for example through an increase in blood amylase activity or blood lipase activity, or through manifestation of at least one pancreatitis symptom as disclosed herein.

In some embodiments the calcium channel inhibitor such as a CRAC inhibitor such as at least one of Compound I, GSK 7975A, Compound II, and Compound III is administered in a single composition with a drug associated with a negative impact on pancreatic activity. Accordingly, some embodiments disclosed herein relate to a composition comprising an intracellular Calcium signaling inhibitor and at least one drug associated with a negative impact on pancreatic activity. In some embodiments the at least one drug selected from the list consisting of: a steroid such as a corticosteroid, prednisolone, an HIV drug, didanosine, pentamidine, a diuretic, valproic acid, L-asparaginase, azathioprine, estrogen, a statin such as a cholesterol-lowering statin, an antihyperglycemic agent, metformin, a glipin such as vildagliptin and sitagliptin, an atypical antipsychotic, clozapine, risperidone, and olanzapine, azathioprine, and valproic acid.

In some embodiments, the intracellular Calcium signaling inhibitor of said composition is an SOC inhibitor. In some embodiments, the intracellular Calcium signaling inhibitor is a CRAC inhibitor. In some embodiments, said CRAC inhibitor comprises Compound I. In some embodiments, said CRAC inhibitor comprises GSK-7975A. In some embodiments, said CRAC inhibitor comprises Compound II. In some embodiments, said CRAC inhibitor comprises Compound III.

In some embodiments, the intracellular Calcium signaling inhibitor is delivered to achieve a tissue level concentration that is equal to, about, or greater than the in vitro $IC_{50}$ value determined for the compound. In some embodiments the Calcium signaling inhibitor is delivered to achieve a tissue level concentration that is 1.5×, 2×, 3×, 4×, 5×, 6×, 7×, 8×, 9×, 10×, 11×, 12×, 13×, 14×, 15×, 16×, 17×, 18×. 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, 46×, 47×, 48×, 49×, 50×, 51×, 52×, 53×, 54×, 55×, 56×, 57×, 58×, 59×, 60×, 61×, 62×, 63×, 64×, 65×, 66×, 67×, 68×. 69×, 70×, 71×, 72×, 73×, 74×, 75×, 76×, 77×, 78×, 79×, 80×, 81×, 82×, 83×, 84×, 85×, 86×, 87×, 88×, 89×, 90×, 91×, 92×. 93×, 94×, 95×, 96×. 97×, 98×, 99×, 100×, or any non-integer multiple ranging from 1× to 10× of the in vitro $IC_{50}$ value determined for the compound.

In some embodiments the Calcium signaling inhibitor is delivered to achieve a tissue level concentration that ranges from 1× to 100×, 2× to 80×, 3× to 60×, 4× to 50×, 5× to 45×. 6× to 44×, 7× to 43×, 8× to 43×, 9× to 41×, or 10× to 40×, or any non-integer within said range, of the in vitro $IC_{50}$ value determined for the compound.

In some embodiments the Calcium signaling inhibitor is delivered to achieve a tissue level concentration that is 1 µM, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 21 µM, 22 µM, 23 µM, 24 µM, 25 µM 26 µM, 27 µM, 28 µM, 29 µM, 30 µM, 31 µM, 32 µM 33 µM, 34 µM, 35 µM, 36 µM, 37 µM, 38 µM, 39 µM, 40 µM, 41µM, 42 µM. 43 µM, 44 µM, 45 µM, 46 µM, 47 µM, 48 µM, 49 µM, 50 µM, 51 µM, 52 µM, 53 µM, 54 µM, 55 µM, 56 µM, 57 µM, 58 µM, 59 µM, 60 µM, 61 µM, 62 µM, 63 µM, 64 µM, 65 µM, 66 µM, 67 µM, 68 µM, 69 µM, 70 µM, 71 µM, 72 µM, 73 µM, 74 µM, 75 µM, 76 µM, 77 µM, 78 µM, 79 µM, 80 µM, 81 µM, 82 µM, 83 µM, 84 µM, 85 µM, 86 µM, 87 µM. 88 µM, 89 µM, 90 µM, 91 µM, 92 µM, 93 µM, 94 µM, 95 µM, 96 µM, 97 µM, 98 µM, 99 µM, 100 µM, or any non-integer multiple ranging from about 1 µM to about 100 µM.

In some embodiments the Calcium signaling inhibitor is delivered to achieve a tissue level concentration that ranges from 1 µM to 100 µM, 2 µM to 90 µM, 3 µM to 80 µM, 4 µM to 70 µM, 5 µM to 60 µM, 6 µM to 50 µM, 7 µM to 40 µM, 8 µM to 30 µM, 9 µM to 20 µM, or 10 µM to 40 µM, or any integer or non-integer within said range.

In some embodiments the Calcium signaling inhibitor is delivered to achieve a tissue level concentration that ranges from 9.5 µM to 10.5 µM, 9 µM to 11 µM, 8 µM to 12 µM, 7 µM to 13 µM, 5 µM to 15 µM, 2 µM to 20 µM or µM to 50 µM, or any integer or non-integer within said range.

In some embodiments, the composition additionally comprises at least one of an excipient, a solubilizer, a surfactant, a disintegrant, and a buffer. In some embodiments the composition is a liquid or an emulsion. In some embodiments the composition is a liquid, a nanoparticle, a nanoparticle suspension, or a nanoparticle emulsion. In some embodiments the composition is a tablet.

Calcium Signaling and Viral Diseases

A viral disease occurs when an organism's body (the host) is invaded by pathogenic viruses. Infectious virus particles, called virions, attach to and enter susceptible cells of the host.

Calcium signaling modulates viral entry, production, and transmission in a host cell, thereby spreading the viral disease. By way of example, a host cell's calcium signaling is triggered by the viral disease through activation of STIM1- and Orai-mediated calcium entry, which further allows the virus to bud and replicate within the host cell.

Viral diseases are diverse and categorized by structural characteristics, such as genome type, virion shape, replication site, etc. By way of a specific non-limiting example, a viral disease comprises a hemorrhagic fever virus. In some aspects, a hemorrhagic fever virus is an arenavirus, a filovirus, a bunyavirus, a flavivirus, a rhabdovirus, or combinations thereof. Hemorrhagic fever viruses include, by way of non-limiting examples, Ebola virus, Marburg virus, Lassa virus, Junin virus, Rotavirus, West Nile virus, Zika virus, Coxsackievirus, Hepatitis B virus, Epstein Barr virus, dengue virus, Rift Valley virus, etc.

Disclosed herein are compositions and methods for the prophylactic amelioration of a viral disease and symptoms thereof, such as through the administration of a calcium channel inhibitor such as a CRAC inhibitor. In some embodiments a method of ameliorating the symptoms of a viral disease in a person is disclosed. In some embodiments a method of ameliorating the symptoms of a viral disease in a person is disclosed comprising the steps of identifying a person in need of prophylactic amelioration of symptoms of a viral disease, and administering an intracellular Calcium signaling inhibitor to said person at a dose sufficient to prophylactically ameliorate said symptoms.

In some embodiments, the common symptoms of a viral disease comprise fever or bleeding diathesis. In further embodiments, the symptoms of a viral disease comprise flushing of the face, flushing of the chest, petechiae, capillary leak, bleeding, swelling, edema, hypotension, shock, or combinations thereof. In even further embodiments, the symptoms of a viral disease comprise malaise, muscle pain, headache, vomiting, diarrhea, or combinations thereof.

In some embodiments, the intracellular Calcium signaling inhibitor is a SOC channel inhibitor. In some embodiments, the intracellular Calcium signaling inhibitor is a CRAC channel inhibitor. In some embodiments, the CRAC channel inhibitor comprises Compound I. In some embodiments, the CRAC channel inhibitor comprises GSK-7975A. In some embodiments, the CRAC channel inhibitor comprises Compound II. In some embodiments, the CRAC channel inhibitor comprises Compound III. In some embodiments, ameliorating symptoms of a viral disease further comprises administering an antiviral medication or a vaccine.

In some embodiments, the intracellular Calcium signaling inhibitor is delivered to achieve a tissue level concentration that is equal to, about, or greater than the in vitro ICs value determined for the compound. In some embodiments the Calcium signaling inhibitor is delivered to achieve a tissue level concentration that is 1.5×. 2×, 3×, 4×, 5×, 6×, 7×, 8×, 9×, 10×, 11×. 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×. 36×, 37×, 38×, 39×. 40×, 41×, 42×, 43×, 44×, 45×, 46×, 47×, 48×, 49×, 50×, 51×, 52×, 53×, 54×, 55×, 56×, 57×, 58×, 59×, 60×, 61×, 62×, 63×, 64×, 65×, 66×, 67×, 68×, 69×, 70×71×, 72×, 73×, 74×, 75×, 76×, 77×, 78×, 79×, 80×, 81×, 82×, 83×, 84×, 85×, 86×, 87×, 88×, 89×, 90×, 91×, 92×, 93×, 94×. 95×, 96×, 97×, 98×, 99×, 100×, or any non-integer multiple ranging from 1× to 100× of the in vitro ICS value determined for the compound.

In some embodiments the Calcium signaling inhibitor is delivered to achieve a tissue level concentration that ranges from 1× to 100×, 2× to 80×, 3× to 60×, 4× to 50×, 5× to 45×, 6× to 44×, 7× to 43×, 8× to 43×, 9× to 41×, or 0× to 40×, or any non-integer within said range, of the in vitro $IC_{50}$ value determined for the compound.

In some embodiments the Calcium signaling inhibitor is delivered to achieve a tissue level concentration that is 1 μM, 2 μM, 3 μM, 4 μM, 5 μM, 6 μM, 7 μM, 8 μM, 9 μM, 10 μM, 11μM, 12 μM, 13 μM, 14 μM, 15 μM, 16 μM, 17 μM, 18 μM, 19 μM, 20 μM, 21 μM, 22 μM, 23 μM, 24 μM, 25 μM, 26 μM, 27 μM, 28 μM, 29 μM, 30 μM, 31 μM, 32 μM, 33 μM, 34 μM, 35 μM, 36 μM, 37 μM, 38 μM, 39 μM, 40 μM, 41 μM, 42 μM, 43 μM, 44 μM, 45 μM, 46 μM, 47 μM, 48 μM 49 μM, 50 μM, 51 μM, 52 μM, 53 μM, 54 μM, 55 μM, 56 μM, 57 μM, 58 μM, 59 μM, 60 μM, 61 μM, 62 μM, 63 μM. 64 μM, 65 μM, 66 μM, 67 μM, 68 μM, 69 μM, 70 μM, 71 μM, 72 μM, 73 μM, 74 μM, 75 μM, 76 μM, 77 μM, 78 μM, 79 μM, 80 μM, 81 μM, 82 μM, 83 μM, 84 μM, 85 μM, 86 μM, 87 μM, 88 μM, 89 μM, 90 μM, 91 μM, 92 μM, 93 μM, 94 μM. 95 μM, 96 μM, 97 μM, 98 μM, 99 μM, 100 μM, or any non-integer multiple ranging from about 1 μM to about 100 μM.

In some embodiments the Calcium signaling inhibitor is delivered to achieve a tissue level concentration that ranges from 1 μM to 100 μM, 2 μM to 90 μM, 3 μM to 80 μM, 4 μM to 70 μM, 5M to 60 μM, 6 μM to 50 μM, 7 μM to 40 μM, 8 μM to 30 μM, 9 μM to 20 μM, or 10 μM to 40 μM, or any integer or non-integer within said range.

In some embodiments the Calcium signaling inhibitor is delivered to achieve a tissue level concentration that ranges from 9.5 μM to 10.5 μM, 9 μM to 11 μM. 8 μM to 12 μM, 7 μM to 13 μM 5 μM to 15 μM, 2 μM to 20 μM or 1 μM to 50 μM, or any integer or non-integer within said range.

In some embodiments the method comprises prophylactically ameliorating an acute viral disease symptom. In some embodiments the method comprises prophylactically ameliorating a chronic viral disease symptom.

Prophylactically ameliorating a symptom of a viral disease comprise reducing the severity, likelihood of occurrence, or duration of at least one symptom of the viral disease. Prophylactically ameliorating a symptom of a viral disease comprise reducing the severity, likelihood of occurrence, or duration of at least one symptom of the viral disease up to the point that said at least one symptom does not occur in the person. In some embodiments, prophylactically ameliorating a symptom of a viral disease comprise reducing the severity, likelihood of occurrence, or duration of 2, 3, 4, 5, 6, 7, 8, 9, or more than 9 symptoms of a viral disease, up to and including reducing the severity, likelihood of occurrence, or duration of all symptoms of the viral disease in a person, such as the symptoms of viral diseases disclosed herein. In some embodiments, rather than a person, the subject is a non-human mammal.

Calcium Signaling and Th17-Induced Diseases

T helper cells (Th cells) are critical to immune system functioning. Th cells regulate the immune system by releasing T cell cytokines, comprising chemokines, interferons, interleukins, lymphokines, tumor necrosis factor, or combinations thereof. T helper 17 cells (Th17) area subset of pro-inflammatory Th cells and are defined by their production of interleukin 17 (IL-17). Dysregulation of Th17 is associated with inflammatory and autoimmune disorders. Calcium signaling plays a crucial role in modulating Th17 differentiation.

Disclosed herein are compositions and methods for the prophylactic amelioration of Th17-induced disease and symptoms thereof, such as through the administration of a calcium channel inhibitor such as a CRAC inhibitor. In some embodiments a method of ameliorating the symptoms of Th17-induced diseases in a person is disclosed. In some embodiments a method of ameliorating the symptoms of Th17-induced disease in a person is disclosed comprising the steps of identifying a person in need of prophylactic amelioration of symptoms of a Th17-induced disease, and administering an intracellular Calcium signaling inhibitor to said person at a dose sufficient to prophylactically ameliorate said symptoms.

In some embodiments, the symptoms of Th17-induced disease comprise acute inflammation. Symptoms of inflammation in a person comprise localized reddening, swelling, heat, pain, stiffness, fever, chills, fatigue, headache, appetite loss, or combinations thereof. In some aspects, the symptoms occur on the body of the person, including the torso, arms, hands, fingers, legs, feet, toes, head, neck, bones, joints, throat, sinuses, eyes, or combinations thereof.

In other embodiments, Th17-induced disease comprises chronic inflammation or a chronic inflammatory disease. Chronic inflammatory diseases, by way of non-limiting examples, include hay fever, periodontitis, atherosclerosis, rheumatoid arthritis, or cancer.

In even further embodiments, Th17-induced diseases comprise an autoimmune disease. Autoimmune diseases are diseases in which the body's immune system attacks healthy cells. Autoimmune diseases occur in the heart, kidney, liver, lung, skin, endocrine glands, exocrine glands, digestive system, tissue, blood, nervous system, or vascular system. By way of non-limiting examples, autoimmune diseases include rheumatoid arthritis, lupus, celiac disease, psoriasis, Sjorgen's syndrome, polymyalgia rheumatica, multiple sclerosis, ankylosing spondylitis, type 1 diabetes, alopecia areata, vasculitis, temporal arteritis, etc.

In some embodiments, the intracellular Calcium signaling inhibitor is a SOC channel inhibitor. In some embodiments, the intracellular Calcium signaling inhibitor is a CRAC channel inhibitor. In some embodiments, the CRAC channel inhibitor comprises Compound I. In some embodiments, the CRAC channel inhibitor comprises GSK-7975A. In some embodiments, the CRAC channel inhibitor comprises Compound II. In some embodiments, the CRAC channel inhibitor comprises Compound III. In some embodiments, ameliorating symptoms of Th17-induced diseases further comprises administering an anti-inflammatory medication.

In some embodiments, the intracellular Calcium signaling inhibitor is delivered to achieve a tissue level concentration that is equal to, about, or greater than the in vitro $IC_{50}$ value determined for the compound. In some embodiments the Calcium signaling inhibitor is delivered to achieve a tissue level concentration that is 1.5×, 2×, 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, 46×, 47×, 48×, 49×, 50×, 51×, 52×, 53×, 54×, 55×, 56×, 57×, 58×, 59×, 60×, 61×, 62×, 63×, 64×, 65×, 66×, 67×, 68×, 69×, 70×, 71×, 72×, 73×, 74×, 75×, 76×, 77×, 78×, 79×, 80×, 81×, 82×, 83×, 84×, 85×, 86×, 87×, 88×, 89×, 90×, 91×, 92×, 93×, 94×, 95×, 96×, 97×, 98×, 99×, 100×, or any non-integer multiple ranging from 1× to 100× of the in vitro $IC_{50}$ value determined for the compound.

In some embodiments the Calcium signaling inhibitor is delivered to achieve a tissue level concentration that ranges from 1× to 100×, 2× to 80×, 3× to 60×, 4× to 50×, 5× to 45×, 6× to 44×, 7× to 43×, 8× to 43×, 9× to 41×, or 0× to 40×, or any non-integer within said range, of the in vitro $IC_{50}$ value determined for the compound.

In some embodiments the Calcium signaling inhibitor is delivered to achieve a tissue level concentration that is 1M, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 21 µM, 22 µM, 23 µM, 24 µM, 25 µM, 26 µM, 27 µM, 28 µM, 29 µM, 30M, 31 µM, 32 µM, 33 µM, 34 µM, 35 µM, 36 µM, 37 µM, 38 µM, 39 µM, 40 µM, 41 µM, 42 µM, 43 µM, 44 µM, 45 µM, 46 µM, 47 µM, 48 µM, 49 µM, 50 µM, 51 µM, 52 µM, 53 µM, 54 µM, 55 µM, 56 µM, 57 µM, 58 µM, 59 µM, 60 µM, 61 µM, 62 µM, 63 µM, 64 µM, 65 µM, 66 µM, 67 µM, 68 µM, 69 µM, 70 µM, 71 µM, 72 µM, 73 µM 74 µM, 75 µM, 76 µM, 77 µM, 78 µM, 79 µM, 8 µM, 8 µM, 82 µM, 83 µM, 84 µM, 85 µM, 86M, 87 µM, 88 µM, 89 µM, 90 µM, 91 µM, 92 µM, 93 µM, 94 µM, 95 µM, 96 µM, 97 µM, 98 µM, 99 µM, 100 µM, or any non-integer multiple ranging from about 1 µM to about 100 µM.

In some embodiments the Calcium signaling inhibitor is delivered to achieve a tissue level concentration that ranges from 1 µM to 100 µM, 2 µM to 90 µM, 3 µM to 80 µM, 4 µM to 70 µM, 5 µM to 60 µM, 6 µM to 50 µM, 7 µM to 40 µM, 8 µM to 30 µM, 9 µM to 2 µM, or 10 µM to 40 µM or any integer or non-integer within said range.

In some embodiments the Calcium signaling inhibitor is delivered to achieve a tissue level concentration that ranges from 9.5 µM to 10.5 µM, 9 µM to 11 µM, 8 µM to 12 µM, 7 µM to 13 µM, 5 µM to 15 µM, 2 µM to 20 µM or 1 µM to 50 µM, or any integer or non-integer within said range.

In some embodiments the method comprises prophylactically ameliorating an acute Th17-induced disease symptom. In some embodiments the method comprises prophylactically ameliorating a chronic Th17-induced disease symptom.

Prophylactically ameliorating a symptom of Th17-induced diseases comprise reducing the severity, likelihood of occurrence, or duration of at least one symptom of the Th17-induced disease. Prophylactically ameliorating a symptom of Th17-induced diseases comprise reducing the severity, likelihood of occurrence, or duration of at least one symptom of the Th7-induced disease up to the point that said at least one symptom does not occur in the person. In some embodiments, prophylactically ameliorating a symptom of Th17-induced diseases comprise reducing the severity, likelihood of occurrence, or duration of 2, 3, 4, 5, 6, 7, 8, 9, or more than 9 symptoms of a Th17-induced disease, up to and including reducing the severity, likelihood of occurrence, or duration of all symptoms of the Th17-induced disease in a person, such as the symptoms of Th17-induced diseases disclosed herein. In some embodiments, rather than a person, the subject is a non-human mammal.

Certain Terminology

Unless defined otherwise, all technical and scientific terms used herein have the same meaning as is commonly understood to which the claimed subject matter pertains. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

The terms "kit" and "article of manufacture" are used as synonyms.

The term "subject" or "patient" encompasses mammals and non-mammals. Examples of mammals include, but are not limited to, any member of the Mammalian class: humans, non-human primates such as chimpanzees, and other apes and monkey species: farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "target protein" refers to a protein or a portion of a protein capable of being bound by, or interacting with a compound described herein, such as a compound with a structure from the group of Compound A. In certain embodiments, a target protein is a STIM protein. In certain embodiments, a target protein is an Orai protein.

As used herein, "STIM protein" includes but is not limited to, mammalian STIM-1, such as human and rodent (e.g., mouse) STIM-1, *Drosophila melanogaster* D-STIM, *C. elegans* C-STIM, *Anopheles gambiae* STIM and mammalian STIM-2, such as human and rodent (e.g., mouse) STIM-2. (see paragraphs 102111 through 10270 of US 2007/0031814, as well as Table 3 of US 2007/0031814, herein incorporated by reference) As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum).

As used herein, an "Orai protein" includes Orai1 (SEQ ID NO: 1 as described in WO 07/081804), Orai2 (SEQ ID NO: 2 as described in WO 07/081804), or Orai3 (SEQ ID NO: 3 as described in WO 07/081804). Orai1 nucleic acid sequence corresponds to GenBank accession number NM_032790, Orai2 nucleic acid sequence corresponds to GenBank accession number BC069270 and Orai3 nucleic acid sequence corresponds to GenBank accession number NM_152288. As used herein, Orai refers to any one of the Orai genes, e.g., Orai1, Orai2, Orai3 (see Table 1 of WO 07/081804). As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum).

The term "fragment" or "derivative" when referring to a protein (e.g. STIM, Orai) means proteins or polypeptides which retain essentially the same biological function or activity in at least one assay as the native protein(s). For example, the fragments or derivatives of the referenced protein maintains at least about 50% of the activity of the native proteins, at least 75%, at least about 95% of the activity of the native proteins, as determined e.g. by a calcium influx assay.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "modulate," as used herein, means to interact with a target protein either directly or indirectly so as to alter the activity of the target protein, including, by way of example only, to inhibit the activity of the target, or to limit or reduce the activity of the target.

As used herein, the term "modulator" refers to a compound that alters an activity of a target. For example, a modulator can cause an increase or decrease in the magnitude of a certain activity of a target compared to the magnitude of the activity in the absence of the modulator. In certain embodiments, a modulator is an inhibitor, which decreases the magnitude of one or more activities of a target. In certain embodiments, an inhibitor completely prevents one or more activities of a target.

As used herein. "modulation" with reference to intracellular calcium refers to any alteration or adjustment in intracellular calcium including but not limited to alteration of calcium concentration in the cytoplasm and/or intracellular calcium storage organelles, e.g., endoplasmic reticulum, and alteration of the kinetics of calcium fluxes into, out of and within cells. In aspect, modulation refers to reduction.

As used herein, the term "target activity" refers to a biological activity capable of being modulated by a modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "inhibits". "inhibiting", or "inhibitor" of SOC channel activity or CRAC channel activity, as used herein, refer to inhibition of store operated calcium channel activity or calcium release activated calcium channel activity.

The term "acceptable" with respect to a formulation, composition or ingredient, as used herein, means having no persistent detrimental effect on the general health of the subject being treated.

The term "pharmaceutically acceptable," as used herein, refers a material, such as a carrier, diluent, or formulation, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutical combination" as used herein, means a product that results from the mixing or combining of more than one active ingredient and includes both fixed and non-fixed combinations of the active ingredients. The term "fixed combination" means that one active ingredient, e.g. a compound with a structure from the group of Compound A and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound with a structure from the group of Compound A, described herein with other chemical components, such as carriers, stabilizers, diluents, surfactants, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, subcutaneous, intramuscular, pulmonary and topical administration.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition that includes a compound with a structure from the group of Compound A, required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "co-administration" or the like, as used herein, are meant to encompass administration of the selected therapeutic agents to a single patient, and are intended to include treatment regimens in which the agents are administered by the same or different route of administration or at the same or different time.

The term "carrier," as used herein, refers to relatively nontoxic chemical compounds or agents that facilitate the incorporation of a compound into cells or tissues.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (19%). Metabolites of the compounds disclosed herein can be identified either by administration of compounds to a host and analysis of tissue samples from the host, or by incubation of compounds with hepatic cells in vitro and analysis of the resulting compounds.

"Bioavailability" refers to the percentage of the weight of the compound disclosed herein (e.g. a compound from the group of Compound A) that is delivered into the general circulation of the animal or human being studied. The total exposure (AUC(0–∞)) of a drug when administered intravenously is usually defined as 100% bioavailable (F %). "Oral bioavailability" refers to the extent to which a compound disclosed herein, is absorbed into the general circulation when the pharmaceutical composition is taken orally as compared to intravenous injection.

"Blood plasma concentration" refers to the concentration of a compound with a structure from the group of Compound A, in the plasma component of blood of a subject. It is understood that the plasma concentration of compounds described herein may vary significantly between subjects, due to variability with respect to metabolism and/or possible interactions with other therapeutic agents. In accordance with one embodiment disclosed herein, the blood plasma concentration of the compounds disclosed herein may vary from subject to subject. Likewise, values such as maximum plasma concentration (Cmax) or time to reach maximum plasma concentration (Tmax), or total area under the plasma concentration time curve (AUC(0–∞)) may vary from subject to subject. Due to this variability, the amount necessary to constitute "a therapeutically effective amount" of a compound may vary from subject to subject.

As used herein, "calcium homeostasis" refers to the maintenance of an overall balance in intracellular calcium levels and movements, including calcium signaling, within a cell.

As used herein, "intracellular calcium" refers to calcium located in a cell without specification of a particular cellular location. In contrast, "cytosolic" or "cytoplasmic" with reference to calcium refers to calcium located in the cell cytoplasm.

As used herein, an effect on intracellular calcium is any alteration of any aspect of intracellular calcium, including but not limited to, an alteration in intracellular calcium levels and location and movement of calcium into, out of or within a cell or intracellular calcium store or organelle. For example, an effect on intracellular calcium can be an alteration of the properties, such as, for example, the kinetics, sensitivities, rate, amplitude, and electrophysiological characteristics, of calcium flux or movement that occurs in a cell or portion thereof. An effect on intracellular calcium can be an alteration in any intracellular calcium-modulating process, including, store-operated calcium entry, cytosolic calcium buffering, and calcium levels in or movement of calcium into, out of or within an intracellular calcium store. Any of these aspects can be assessed in a variety of ways including, but not limited to, evaluation of calcium or other ion (particularly cation) levels, movement of calcium or other ion (particularly cation), fluctuations in calcium or other ion (particularly cation) levels, kinetics of calcium or other ion (particularly cation) fluxes and/or transport of calcium or other ion (particularly cation) through a membrane. An alteration can be any such change that is statistically significant. Thus, for example if intracellular calcium in a test cell and a control cell is said to differ, such difference can be a statistically significant difference.

As used herein, "involved in" with respect to the relationship between a protein and an aspect of intracellular calcium or intracellular calcium regulation means that when expression or activity of the protein in a cell is reduced, altered or eliminated, there is a concomitant or associated reduction, alteration or elimination of one or more aspects of intracellular calcium or intracellular calcium regulation. Such an alteration or reduction in expression or activity can occur by virtue of an alteration of expression of a gene encoding the protein or by altering the levels of the protein. A protein involved in an aspect of intracellular calcium, such as, for example, store-operated calcium entry, thus, can be one that provides for or participates in an aspect of intracellular calcium or intracellular calcium regulation. For example, a protein that provides for store-operated calcium entry can be a STIM protein and/or an Orai protein.

As used herein, a protein that is a component of a calcium channel is a protein that participates in multi-protein complex that forms the channel.

As used herein, "basal" or "resting" with reference to cytosolic calcium levels refers to the concentration of calcium in the cytoplasm of a cell, such as, for example, an unstimulated cell, that has not been subjected to a condition that results in movement of calcium into or out of the cell or within the cell. The basal or resting cytosolic calcium level can be the concentration of free calcium (i.e., calcium that is not bound to a cellular calcium-binding substance) in the cytoplasm of a cell, such as, for example, an unstimulated cell, that has not been subjected to a condition that results in movement of calcium into or out of the cell.

As used herein, "movement" with respect to ions, including cations, e.g., calcium, refers to movement or relocation, such as for example flux, of ions into, out of, or within a cell. Thus, movement of ions can be, for example, movement of ions from the extracellular medium into a cell, from within a cell to the extracellular medium, from within an intracellular organelle or storage site to the cytosol, from the cytosol into an intracellular organelle or storage site, from one intracellular organelle or storage site to another intracellular organelle or storage site, from the extracellular medium into an intracellular organelle or storage site, from an intracellular organelle or storage site to the extracellular medium and from one location to another within the cell cytoplasm.

As used herein, "cation entry" or "calcium entry" into a cell refers to entry of cations, such as calcium, into an intracellular location, such as the cytoplasm of a cell or into the lumen of an intracellular organelle or storage site. Thus, cation entry can be, for example, the movement of cations into the cell cytoplasm from the extracellular medium or from an intracellular organelle or storage site, or the movement of cations into an intracellular organelle or storage site from the cytoplasm or extracellular medium. Movement of calcium into the cytoplasm from an intracellular organelle or storage site is also referred to as "calcium release" from the organelle or storage site.

As used herein, "protein that modulates intracellular calcium" refers to any cellular protein that is involved in regulating, controlling and/or altering intracellular calcium. For example, such a protein can be involved in altering or adjusting intracellular calcium in a number of ways, including, but not limited to, through the maintenance of resting or basal cytoplasmic calcium levels, or through involvement in a cellular response to a signal that is transmitted in a cell through a mechanism that includes a deviation in intracellular calcium from resting or basal states. In the context of a "protein that modulates intracellular calcium," a "cellular" protein is one that is associated with a cell, such as, for example, a cytoplasmic protein, a plasma membrane-associated protein or an intracellular membrane protein. Proteins that modulate intracellular calcium include, but are not limited to, ion transport proteins, calcium-binding proteins and regulatory proteins that regulate ion transport proteins.

As used herein, the term "ameliorate" means to reduce, prevent, alleviate, and/or lessen the impact of a disease, symptom or condition, to bring about improvement in a disease or condition or at least a partial relief of symptoms associated with a disease or condition up to and including complete reduction such that said impact is zero or effectively zero.

As used herein, "cell response" refers to any cellular response that results from ion movement into or out of a cell or within a cell. The cell response may be associated with any cellular activity that is dependent, at least in part, on ions such as, for example, calcium. Such activities may include, for example, cellular activation, gene expression, endocytosis, exocytosis, cellular trafficking and apoptotic cell death.

As used herein. "immune cells" include cells of the immune system and cells that perform a function or activity in an immune response, such as, but not limited to, T-cells, B-cells, lymphocytes, macrophages, dendritic cells, neutrophils, eosinophils, basophils, mast cells, plasma cells, white blood cells, antigen presenting cells and natural killer cells.

As used herein, "cytokine" refers to small soluble proteins secreted by cells that can alter the behavior or properties of the secreting cell or another cell. Cytokines bind to cytokine receptors and trigger a behavior or property within the cell, for example, cell proliferation, death or differentiation. Exemplary cytokines include, but are not limited to, interleukins (e.g., IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7.1 (also known as CD80), B7.2 (also known as B70, CD86), TNF family members (TNF-α, TNF-β, LT-β, CD40 ligand, Fas ligand, CD27 ligand, CD30 ligand, 4-1BBL, Trail), and MIF.

"Store operated calcium entry" or "SOCE" refers to the mechanism by which release of calcium ions from intracellular stores is coordinated with ion influx across the plasma membrane.

"Selective inhibitor of SOC channel activity" means that the inhibitor is selective for SOC channels and does not substantially affect the activity of other types of ion channels.

"Selective inhibitor of CRAC channel activity" means that the inhibitor is selective for CRAC channels and does not substantially affect the activity of other types of ion channels and/or other SOC channels.

As used herein, the term 'calcium' may be used to refer to the element or to the divalent cation $Ca^{2+}$.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: CRAC Channel Inhibition by GSK-7975A Blocks Necrosis in Mouse and Human Pancreatic Acinar Cells Mouse Pancreatic Acinar Cells (PACs) were extracted and incubated with either a carrier (control) or with natural bile acid TLCS (taurolithocholic acid 3-sulfate) in the absence or presence of GSK-7975A. Cells were contacted with propidium iodide to assay for cell necrosis. TLCS treatment to individual cells in vitro mimics the effect of a gall stone or other blockage in pancreatic secretion in vivo.

As indicated in FIG. 1A, TLCS induced necrosis in about 45% of cells during the time period of the experiment. Addition of GSK-7975A at 10 μM reduced this percent necrosis by half, to about 23%. The asterisk indicates a statistically significant change. Cells not treated with TLCS demonstrated a necrosis of about 10%. This result demonstrates that GSK-7975A reduces the necrosis-inducing effect of TLCS on mouse PACs.

Human PACs were extracted and incubated with either a carrier (control) or with natural bile acid TLCS in the absence or presence of GSK-7975A. Cells were contacted with propidium iodide to assay for cell necrosis. TLCS treatment to individual cells in vitro mimics the effect of a gall stone or other blockage in pancreatic secretion in vivo.

Figure 1B:
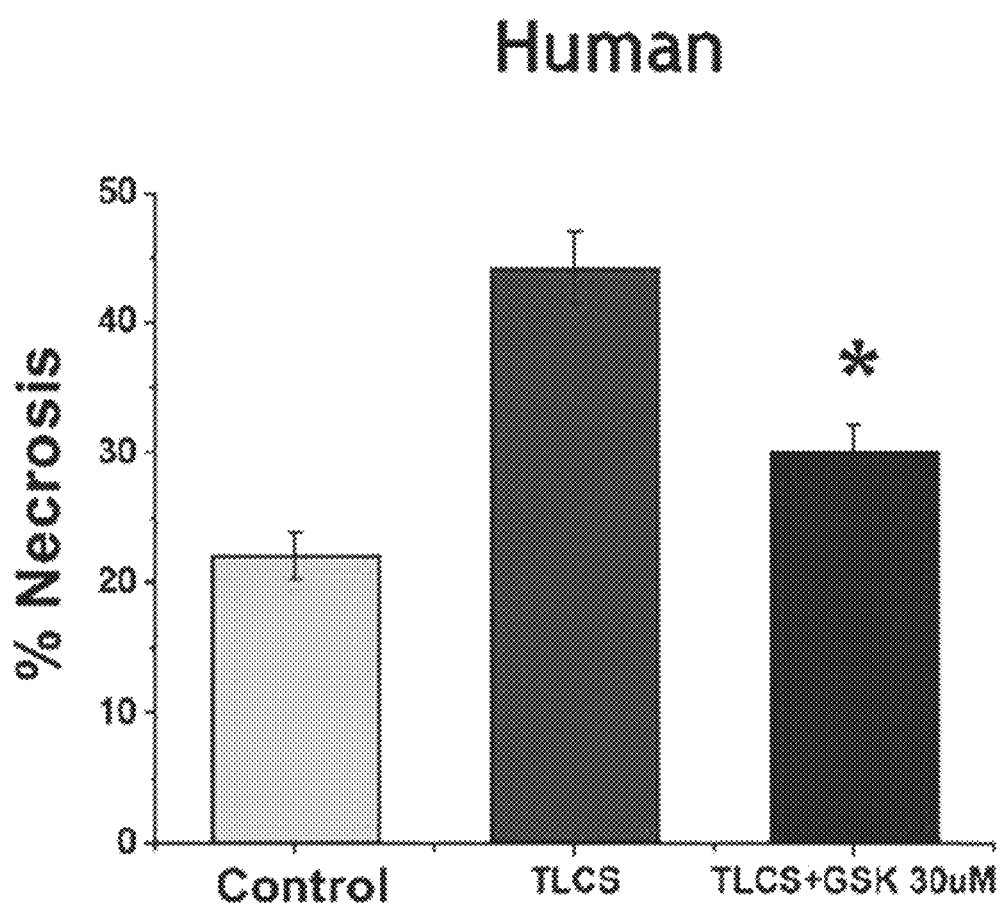
FIG. 1B shows human Acinar cell necrosis upon treatment with TLCS.

As indicated in FIG. 1B, TLCS induced necrosis in about 45% of cells during the time period of the experiment. Addition of GSK-7975A at 10 μM reduced this percent necrosis to about 30%. The asterisk indicates a statistically significant change. Cells not treated with TLCS demonstrated necrosis at about 23%. This result demonstrates that GSK-7975A reduces the necrosis-inducing effect of TLCS on human PACs.

Example 2: CRAC Channel Inhibitor (GSK-7975A) Blocks Histopathological Changes in Mouse Models of AP Mouse acute pancreatitis models were used to evaluate the effect of a CRAC inhibitor on pancreas histopathological progression. Caerulein is used to hyper-stimulate CCK receptors in the normal Calcium signaling pathway in the mouse pancreas. TLCS is used to induce acute pancreatitis through simulation of an excess of bile acid, as would be experienced in a gallstone induced acute pancreatitis. Fatty acid ethyl esters (FAEE) are used to simulate alcohol-induced acute pancreatitis. Mice were treated with the acute pancreatitis agent (Caerulin, FIG. 2A, TLCS. FIG. 2B or FAEE, FIG. 2C) alone or with the CRAC inhibitor GSK-7975A at either 0x or 40× the $IC_{50}$ of the CRAC inhibitor.

It is observed that GSK-7975A substantially reduces the total histopathology score of treated mice relative to mice treated with the agent in the absence of the CRAC inhibitor. This effect was statistically significant and substantially more pronounced at 40× $IC_{50}$ that ant 10×$IC_{50}$, but was observed at the lower concentration as well. The asterisk indicates a statistically significant change. GSK-7975A at doses that achieve tissue levels 10- or 40-fold above its in vitro $IC_{50}$ value produces significant reductions in pancreatic histopathology.

Figure 2A:
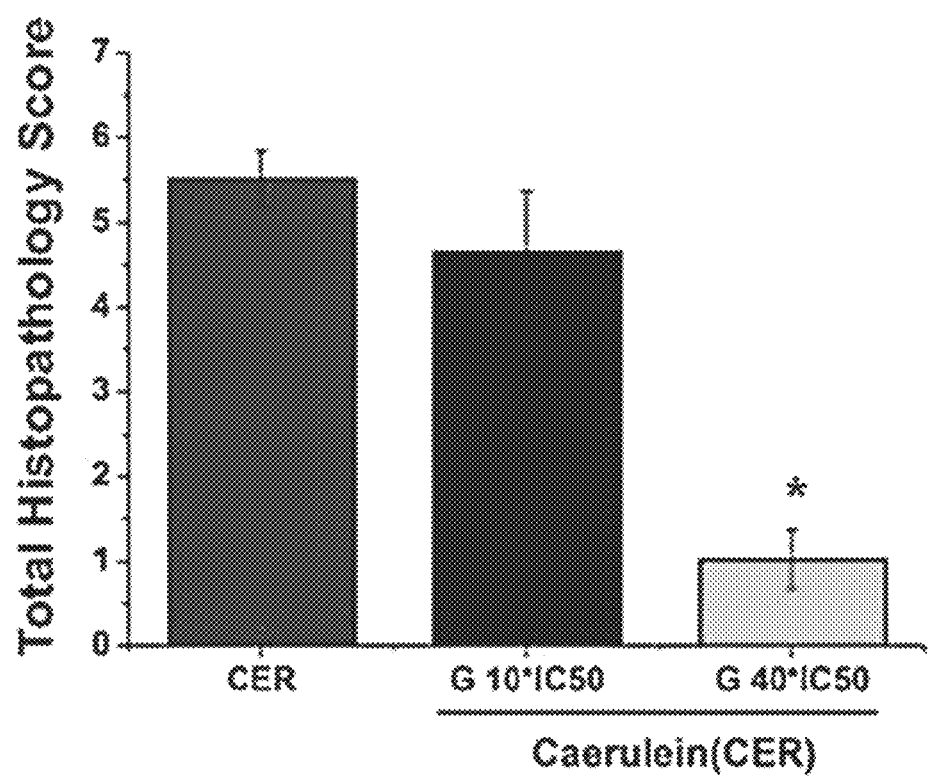
FIG. 2A shows histopathology scores for Caelurin-induced acute pancreatitits.
Figure 2B:
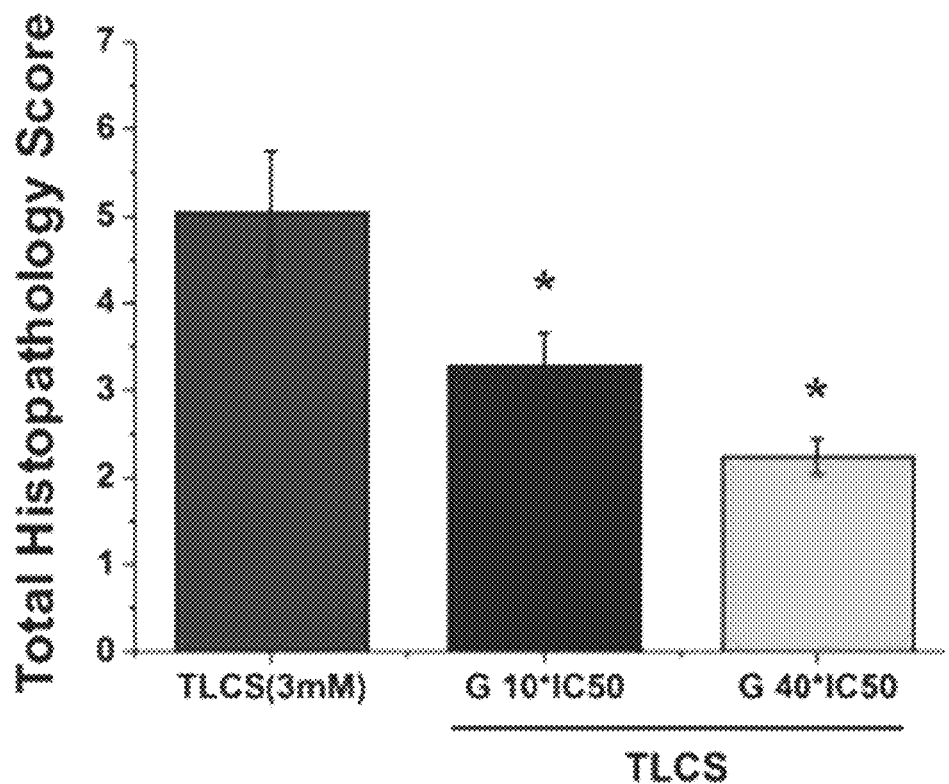
FIG. 2B shows histopathology scores for TLCS-induced acute pancreatitits.
Figure 2C:
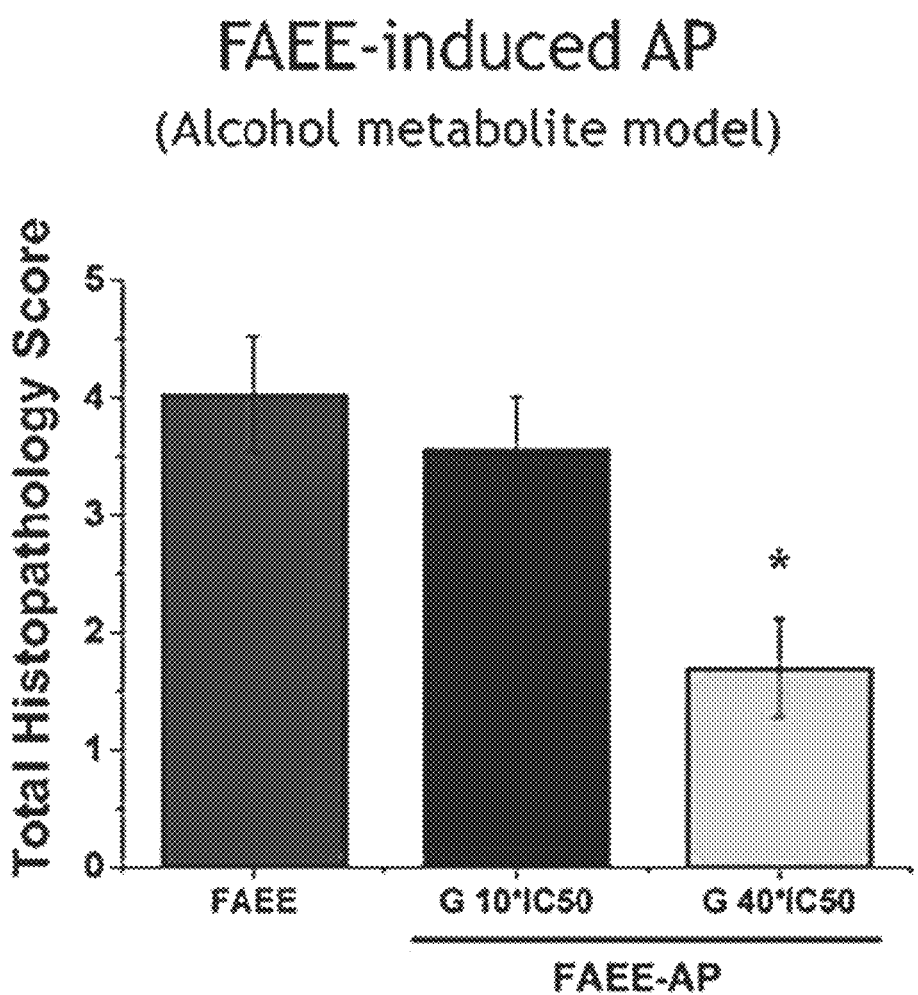
FIG. 2C shows histopathology scores for FAEE-induced acute pancreatitits.

The results presented in FIGS. 2A, 2B and 2C indicate that a CRAC inhibitor can ameliorate the histopathological symptoms of acute pancreatitis. This effect is observed independent of the inducing agent or the type of acute pancreatitis being modeled.

Example 3: Compound I and GSK-7975A Inhibit CRAC Channels

Figure 3A:
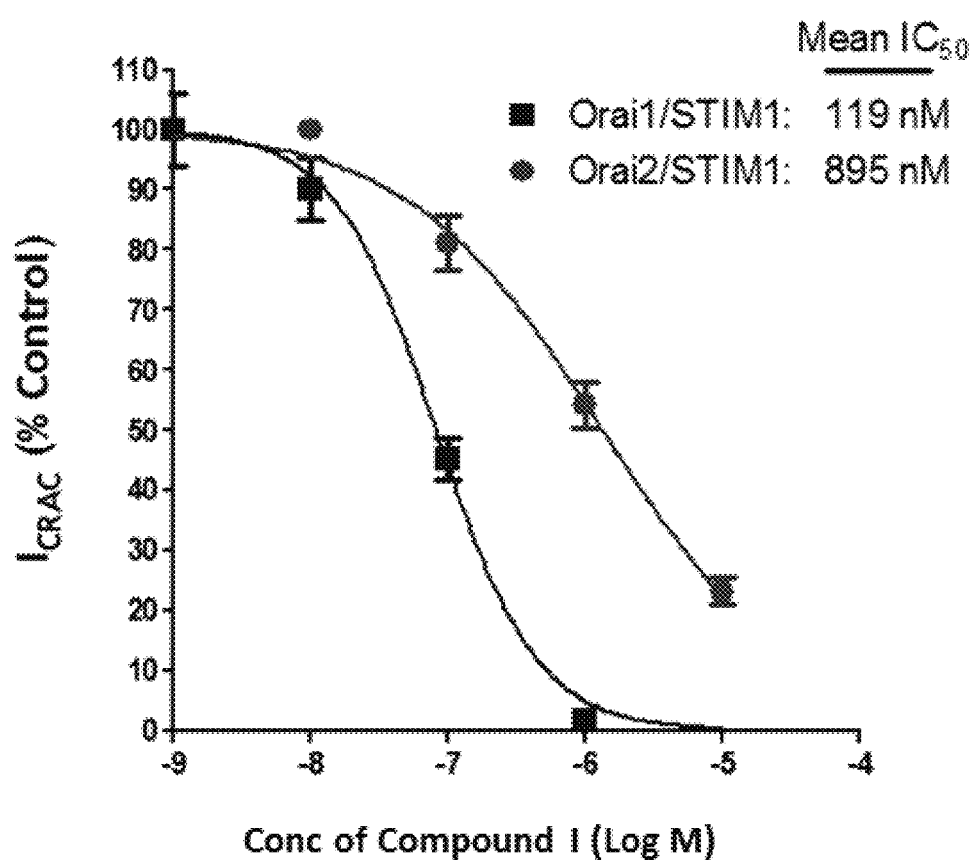
FIG. 3A shows an $IC_{50}$ determination for N-(5-(6-chloro-2,2-difluorobenzo[d][1,3]dioxol-5-yl)pyrazin-2-yl)-2-fluoro-6-methylbenzamide ("Compound I").

Compound I and GSK-7975A were assayed for their inhibitory effect on CRAC channels. Channels comprising Orai1/STIM1 and Orai2/STIM1 were assayed. As presented in FIG. 3A, it was determined that Compound I inhibited Orai1/STIM1 channels with a mean $IC_{50}$ of 119 nM, and Orai2/STIM1 channels with a mean $IC_{50}$ of 895 nM. As presented in FIG. 3B, it was determined that GSK-7975A inhibited Orai1/STIM1 channels with a mean $IC_{50}$ of 398 nM, and Orai2/STIM1 channels with a mean $IC_{50}$ of 1453 nM. Compound I is about 4-fold more potent on Orai1-type CRAC channels compared to GSK-7975A. Both compounds are more potent on Orai1 than Orai2-type CRAC channels.

These results indicate that the effect observed for GSK-7975A on Calcium signaling is generalizeable to CRAC inhibitors, and that CRAC inhibitors other than GSK-7975A may outperform GSK-7975A on some parameters.

Figure 4A:
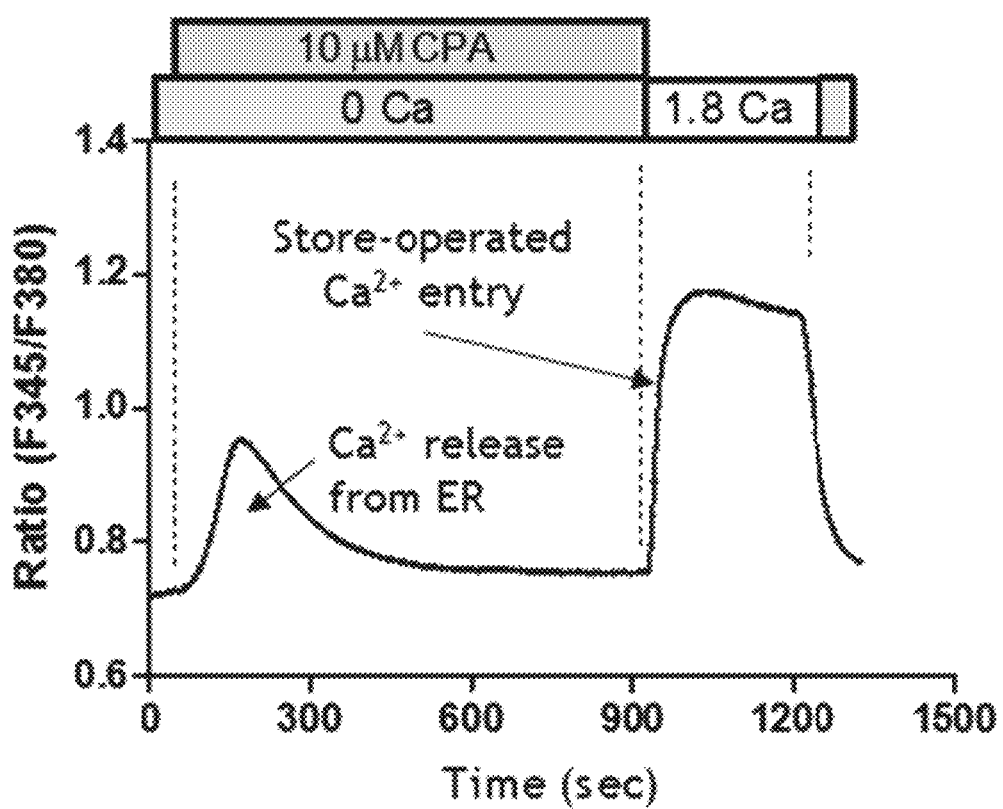
FIG. 4A shows Calcium uptake in the absence of a CRAC inhibitor.
Figure 4B:
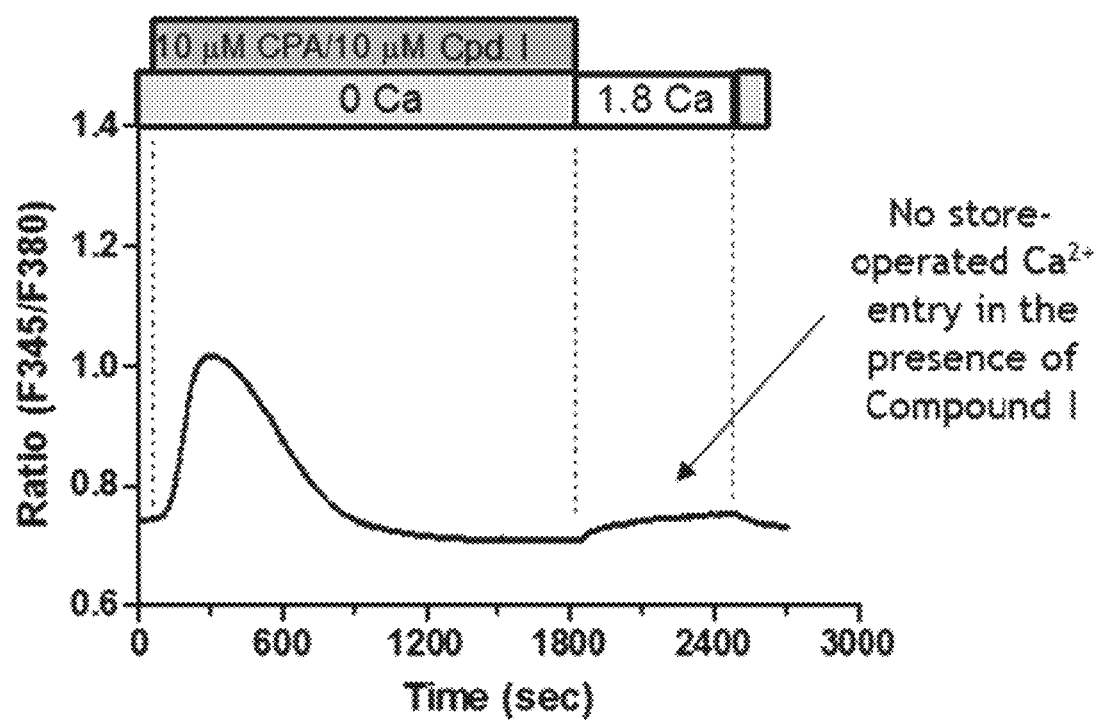
FIG. 4B shows Calcium uptake in the presence of a CRAC inhibitor.

Example 4: Compound I Blocks Store-Operated $Ca^{2+}$ Entry (SOCE) in Mouse Pancreatic Acinar Cells Mouse PACs were isolated and assayed for the effect of CRAC inhibitors on calcium re-uptake into the ER. Cells were treated with cyclopiazonic acid (CPA) alone (FIG. 4A) or in combination with the CRAC inhibitor Compound I (FIG. 4B) to activate CRAC channels to release $Ca^{2+}$ At 15 minutes following Calcium release, cells were provided with an excess of Calcium and monitored for Calcium uptake into the ER. It is observed that the CRAC inhibitor-treated cells do not demonstrate reuptake of Calcium.

This result indicates that CRAC inhibitors may block the cell's ability to reload its ER with Calcium for successive rounds of signaling.

Figure 5A:
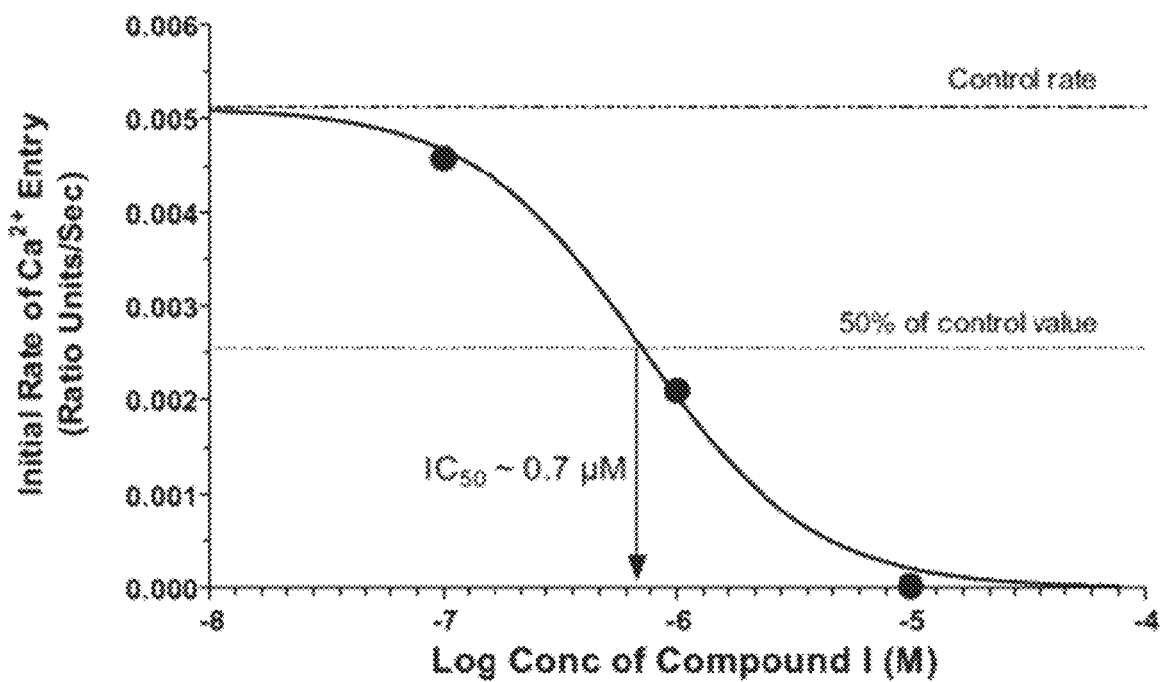
FIG. 5A shows Calcium entry in the presence of CRAC inhibitor Compound I.
Figure 5B:
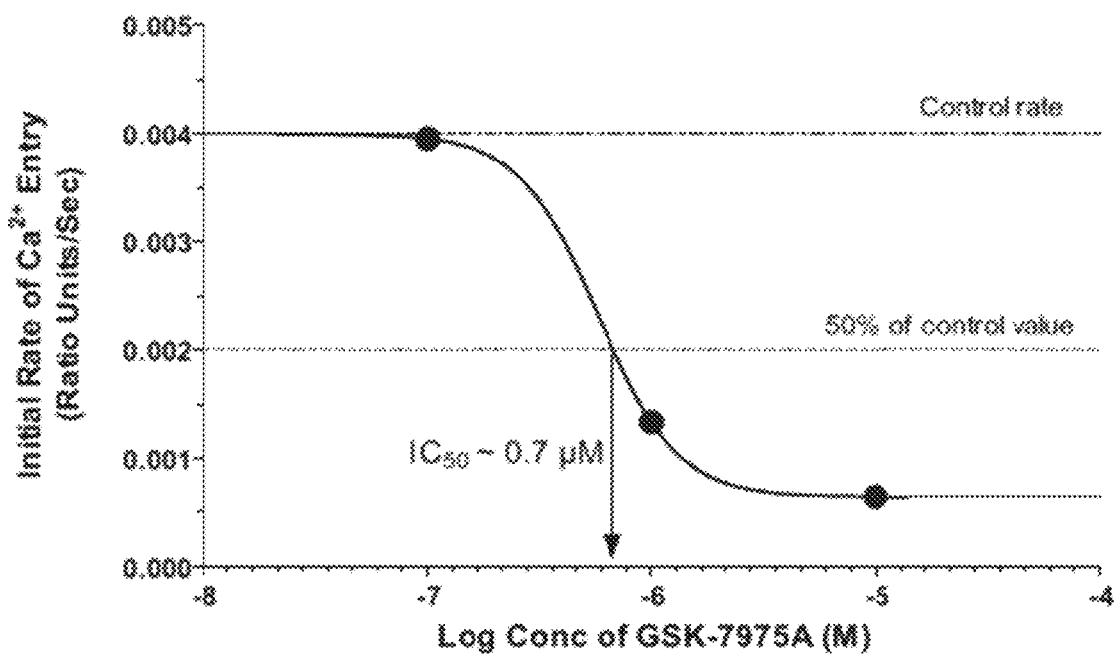
FIG. 5B shows Calcium entry in the presence of CRAC inhibitor GSK-7975A.

Example 5: Compound I and GSK-7975A Block SOCE in Mouse Pancreatic Acinar Cells in a Dose-Dependent Manner Mouse PACs were treated with CRAC inhibitors Compound I (FIG. 5A) or GSK-7975A (FIG. 5B) and monitored for their rate of Calcium uptake. Both CRAC inhibitors reduced the rate of store-operated Calcium entry into the ER to 50% of control levels upon treatment with 700 nM of inhibitor. Compound I blocks 100% of reuptake at 10 mM.

This example demonstrates that multiple CRAC inhibitors each act to inhibit SOCE in mammalian PACs.

Figure 6A:
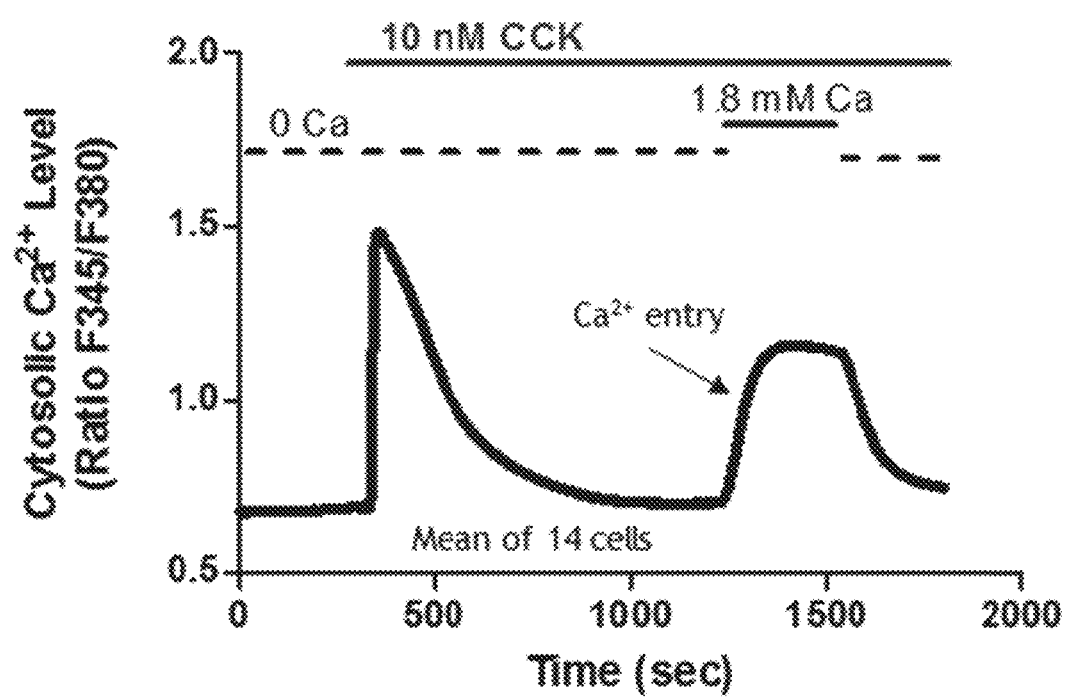
FIG. 6A shows Calcium entry in the absence of a CRAC inhibitor.
Figure 6B:
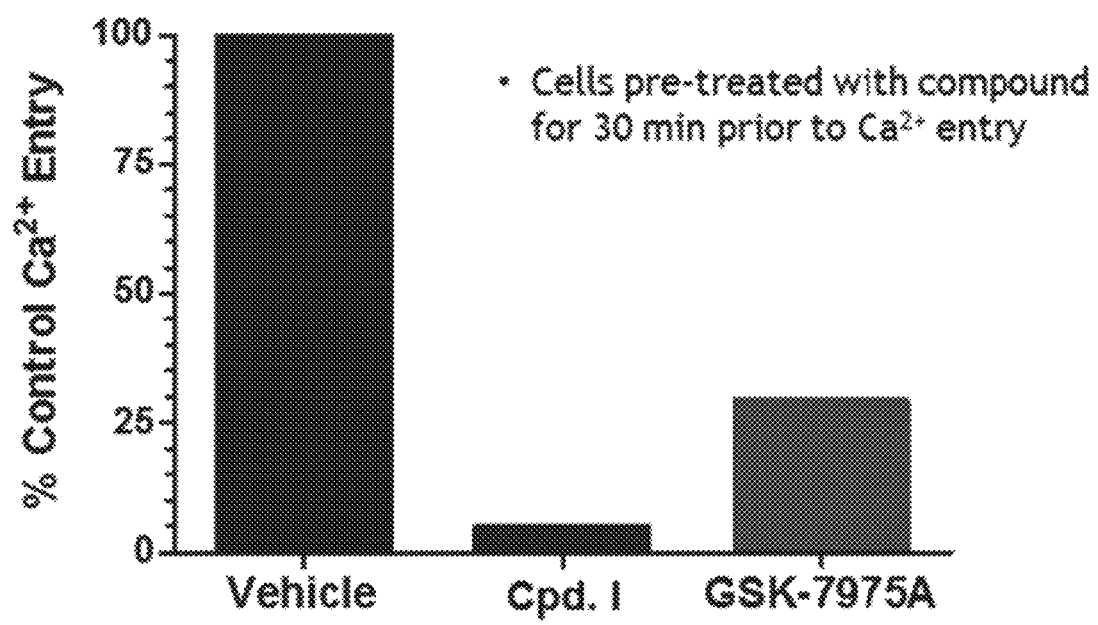
FIG. 6B shows relative Calcium entry in the presence of CRAC inhibitors Compound I and GSK-7975A compared to a control.

Example 6: Compound I Blocks CCK-Induced $Ca^{2+}$ Entry in Mouse Pancreatic Acinar Mouse PACs were monitored for their Calcium uptake upon treatment with CCK at 10 nM. Cells were treated with CCK and then provided with 1.8 mM Calcium and Calcium reuptake was monitored. It was observed that cells pretreated with CRAC inhibitors (FIG. 6B) demonstrated substantially reduced Calcium re-uptake compared to untreated cells (FIG. 6A). Compound I pretreatment reduced Calcium re-uptake to near 0% of the control. GSK-7975A reduced calcium reuptake to about 30% of the control.

These results indicate than CRAC inhibitors may be efficacious in reducing overactive Calcium signaling in PACs.

Example 7: Compound I Inhibits Multiple Cytokines

Compound I was tested for its inhibitory effect on a number of cytokines. Cytokines INF-gamma, IL-4, and IL-4 receptors of which are expressed on Acinar cells, cytokines IL-1beta, IL-6, IL-10 and TNF-alpha, expressed in Acinar cells, and IL-2 and IL-7, cytokines important in T-cell function, were tested for an inhibitory effect of the CRAC inhibitor Compound I. T cells in bulk human PBMCs were stimulated with plate-bound anti-CD3/anti-CD28 in buffer+ 10% serum for 48 hrs. Released cytokines were measured by Luminex at Millipore. The results are presented in FIG. 7. In human PBMCs, Compound I potently inhibits release of multiple cytokines which play important roles in T cells.

These cytokine data, together with the PAC data, support the conclusion that Compound I has a dual effect in acute pancreatitis, inhibiting both immune cell and pancreatic acinar cell signaling pathways and death.

Figure 8A:
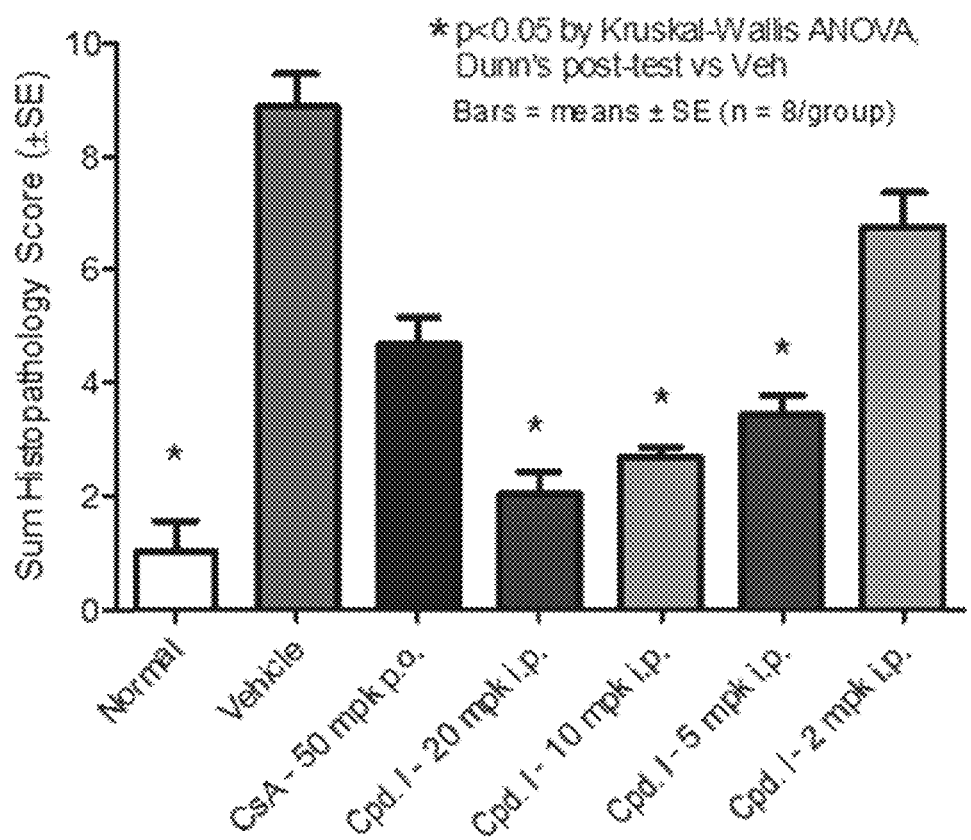
FIG. 8A shows histopathology scores for a range of concentrations of Compound I.
Figure 8B:
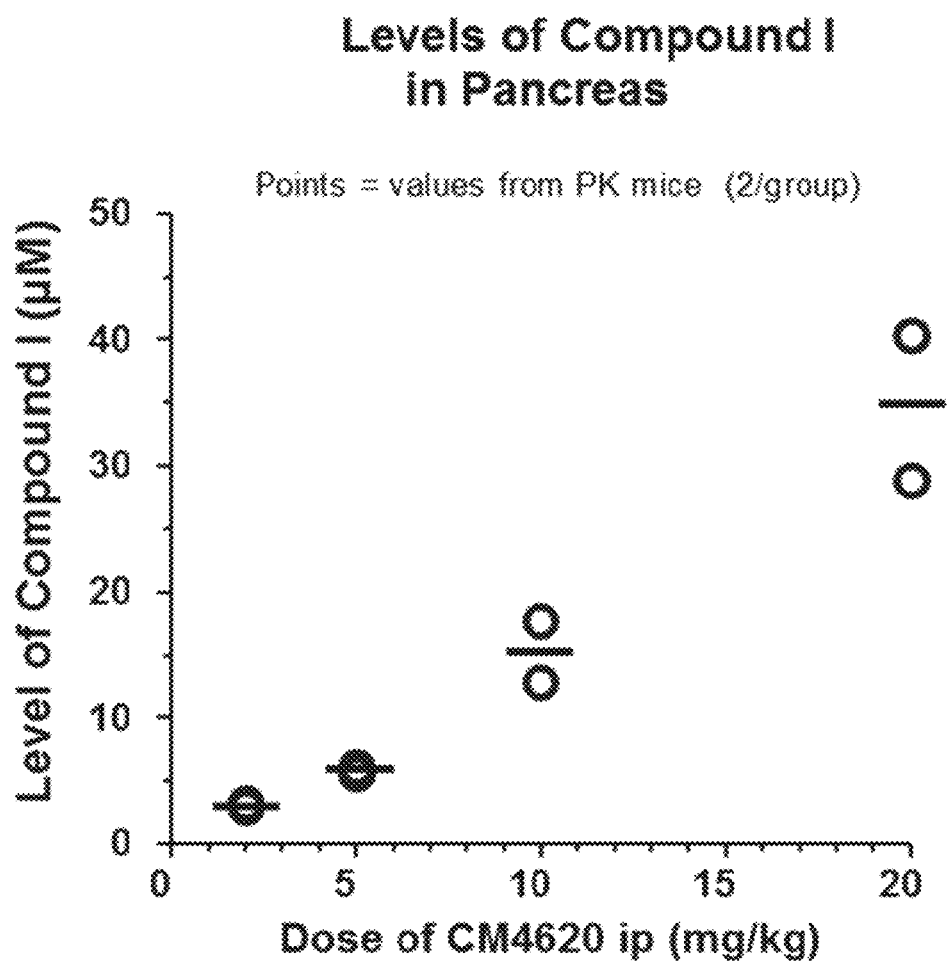
FIG. 8B shows Compound I concentrations in the pancreas as a function of dose.

Example 8: Compound I Shows Robust Efficacy in a Mouse Calcinurin Model of Acute Pancreatitis Mice were treated with a CRAC inhibitor or a vehicle prophylactically, and then challenged with CCK to trigger acute pancreatitis. Compound I, administered i.p. prophylactically, produced significant and dose-dependent reductions in caerulein-induced pathology in the mouse pancreas ($C_57B6$ mice). This effect was significantly below the positive control CsA at 5 mg/kg, and increased in a dose-dependent manner. See FIG. 8A. The treatment demonstrated a dose-proportional increase of Compound I levels in the pancreas after i.p. injection (see FIG. 8B), which corresponded to the positive results in FIG. 8A, above.

These results indicate that CRAC administration, prior to or concurrently with a second drug suspected of triggering acute pancreatitis or increasing the risk of acute pancreatitis, may prophylactically protect against or reduce the risk of acute pancreatitis.

Figure 9A:
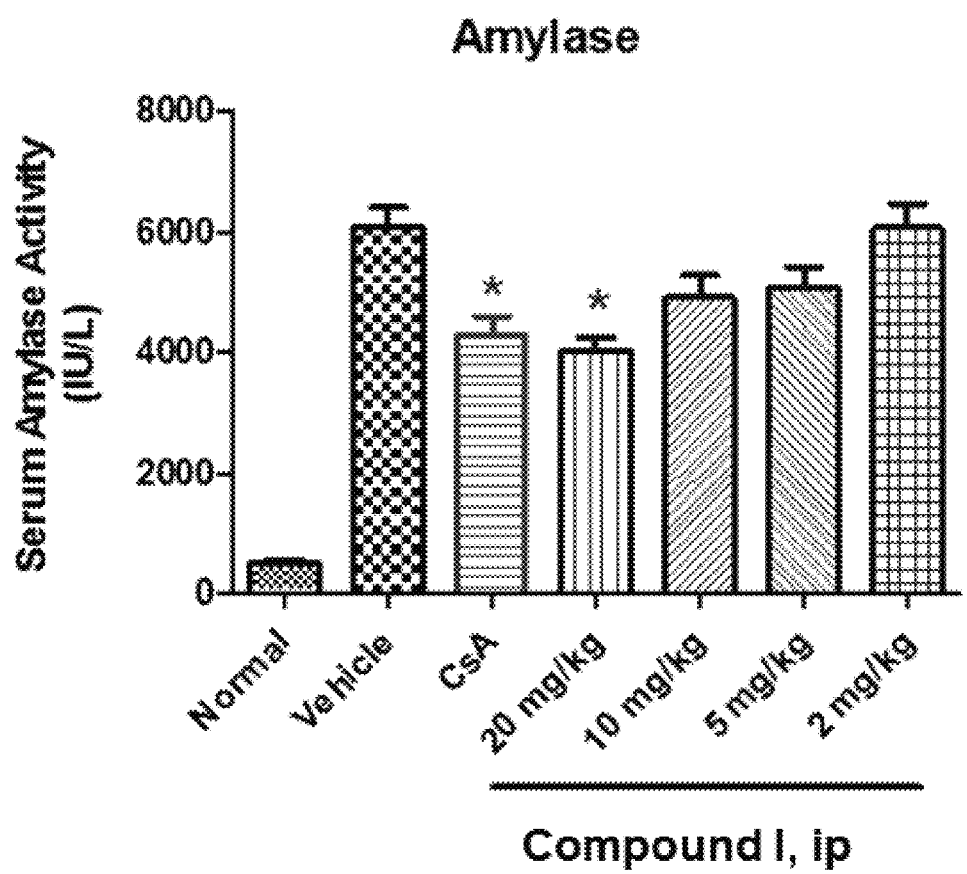
FIG. 9A shows serum Amylase levels in uninduced (normal) mice and mice for which acute pancreatitis is induced, in the presence and absence of a CRAC inhibitor.
Figure 9B:
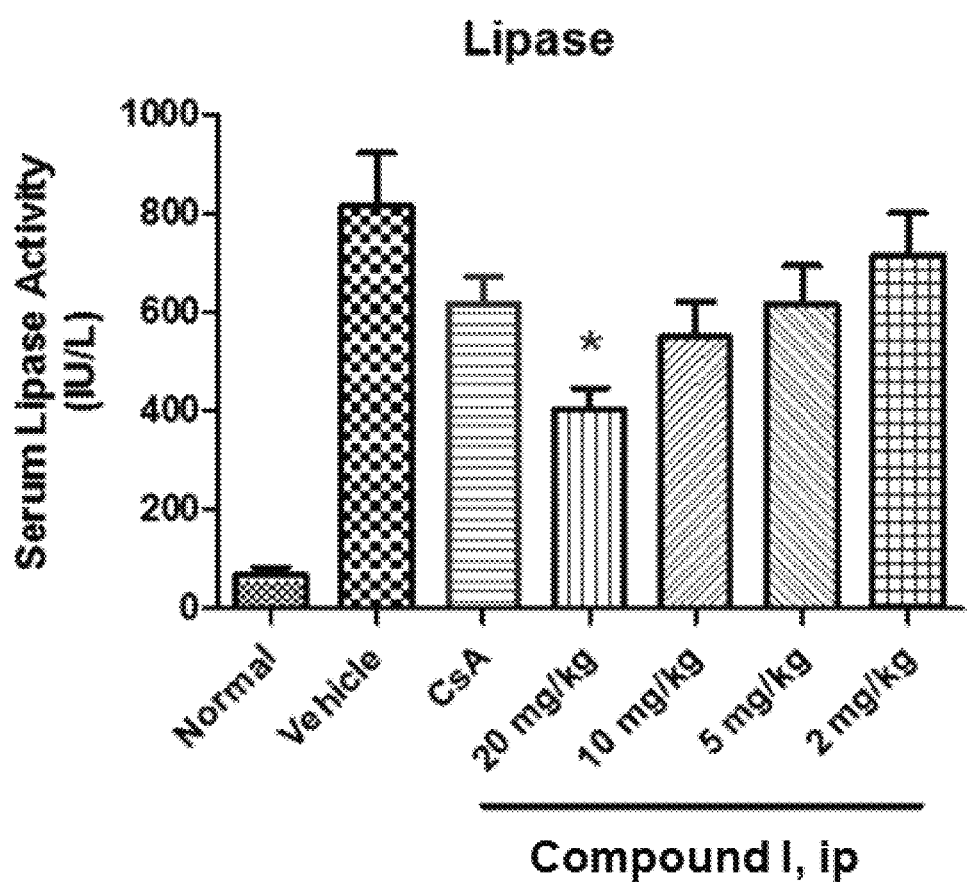
FIG. 9B shows serum Lipase levels in uninduced (normal) mice and mice for which acute pancreatitis is induced, in the presence and absence of a CRAC inhibitor.

Example 9: Compound I Lowers Serum Amylase and Serum Lipase Levels in Mouse Caerulein Model of Acute Pancreatitis Mice were either untreated (Normal), treated with CCK only (vehicle), or treated with CCK in combination with CsA or a CRAC inhibitor at the indicated dose. Serum amylase activity (FIG. 9A) and Serum Lipase activity (FIG. 9B) (IU/L) were measured.

The CRAC inhibitor Compound I performed as well as or better than the positive control CsA at maximal concentrations of 20 mg/kg. Compound I produced significant and dose-dependent reductions in caerulein-induced serum amylase and serum lipase activities

Figure 10:
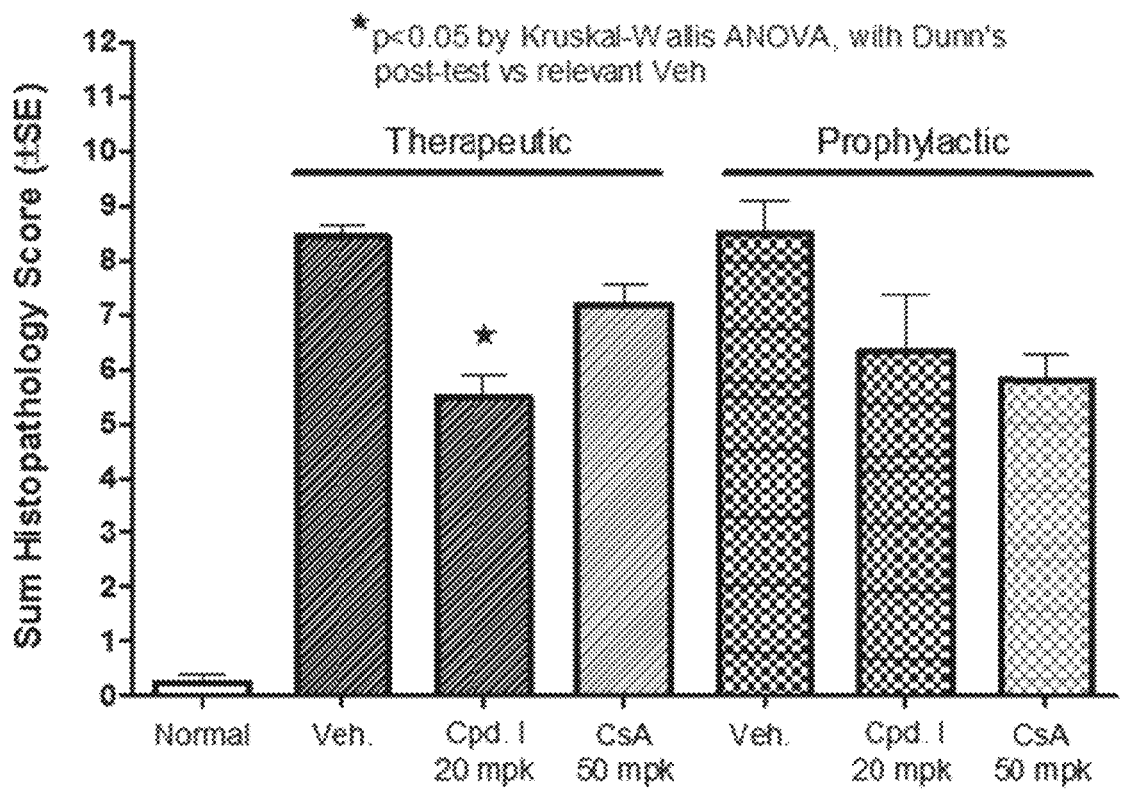
FIG. 10 shows histopathology scores for therapeutically and prophylactically treated mice upon acute pancreatitis induction.

Example 10: Compound I Reduces Pancreatic Pathology in Therapeutic Mouse Caerulein Model Seven hourly i.p. injections of caerulein were given to induce pancreatitis, with animals sacrificed 8 hr after the 1st injection. Compound I was administered i.p. either 30 min before the 1st caerulein injection (prophylactic), or after the 3rd injection (therapeutic). CsA was administered p.o. on the same schedule as Compound I. The results are depicted in FIG. 10.

Histopathology scores were measured in light of observation of Acinar cell degeneration, coagulation necrosis, and inflammation and edema measurements. Compound I produced a significant 35% reduction in caerulein-induced pathology in the pancreas when administered after the 3rd caerulein injection, consistent with efficacy in a therapeutic mode. Prophylactic treatment with Compound I also reduced pathology by 26%.

The results indicate that CRAC inhibitors such as Compound I have a substantial effect on pancreas histopathology scores when administered prophylactically or therapeutically.

Figure 11:
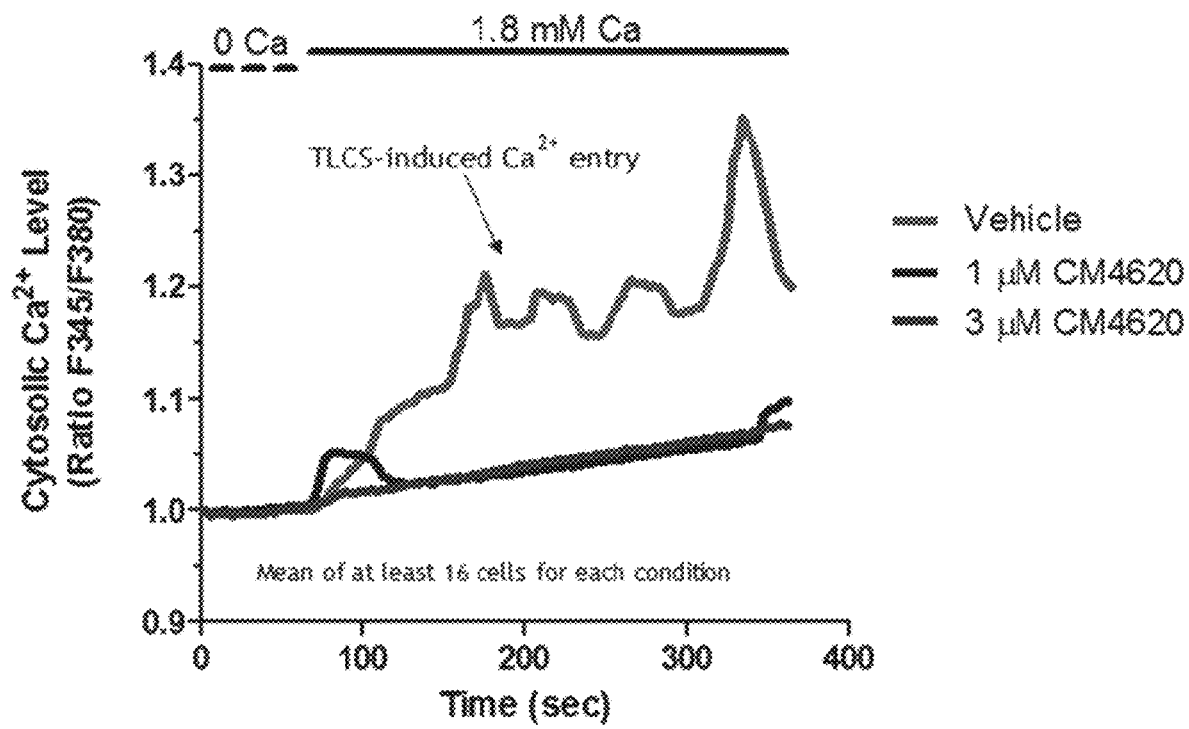
FIG. 11 shows TLCS-induced Calcium levels.

Example 11: Compound I Blocks TLCS-Induced $Ca^{2+}$ Entry in Mouse Pancreatic Acinar Cells Mouse PACs were treated with 500 µM TLCS and either 0, 1 µM or 3 µM of the CRAC inhibitor Compound I. Cytosolic Calcium levels (measured as $F_345/F_380$ ratios) were measured for each treatment. TLCS releases $Ca^{2+}$ from intracellular stores (not shown), initiating SOCE. In this experiment, Compound I at 1 or 3 µM completely blocked TLCS-induced $Ca^{2+}$ entry. The results are depicted in FIG. 11.

This result indicates that CRAC inhibitors may be effective at positively influencing Calcium signaling in Gall stone related acute pancreatitis in mammals.

Figure 12:
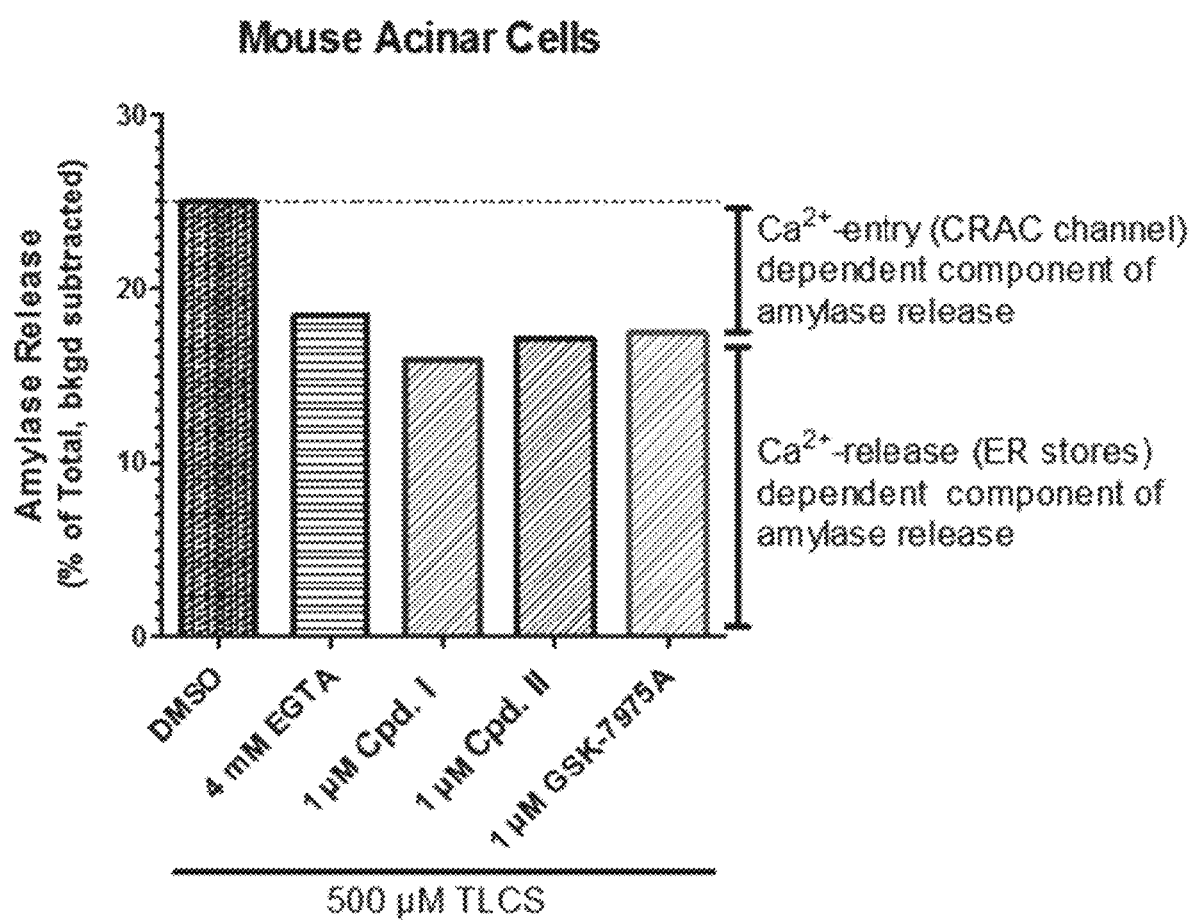
FIG. 12 shows mouse Acinar cell Amylase release levels.

Example 12: Compound I and Other CCIs Inhibit TLCS-Induced Amylase Release in Mouse Pancreatic Acinar Cells Amylase release from PACs has an ER calcium-dependent and a CRAC/cytosolic calcium-dependent component. The calcium dependent component is blocked by introduction of the divalent cation chelating agent EGTA. Mouse Acinar cells were treated with TLCS and either vehicle, EGTA, or a CRAC inhibitor such as Compound I, GSK-7975A or Compound II and monitored for Amylase release. It is observed that CRAC inhibitors mimicked EGTA in their effect on Amylase release. See FIG. 12.

This result indicates that CRAC inhibitors block the re-uptake of Calcium into the ER following TLCS-induced calcium release, thereby mimicking the effect of EGTA on the inhibition of Amylase release.

Example 13: Compound I Inhibits TLCS-Induced Necrosis in Mouse Pancreatic Acinar Cells Mouse PACs were treated with either DMSO, DMSO plus 500 µM TLCS, or DMSO plus 500 µM TLCS plus 1 µM of the CRAC inhibitor Compound I. Cell necrosis was measured as % PI uptake. The CRAC inhibitor Compound I inhibits TLCS-induced necrosis in mouse PACs.

These data, together with the $Ca^{2+}$ and amylase data, indicate that Compound I is efficacious in the TLCS model of AP.

Example 14: Phase II Clinical Trial of the Safety and Efficacy of Compounds Compound I, GSK-7975A, and Compound II in Patients with Acute Pancreatitis The purpose of this phase II trial is to investigate the safety, tolerability, PK, PD, and efficacy of single and repeat intravenous infusions of a Calcium signaling inhibitor such as Compound I, GSK-7975A, and Compound II, or compounds selected from the group of Compound A, in patients with acute pancreatitis and accompanying SIRS.

Patients:

The study will enroll 30 patients at high risk of developing moderate or severe pancreatitis, as assessed by a SIRS score of 2 or more at study entry.

Criteria:

Inclusion Criteria:

All subjects must use acceptable contraception to ensure that no pregnancies occur during the course of the study and for at least 12 weeks after dosing for males and for 32 weeks after dosing for females:

Body mass index within the range 18.5-35 $kg/m^2$ inclusive, in addition to a weight range of 55-95 kg;

The subject must be capable of giving informed consent and can comply with the study requirements and timetable;

Male and female subjects age 18 or higher are eligible.

Subjects must be experiencing a first in a lifetime episode of acute pancreatitis.

Diagnosis of acute pancreatitis must be based on 2 of the following 3 criteria: (1) typical upper abdominal pain; (2) elevation of serum amylase and/or lipase at least 3 times the upper limit of normal; (3) contrast-material enhanced CT scan or abdominal sonogram demonstrating changes of acute pancreatitis.

Subjects must demonstrate a history supporting alcoholic, hypertriglyceridemic or biliary etiology of the current pancreatitis episode (for biliary pancreatitis, a sonogram must exclude a stone obstruction at the time of study screening).

Subjects must demonstrate a BISAP score of 3 or higher

Study treatment initiation is possible within 48 h of symptom onset

Exclusion Criteria:

High likelihood for an invasive intra-biliary tract intervention (e.g. ERCP) in the coming week.

Recurrent episode of pancreatitis.

CT evidence of pancreatic necrosis at study entry.

Severe chronic renal failure (Modification of Diet in Renal Disease formula 30 mL/min or dependency on renal dialysis).

Class II or greater New York Heart Association heart failure.

Oxygen-dependent chronic obstructive pulmonary disease (COPD).

Cirrhosis of the liver.

Severe anemia (hemoglobin less than 8 g/dL).

Hematocrit below 35% or above 45% at study entry (fluids may be administered to correct the hematocrit before randomization as long as study treatment starts within 48 hours of symptoms onset).

Serum alanine aminotransferase above 250 IU/L at study entry.

Clinical suspicion of ascending cholangitis at study entry.

Active gastrointestinal bleeding.

Current malignancy not in remission (other than basal cell carcinoma of skin).

Altered mental status.

Current breastfeeding or pregnancy.

Female of childbearing potential (less than 2 years post-menopausal or not surgically sterilized) who is not willing to use adequate and effective birth control measures Known hypersensitivity to any component of the investigational product.

Dependent relationship with the investigator or the sponsor.

Participation in an investigational drug study during this clinical trial or within 30 days prior to start of this clinical trial.

Study Design:

The study is a randomized, double blind, placebo-controlled, multi-center, multi-national, parallel-arm study comparing a placebo group to a CRAC inhibitor group treated intravenously with a CRAC inhibitor twice daily for up to 7 consecutive days.

The study will enroll 45 patients at high risk of developing moderate or severe pancreatitis, as assessed by a SIRS score of 2 or more at study entry.

The primary study endpoint is the effect of a CRAC inhibitor on systemic inflammation in acute pancreatitis as reflected by a change in SIRS score or C-reactive protein (CRP) plasma levels.

Clinical trial material administration will begin within 24 hours of acute pancreatitis symptoms onset, or 18 hours of hospital admittance. Subjects will be randomized at a ratio of 1:1 to receive either a CRAC inhibitor at one of two doses, or placebo. The serum levels of a CRAC inhibitor at the end of each 2-hour infusion will also be monitored.

The study duration per individual subject will be 14 days, consisting of a screening evaluation followed by an up to 7 day double blind treatment period, which will be part of an in-hospital observation period of at least 7 days, and a follow-up final visit on Day 14.

Primary Outcome Measures:

C-reactive protein serum concentration.

Change in SIRS at 48 hours

Blood amylase and lipase level.

Secondary Outcome Measures, CRAC Inhibitor Vs. Placebo:

Safety of a CRAC inhibitor in this population of patients (through routine safety laboratory tests, Physical examination and vital signs monitoring, ECG and adverse event reporting), A CRAC inhibitor's effects on other plasma inflammatory markers (interleukin-6, matrix metalloproteinase 9, tumor necrosis factor alpha, etc.)

CRAC inhibitor effects on the clinical course of pancreatitis (based on changes in clinical rating scales such as the Bedside Index for Severity in Acute Pancreatitis (BISAP), Systemic Inflammatory Response Syndrome (SIRS) and Acute Physiology And Chronic Health Evaluation II (APACHE II) scores, and on contrast material-enhanced abdominal Computerized Tomography (CT),

- Progression in the Sequential Organ Failure Assessment (SOFA) Score
- Progression in the Multiple Organ Dysfunction Score (MODS)
- Progression in the Systemic Inflammatory Response Syndrome
- Progression in the inflammatory and anti-inflammatory mediators (IL-1RA, IL-10, IL-6. IL-18, TNF-a, ICAM-1, IL-10 etc.).
- Escalation of care to high dependency or intensive care unit and length of hospital stay.

Example 15: Compound I Inhibits Junin Virus Budding in Infected VeroE6 Cells

VeroE6 cells infected with live attenuated Candid-1 JUNV are treated with either DMSO, DMSO plus 500 μM TLCS, DMSO plus 500 μM TLCS plus 1 μM of the CRAC inhibitor Compound I, DMSO plus 500 μM TLCS plus 10 μM Compound I, DMSO plus 500 μM TLCS plus 25 μM Compound I, or DMSO plus 500 μM TLCS plus 50 μM Compound I. Infectious virions produced from these cells are quantified in a focus-forming assay. Enumeration of JUNV foci reveals a statistically significant, dose-dependent reduction in JUNV virus production following treatment with Compound I.

These data, together with the $Ca^{2+}$ data, indicate that Compound I is efficacious in inhibiting viral budding of the JUNV virus.

Example 16: Compound I Differentially Inhibits Store-Operated $Ca^{2+}$ Entry-Dependent Th1, Th2, and Th17 Differentiation Naive and stimulated murine T cells cultured under Th1-, Th2-, and Th17-polarizing conditions are treated with either DMSO, DMSO plus 500 μM TLCS, or DMSO plus 500 μM TLCS plus 1 μM of the CRAC inhibitor Compound I. Store-operated $Ca^{2+}$ entry (SOCE) is quantified in each treatment. Compound I blocks SOCE stronger in differentiated Th17 cells than in naive, Th1, or Th2 cells. In addition, IL-17A production by Th17 cells is more severely affected when compared with IFN-γ and IL-4 production by Th1 and Th2 cells, respectively, in the presence of Compound I.

These data, together with the $Ca^{2+}$ and additional transcription factor (i.e., IL-17A, RORα, and RORγt) expression data, indicate that Compound I is efficacious in inhibiting Th17 differentiation.

What is claimed is:

1. A compound having the chemical name N-(5-(6-chloro-2,2-difluorobenzo[d][1,3]dioxol-5-yl)pyrazin-2-yl)-2-fluoro-6-methylbenzamide or a pharmaceutically acceptable salt thereof.

2. A pharmaceutical composition comprising the compound of claim 1 and a pharmaceutically acceptable excipient thereof.

* * * * *